United States Patent
Sasaki et al.

(10) Patent No.: US 10,215,898 B2
(45) Date of Patent: Feb. 26, 2019

(54) NEAR INFRARED RAY ABSORBENT COMPOSITION, NEAR INFRARED RAY CUT FILTER, SOLID IMAGE PICKUP ELEMENT, AND CAMERA MODULE

(71) Applicant: FUJIFILM Corporation, Tokyo (JP)

(72) Inventors: Kouitsu Sasaki, Shizuoka (JP); Takashi Kawashima, Shizuoka (JP); Seiichi Hitomi, Shizuoka (JP); Yasuharu Shiraishi, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/497,959

(22) Filed: Apr. 26, 2017

(65) Prior Publication Data
US 2017/0227690 A1    Aug. 10, 2017

Related U.S. Application Data

(63) Continuation of application No. PCT/JP2015/079954, filed on Oct. 23, 2015.

(30) Foreign Application Priority Data

Oct. 28, 2014 (JP) .................................. 2014-219261
Sep. 11, 2015 (JP) .................................. 2015-179497

(51) Int. Cl.
*C07F 1/08* (2006.01)
*G02B 5/20* (2006.01)
(Continued)

(52) U.S. Cl.
CPC ................ *G02B 5/208* (2013.01); *C07F 1/08* (2013.01); *C07F 9/113* (2013.01); *H04N 5/2254* (2013.01)

(58) Field of Classification Search
CPC ........ G02B 5/208; G02B 5/0891; G02B 5/09; G02B 1/04; G02B 26/0833; G02B 5/223;
(Continued)

(56) References Cited

U.S. PATENT DOCUMENTS

| 2005/0008969 A1* | 1/2005 | Miyako ............... C09B 23/0066 |
| | | 430/270.1 |
| 2016/0037034 A1* | 2/2016 | Inasaki .................. G02B 5/208 |
| | | 348/360 |
| 2017/0092435 A1* | 3/2017 | Tsuna ................... H01G 9/2059 |

FOREIGN PATENT DOCUMENTS

| JP | 11-52127 A | 2/1999 |
| JP | 2002-69305 A | 3/2002 |

(Continued)

OTHER PUBLICATIONS

JPO 2000-007870 Original and English machine translation.*
(Continued)

*Primary Examiner* — Thomas K Pham
*Assistant Examiner* — Sharrief I Broome
(74) *Attorney, Agent, or Firm* — Birch, Stewart, Kolasch & Birch, LLP

(57) ABSTRACT

Provided are a near infrared ray absorbent composition which can form a cured film having excellent near infrared ray shielding properties, a near infrared ray cut filter, a manufacturing method of a near infrared ray cut filter, a solid image pickup element, and a camera module. The near infrared ray absorbent composition includes a copper complex that is other than a copper phthalocyanine complex and has a maximum absorption wavelength in a wavelength range of 700 to 1,200 nm and in which a molar light absorption coefficient at the maximum absorption wavelength is greater than or equal to 100 (L/mol·cm).

20 Claims, 2 Drawing Sheets

(51) Int. Cl.
   *C07F 9/113*      (2006.01)
   *H04N 5/225*      (2006.01)

(58) Field of Classification Search
   CPC .... G02B 1/10; G02B 5/0284; G02B 13/0045;
         G02B 13/143; G02B 19/0023; G02B
         19/0042; G02B 19/0095; G02B 1/11;
         G02B 1/115; G02B 1/118; G02B 1/14;
         G03F 7/702; G03F 7/70075; G03F
         7/70116; G03F 7/7015; G03F 7/70233;
         G03F 7/70316; G03F 7/70958; G03F
         7/70083; G03F 7/70191; G03F 7/70291;
         G03F 7/70566; G03F 7/70825; G03F
         7/70891; G03F 1/24; G03F 1/52; G03F
         1/84; B32B 17/10036; B32B 17/10229;
         B32B 2307/412; B32B 2307/71; B32B
         27/08; B32B 37/12; B32B 7/02; B32B
         7/12; B32B 17/06; B32B 17/10; B32B
         17/10174; B32B 17/1022; B32B
         17/10247; B32B 17/10293; B32B
         17/10467; B32B 17/10504
   See application file for complete search history.

(56) References Cited

FOREIGN PATENT DOCUMENTS

| | | |
|---|---|---|
| JP | 2003-292936 A | 10/2003 |
| JP | 2005-49847 A | 2/2005 |
| JP | 2011-63814 A | 3/2011 |
| WO | WO 2014/168221 A1 | 10/2014 |

OTHER PUBLICATIONS

International Search Report for PCT/JP2015/079954 (PCT/ISA/210) dated Dec. 8, 2015.
Written Opinion of the International Searching Authority for PCT/JP2015/079954 (PCT/ISA/237) dated Dec. 8, 2015.
Notification of Transmittal of Translation of the International Preliminary Report on Patentability; International Preliminary Report on Patentability and English translation of Written Opinion of the International Searching Authority dated May 11, 2017 in PCT/JP2015/079954 (Forms PCT/IB/338, PCT/IB/373 and PCT/ISA/237).
Japanese Notification of Reasons of Refusal, dated Mar. 13, 2018, for corresponding Japanese application No. 2016-556535, with an English machine translation.

* cited by examiner

NEAR INFRARED RAY ABSORBENT COMPOSITION, NEAR INFRARED RAY CUT FILTER, SOLID IMAGE PICKUP ELEMENT, AND CAMERA MODULE

CROSS-REFERENCE TO RELATED APPLICATIONS

This application is a Continuation of PCT International Application No. PCT/JP2015/079954 filed on Oct. 23, 2015, which claims priority under 35 U.S. § 119(a) to Japanese Patent Application No. 2014-219261 filed on Oct. 28, 2014 and Japanese Patent Application No. 2015-179497 filed on Sep. 11, 2015. Each of the above application(s) is hereby expressly incorporated by reference, in its entirety, into the present application

BACKGROUND OF THE INVENTION

1. Field of the Invention

The present invention relates to a near infrared ray absorbent composition, a near infrared ray cut filter, a solid image pickup element, and a camera module.

2. Description of the Related Art

A charge coupled device (CCD) image sensor or a complementary metal-oxide semiconductor (CMOS) image sensor which is a solid image pickup element is used in a video camera, a digital still camera, a mobile phone with a camera function, and the like. In order to use a silicon photodiode having sensitivity with respect to a near infrared ray in a light receiving section of the solid image pickup element, it is necessary to perform visual sensitivity correction, and there are many cases of using a near infrared ray cut filter.

A near infrared ray absorbent composition containing a copper phosphoric acid ester complex has been known as a material of the near infrared ray cut filter, for example (JP2002-69305A, JP1999-52127A (JP-H11-52127A), and JP2011-63814A).

SUMMARY OF THE INVENTION

However, in the near infrared ray absorbent composition disclosed in JP2002-69305A, JP1999-52127A (JP-H11-52127A), and JP2011-63814A, near infrared ray shielding properties were insufficient, and thus, it was necessary to increase a film thickness of a filter, in order to obtain sufficient shielding properties. In order to increase a film thickness of the filter, it was necessary to perform formulation with a large amount of curable compounds or other additives, and thus, great effects of these components were received.

The present invention has been made in order to solve such a problem, and an object of present invention is to provide a near infrared ray absorbent composition which can form a cured film having excellent shielding properties in a near infrared ray range, a near infrared ray cut filter, a solid image pickup element, and a camera module.

As a result of intensive studies of the present inventors, it has been found that a cured film having excellent near infrared ray shielding properties, even with a thin thickness, can be formed by using a specified copper complex, and thus, the present invention has been completed. The present invention provides the followings.

<1> A near infrared ray absorbent composition, comprising: a copper complex that is other than a copper phthalocyanine complex and has a maximum absorption wavelength in a wavelength range of 700 to 1,200 nm and in which a molar light absorption coefficient at the maximum absorption wavelength is greater than or equal to 100 (L/mol·cm).

<2> A near infrared ray absorbent composition comprising: a copper complex that includes a compound not having a maximum absorption wavelength in a wavelength range of 400 to 600 nm as a ligand and has a maximum absorption wavelength in a wavelength range of 700 to 1,200 nm and in which a molar light absorption coefficient at the maximum absorption wavelength is greater than or equal to 100 (L/mol·cm).

<3> The near infrared ray absorbent composition according to <1> or <2>, in which, in the copper complex, a 5-membered ring and/or a 6-membered ring is formed by copper and a ligand.

<4> The near infrared ray absorbent composition according to any one of <1> to <3>, in which the copper complex is a copper complex including a compound having at least two coordination portions as a ligand.

<5> The near infrared ray absorbent composition according to any one of <1> to <4>, in which the copper complex is a copper complex including a compound having three coordination portions as a ligand, a copper complex including a compound having four coordination portions as a ligand, or a copper complex including a compound having five coordination portions as a ligand.

<6> The near infrared ray absorbent composition according to <5>, in which the copper complex is a copper complex including a compound having three coordination portions as a ligand and further includes at least one unidentate ligand.

<7> The near infrared ray absorbent composition according to <6>, in which at least one unidentate ligand is a unidentate ligand performing coordination by an anion.

<8> The near infrared ray absorbent composition according to any one of <1> to <5>, in which the copper complex is a copper complex including a compound having three coordination portions and a compound having two coordination portions as ligands.

<9> The near infrared ray absorbent composition according to <8>, in which the compound having three coordination portions is a compound having two coordination portions performing coordination by an anion and one coordination portion performing coordination by an unshared electron pair, and the compound having two coordination portions is a compound having two coordination portions performing coordination by an unshared electron pair.

<10> The near infrared ray absorbent composition according to any one of <1> to <5>, in which the copper complex is a copper complex having a compound having four coordination portions as a ligand or a copper complex having a compound having five coordination portions as a ligand.

<11> The near infrared ray absorbent composition according to any one of <1> to <5>, in which the copper complex is a copper complex including a compound having four coordination portions as a ligand, and further includes at least one unidentate ligand.

<12> The near infrared ray absorbent composition according to <5>, <10>, or <11>, in which the compound having four coordination portions is a compound having four coordination portions performing coordination by an unshared electron pair.

<13> The near infrared ray absorbent composition according to <5>, <10>, or <11>, in which the compound having four coordination portions is a compound represented by the following Formula (IV-12);

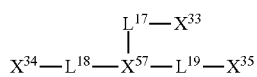

(IV-12)

in General Formula (IV-12), $X^{33}$ to $X^{35}$ and $X^{57}$ each independently represent a coordination portion and $L^{17}$ to $L^{19}$ each independently represent a single bond or a divalent linking group.

<14> The near infrared ray absorbent composition according to any one of <1> to <13>, in which the content of the copper complex is greater than or equal to 15 mass % with respect to the total solid content of the near infrared ray absorbent composition.

<15> The near infrared ray absorbent composition according to any one of <1> to <14>, further comprising: a curable compound; and a solvent.

<16> The near infrared ray absorbent composition according to any one of <1> to <15>, in which, when a film having a film thickness after being dried of 100 μm is prepared by using the near infrared ray absorbent composition, light transmittance in a thickness direction of the film at a wavelength of 550 nm is greater than or equal to 45%, and light transmittance at a wavelength of 800 nm is less than or equal to 25%.

<17> A near infrared ray cut filter obtained by using the near infrared ray absorbent composition according to any one of <1> to <16>.

<18> The near infrared ray cut filter according to <17>, in which a film thickness is less than or equal to 300 μm.

<19> A solid image pickup element comprising: a near infrared ray cut filter obtained by using the near infrared ray absorbent composition according to any one of <1> to <16>.

<20> A camera module comprising: a solid image pickup element; and a near infrared ray cut filter disposed on the solid image pickup element on a light receiving side, in which the near infrared ray cut filter is the near infrared ray cut filter according to <17>.

According to the present invention, it is possible to provide a near infrared ray absorbent composition which can form a cured film having excellent near infrared ray shielding properties, a near infrared ray cut filter, a solid image pickup element, and a camera module.

Figure 1:
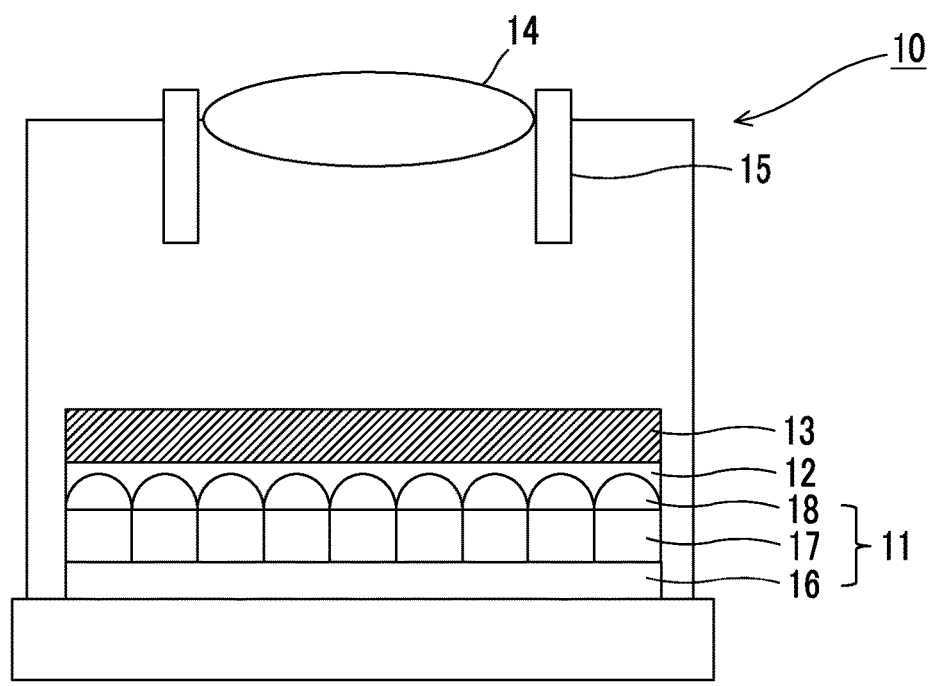
FIG. 1 is a schematic sectional view illustrating a configuration of a camera module according to an embodiment of the present invention, which includes a near infrared ray cut filter.

DESCRIPTION OF THE PREFERRED
EMBODIMENTS

Hereinafter, the contents of the present invention will be described in detail. Further, here, "to" is used as the meaning which includes numerical values before and after "to" as the lower limit value and the upper limit value.

Here, "(meth)acrylate" indicates acrylate and methacrylate, "(meth)acryl" indicates acryl and methacryl, "(meth)allyl" indicates allyl and methallyl, and "(meth)acryloyl" indicates acryloyl and methacryloyl.

Here, in the description of a group (an atomic group), a description not indicating substitution and non-substitution includes a group (an atomic group) having a substituent along with a group (an atomic group) not having a substituent.

Here, in chemical formula, Me indicates a methyl group, Et indicates an ethyl group, Pr indicates a propyl group, Bu indicates a butyl group, and Ph indicates a phenyl group.

Here, a near infrared ray indicates light (an electromagnetic wave) in a wavelength range of 700 to 2,500 nm.

Here, the total solid content indicates the total mass of components obtained by removing a solvent from the total composition of a composition.

Here, a solid content indicates a solid content at 25° C.

Here, a weight-average molecular weight is defined as a value in terms of polystyrene of gel permeation chromatography (GPC) measurement. Here, a weight-average molecular weight (Mw) and a number average molecular weight (Mn), for example, can be obtained by using HLC-8220 (manufactured by TOSOH CORPORATION), by using TSKgel Super AWM-H (manufactured by TOSOH CORPORATION, 6.0 mmID×15.0 cm) as a column, and by using a solution of lithium bromide NMP (N-methyl pyrrolidinone) of 10 mmol/L as an eluant.

<Near Infrared Ray Absorbent Composition>

According to First Embodiment of the near infrared ray absorbent composition of the present invention, there is provided a near infrared ray absorbent composition including a copper complex that is other than a copper phthalocyanine complex and has a maximum absorption wavelength in a wavelength range of 700 to 1,200 nm and in which a molar light absorption coefficient at the maximum absorption wavelength is greater than or equal to 100 (L/mol·cm).

According to Second Embodiment of the near infrared ray absorbent composition of the present invention, there is provided a near infrared ray absorbent composition including a copper complex that includes a compound not having a maximum absorption wavelength in a wavelength range of 400 to 600 nm as a ligand and has a maximum absorption wavelength in a wavelength range of 700 to 1,200 nm and in which a molar light absorption coefficient at the maximum absorption wavelength is greater than or equal to 100 (L/mol·cm).

Here, the copper phthalocyanine complex is a copper complex including a compound having a phthalocyanine skeleton as a ligand. In the compound having a phthalocyanine skeleton, a π electron conjugated system is spread over the entirety of molecules and has a planar structure. The copper phthalocyanine complex absorbs light by π-π* transition. In order to absorb light in an infrared region by π-π* transition, it is necessary that a compound which is a ligand has a long conjugated structure. However, when the conjugated structure of the ligand is long, visible light transmittance tends to decrease. Accordingly, the copper phthalocyanine complex has insufficient visible light transmittance.

In addition, a copper complex including a compound having a maximum absorption wavelength in a wavelength range of 400 to 600 nm as a ligand performs absorption in a visible range (for example, a wavelength range of 400 to 600 nm), and thus, visible light transmittance is insufficient.

As the compound having a maximum absorption wavelength in a wavelength range of 400 to 600 nm, a compound which has a long conjugated structure and greatly absorbs light by π-π* transition is used. Specifically, a compound having a phthalocyanine skeleton is used.

The near infrared ray absorbent composition of the present invention includes a copper complex other than the copper phthalocyanine complex or a copper complex including a compound not having a maximum absorption wavelength in a wavelength range of 400 to 600 nm as a ligand, as the copper complex which has a maximum absorption wavelength in a wavelength range of 700 to 1,200 nm and in which a molar light absorption coefficient at the maximum absorption wavelength is greater than or equal to 100 (L/mol·cm), and therefore, it is possible to form a cured film having excellent near infrared ray shielding properties. In addition, visible light transmittance is also excellent.

In the present invention, at least a copper complex other than the copper phthalocyanine complex or a copper complex including a compound not having a maximum absorption wavelength in a wavelength range of 400 to 600 nm as a ligand is included as the copper complex which has a maximum absorption wavelength in a wavelength range of 700 to 1,200 nm and in which a molar light absorption coefficient at the maximum absorption wavelength is greater than or equal to 100 (L/mol·cm), and as will be described later, other near infrared ray absorbent compounds such as the copper phthalocyanine complex can be further included, in order to adjust film spectra.

The copper complex used in the present invention has a maximum absorption wavelength in a wavelength range of 700 to 1,200 nm. The maximum absorption wavelength of the copper complex is more preferably in a wavelength range of 720 to 1,200 nm and is even more preferably in a wavelength range of 800 to 1,100 nm. The maximum absorption wavelength can be measured, for example, by using a Cary 5000 UV-Vis-NIR (spectrophotometer, manufactured by Agilent Technologies, Inc.).

The molar light absorption coefficient of the copper complex in the maximum absorption wavelength in the wavelength range described above is preferably greater than or equal to 120 (L/mol·cm), more preferably greater than or equal to 150 (L/mol·cm), even more preferably greater than or equal to 200 (L/mol·cm), still more preferably greater than or equal to 300 (L/mol·cm), and particularly preferably greater than or equal to 400 (L/mol·cm). The upper limit thereof is not particularly limited, but can be set to be, for example, less than or equal to 30,000 (L/mol·cm). When the molar light absorption coefficient of the copper complex is greater than or equal to 100 (L/mol·cm), it is possible to form a cured film having excellent near infrared ray shielding properties, even with a thin thickness. In order to obtain a thick cured film, it is necessary to increase a formulation amount of curable compounds or other additives. However, since a thin film can be obtained, it is possible to decrease a formulation amount of curable compounds or other additives and it is also possible to further prevent an effect on near infrared ray shielding properties due to these components.

A gram light absorption coefficient of the copper complex at 800 nm is preferably greater than or equal to 0.11 (L/g·cm), more preferably greater than or equal to 0.15 (L/g·cm), and even more preferably greater than or equal to 0.24 (L/g·cm).

In the present invention, the molar light absorption coefficient and the gram light absorption coefficient of the copper complex can be obtained by preparing a solution having a concentration of 1 g/L by dissolving a copper complex in a solvent, and performing measurement of absorption spectra of the solution obtained by dissolving the copper complex. As a measurement device, UV-1800 (wavelength range of 200 to 1,100 nm) manufactured by Shimadzu Corporation or Cary 5000 (wavelength range of 200 to 1,300 nm) manufactured by Agilent Technologies, Inc. can be used. Examples of a measurement solvent include water, N, N-dimethylformamide, propylene glycol monomethyl ether, 1,2, 4-trichlorobenzene, and acetone. In the present invention, a solvent in which a copper complex which is a measurement target can be dissolved is selected and used among the measurement solvents described above. Among those, in a case of a copper complex which dissolves in propylene glycol monomethyl ether, propylene glycol monomethyl ether is preferably used as the measurement solvent. The term "dissolving" means a state in which solubility of the copper complex with respect to the solvent at 25° C. exceeds 0.01 g/100 g Solvent.

In the present invention, the molar light absorption coefficient and the gram light absorption coefficient of the copper complex are preferably values measured by using any one of the measurement solvents described above and more preferably values measured by using propylene glycol monomethyl ether.

In the copper complex other than the copper phthalocyanine complex and the copper complex including a compound not having a maximum absorption wavelength in a wavelength range of 400 to 600 nm as a ligand, examples of a method of setting the molar light absorption coefficient to be greater than or equal to 100 (L/mol·cm) include a method of using a pentacoordinate copper complex, a method of using a ligand having high π donation, and a method of using a copper complex having low symmetry.

A mechanism in which the molar light absorption coefficient can be greater than or equal to 100 (L/mol·cm) by using a pentacoordinate copper complex is assumed as follows. That is, when a pentacoordinate copper complex (for example, having a trigonal bipyramidal structure, square pyramidal structure, or an intermediate structure thereof) is used, symmetry of the complex decreases. Accordingly, a composite state of a p orbital and a d orbital is easily obtained in a mutual interaction between the ligand and copper. At this time, d-d transition (absorption in the infrared region) is no more pure d-d transition and p-d transition which is allowed transition is mixed therewith. Accordingly, it is thought that the light absorption coefficient is improved and can be greater than or equal to 100 (L/mol·cm).

The pentacoordinate copper complex can be prepared, for example, by causing two bidentate ligands (may be the same as each other or different from each other) and one unidentate ligand to react with copper ion, by causing one tridentate ligands and two bidentate ligands (may be the same as each other or different from each other) to react with copper ion, by causing one tridentate ligand and one bidentate ligand to react with copper ion, by causing one quadridentate ligand and one unidentate ligand to react with copper ion, or by causing one pentadentate ligand to react with copper ion. At this time, a unidentate ligand performing coordination by an unshared electron pair may be used as a reaction solvent. For example, when two bidentate ligands are reacted with copper ion in a solvent including water, a pentacoordinate complex in which the two bidentate ligands and water as a unidentate ligand are coordinated is obtained.

A mechanism of achieving a molar light absorption coefficient to be greater than or equal to 100 (L/mol·cm) by using a ligand having high π donation is assumed as follows. That is, when a ligand having high π donation (a ligand in which a π orbital or p orbital of the ligand is at a position having low energy) is used, a composite state of a p orbital of metal and a p orbital (or π orbital) of the ligand is easily obtained. At this time, d-d transition is no more pure d-d transition and ligand to metal charge transfer (LMCT) transition which is allowed transition is mixed therewith. Accordingly, it is thought that the light absorption coefficient is improved and can be greater than or equal to 100 (L/mol·cm).

Examples of the ligand having high π donation include a halogen ligand, an oxygen anion ligand, and a sulfur anion ligand. As a copper complex using the ligand having high π donation, for example, a copper complex including Cl ligands as unidentate ligands is used.

A copper complex having low symmetry can be obtained by using ligands having low symmetry or by asymmetrically introducing ligands to copper ion. For example, specific descriptions are as follows.

For example, in a case of using a tridentate ligand $L^1$-$L^2$-$L^3$ and two unidentate ligands $L^4$ and $L^5$, a copper complex having low symmetry is obtained by using a ligand having low symmetry, for example, a ligand in which $L^1$ and $L^3$ are different from each other, as shown in the following Formula (1). In a case where the ligands are asymmetrically introduced with respect to the copper ion, for example, in a case where $L^4$ and $L^5$ are different from each other, a copper complex having low symmetry is obtained, rather than in a case where $L^4$ and $L^5$ are the same as each other.

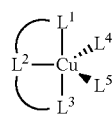

(1)

When $L^4$ and $L^5$ are the same as each other in a square pyramidal complex, in a case where $L^4$ and $L^5$ are adjacent to each other on a bottom surface of the square pyramid as shown in the following Formula (3) or one unidentate ligand is on the top of the square pyramid as shown in the following Formula (4), a complex having low symmetry is obtained, rather than in a case where $L^4$ and $L^5$ are on a diagonal line on the bottom surface of the square pyramid as shown in the following Formula (2).

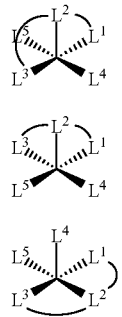

(2)

(3)

(4)

In a case of using two bidentate ligands $L^6$-$L^7$ and $L^8$-$L^9$ and a unidentate ligand $L^{10}$, a copper complex having low symmetry is obtained by using ligands having low symmetry, for example, by using a ligand in which $L^6$ and $L^7$ are different from each other and/or a ligand in which $L^8$ and $L^9$ are different from each other, as shown in the following Formula (5).

In a case where the ligands are asymmetrically introduced with respect to the copper ion, for example, in a case where $L^6$-$L^7$ and $L^8$-$L^9$ are different from each other, a copper complex having low symmetry is obtained, rather than in a case where $L^6$-$L^7$ and $L^8$-$L^9$ are the same as each other. In a case where $L^6$-$L^7$ and $L^8$-$L^9$ are the same as each other, a copper complex having low symmetry is obtained, in a case where $L^6$=$L^9$ and $L^7$=$L^8$, rather than in a case where $L^6$=$L^8$ and $L^7$=$L^9$.

(5)

The copper complex of the present invention is preferably a pentacoordinate copper complex. As a geometric structure of the pentacoordinate copper complex, a trigonal bipyramidal structure or a square pyramidal structure is used, but all of the copper complexes are not clearly classified into the structures described above, and an intermediate structure thereof also exists. A τ value (trigonality index) is known as an index indicating that the structure of the pentacoordinate copper complex is close to the trigonal bipyramidal structure or a square pyramidal structure, and the τ value is defined by the following expression.

τ=[(maximum L-M-L angle)−(second largest L-M-L angle)]/60

(here, L represents a coordination portion and M represents a metal center)

when the τ value is close to 1, the τ value indicates that the structure of the complex is a structure close to the trigonal bipyramidal structure, when the τ value is close to 0, the structure of the complex is a structure close to the square pyramidal structure. The τ value is normally a value of 0 to 1, but may be a value larger than 1 as shown below.

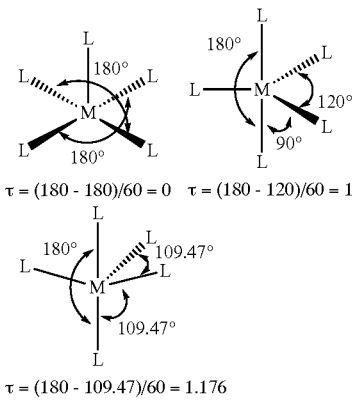

In the present invention, it is preferable that the copper complex has a structure close to the trigonal bipyramidal structure, in a viewpoint of easily obtaining a maximum absorption wavelength on a long wavelength side in a wavelength range of 700 to 1,200 nm.

The τ value of the copper complex is preferably greater than or equal to 0.5, more preferably greater than or equal to 0.75, and even more preferably greater than or equal to 0.9. The upper limit of the τ value is not particularly limited, and can be, for example, less than or equal to 1.176.

In the present invention, it is preferable that the copper complex includes a compound (hereinafter, also referred to as a compound (A)) including at least two coordination portions as a ligand. The compound (A) more preferably has at least three coordination portions and even more preferably has three to five coordination portions. The compound (A) functions as a chelating ligand with respect to a copper component. That is, it is considered that at least two coordination atoms included in the compound (A) chelating-coordinates with copper, and thus, the structure of the copper complex is distorted, high transmittance in a visible light range is obtained, light absorption power of a near infrared ray is improved, and a color valency is also improved. Accordingly, even when a near infrared ray cut filter is used for a long time, the characteristics thereof are not deteriorated, and it is also possible to stably manufacture a camera module.

The copper complex used in the present invention may include two or more compounds (A). In a case of including two or more compounds (A), the respective compounds (A) may be the same as each other or different from each other.

As the coordination portion included in the compound (A), a coordination portion performing coordination by an anion, a coordination portion performing coordination by an unshared electron pair, and the like are used.

As the copper complex used in the present invention, a tetracoordinate copper complex, a pentacoordinate copper complex, and a hexacoordinate copper complex are exemplified, a tetracoordinate copper complex and a pentacoordinate copper complex are more preferable, and a pentacoordinate copper complex is even more preferable.

In addition, in the copper complex, it is preferable that a 5-membered ring and/or a 6-membered ring is formed by copper and ligands. Such a copper complex has a stable form and has excellent complex stability.

For example, the copper in the copper complex used in the present invention can be obtained by mixing and reacting the compound (A) with a copper component (copper or a compound containing copper).

The copper component is preferably a compound containing divalent copper. Only one type of the copper component may be used, or two or more types thereof may be used.

For example, as the copper component, copper oxide or a copper salt can be used. For example, as the copper salt, copper carboxylate (for example, copper acetate, copper ethyl acetoacetate, copper formate, copper benzoate, copper stearate, copper naphthenate, copper citrate, copper 2-ethyl hexanoate, and the like), copper sulfonate (for example, copper methane sulfonate and the like), copper phosphate, copper phosphoric acid ester, copper phosphonate, copper phosphonic acid ester, copper phosphinate, copper amide, copper sulfone amide, copper imide, copper acyl sulfone imide, copper bissulfone imide, copper methide, alkoxy copper, phenoxy copper, copper hydroxide, copper carbonate, copper sulfate, copper nitrate, copper perchlorate, copper fluoride, copper chloride, and copper bromide are preferable, the copper carboxylate, the copper sulfonate, the copper sulfone amide, the copper imide, the copper acyl sulfone imide, the copper bissulfone imide, the alkoxy copper, the phenoxy copper, the copper hydroxide, the copper carbonate, the copper fluoride, the copper chloride, the copper sulfate, and the copper nitrate are more preferable, the copper carboxylate, the copper acyl sulfone imide, the phenoxy copper, the copper chloride, the copper sulfate, and the copper nitrate are even more preferable, and the copper carboxylate, the copper acyl sulfone imide, the copper chloride, and the copper sulfate are particularly preferable.

A molar ratio (compound (A):copper component) regarding the amount of the copper component reacting with the compound (A) is preferably 1:0.5 to 1:8 and more preferably 1:0.5 to 1:4.

In the reaction conditions when reacting the copper component and the compound (A) with each other, it is preferable that the temperature is 20° C. to 100° C. and the time is equal to or longer than 0.5 hours, for example.

The copper complex used in the present invention may include a ligand other than the compound (A). As the ligand other than the compound (A), a unidentate ligand performing coordination by an anion or an unshared electron pair is used. Examples of a ligand performing coordination by an anion include a halide anion, a hydroxide anion, an alkoxide anion, a phenoxide anion, an amide anion (including amide substituted with an acyl group or a sulfonyl group), an imide anion (including imide substituted with an acyl group or a sulfonyl group), an anilide anion (including anilide substituted with an acyl group or a sulfonyl group), a thiolate anion, a hydrogen carbonate anion, a carboxylate anion, a thiocarboxylate anion, a dithiocarboxylate anion, a hydrogen sulfate anion, a sulfonate anion, a dihydrogen phosphate anion, a phosphoric acid diester anion, a phosphonic acid monoester anion, a hydrogen phosphonate anion, a phosphinate anion, nitrogen-containing heterocyclic anion, a nitrate anion, a hypochlorite anion, a cyanide anion, a cyanate anion, an isocyanate anion, a thiocyanate anion, an isothiocyanate anion, an azide anion, and the like. Examples of a unidentate ligand performing coordination by an unshared electron pair include water, alcohol, phenol, ether, amine, aniline, amide, imide, imine, nitrile, isonitrile, thiol, thioether, a carbonyl compound, a thiocarbonyl compound, sulfoxide, a hetero ring, a carbonic acid, a carboxylic acid, a sulfuric acid, a sulfonic acid, a phosphoric acid, a phosphonic acid, a phosphinic acid, a nitric acid, or ester thereof.

The type and the number of unidentate ligands can be suitably selected according to the compound (A) coordinating with a copper complex.

Specific examples of the unidentate ligands used as the ligands other than the compound (A) are as follows, but there is no limitation thereto. Hereinafter, Me represents a methyl group, Et represents an ethyl group, and Ph represents a phenyl group.

TABLE 1

| | |
|---|---|
| A1-1 | —Cl |
| A1-2 | —Br |
| A1-3 | —F |
| A1-4 | —OH |
| A1-5 | —OMe |
| A1-6 | —OPh |
| A1-7 | —NH$_2$ |
| A1-8 | —NHCOCH$_3$ |
| A1-9 | —NHCOCF$_3$ |
| A1-10 | —NHSO$_2$CH$_3$ |
| A1-11 | —NHSO$_2$CF$_3$ |
| A1-12 | —N(COCH$_3$)$_2$ |
| A1-13 | —N(SO$_2$CF$_3$)$_2$ |
| A1-14 | —SC(=S)CH$_3$ |
| A1-15 | —OP(=O)(OMe)Ph |
| A1-16 | —OS(=O)$_2$CF$_3$ |
| A1-17 | —NMe$_2$ |
| A1-18 | —N(SiMe$_3$)$_2$ |
| A1-19 | —NHPh |

TABLE 1-continued

| | |
|---|---|
| A1-20 | —SPh |
| A1-21 | —OS(=O)(OH)$_2$ |
| A1-22 | —OS(=O)$_2$CH$_3$ |
| A1-23 | —OCOCH$_3$ |
| A1-24 | —OCOPh |
| A1-25 | —OP(=O)(OH)$_2$ |
| A1-26 | —OP(=O)(OPh)$_2$ |
| A1-27 | —OP(=O)Me$_2$ |
| A1-28 | —ONO$_2$ |
| A1-29 | —NCO |
| A1-30 | —OCN |
| A1-31 | —NCS |
| A1-32 | —SCN |
| A1-33 | —CN |
| A1-34 | —N$_3$ |
| A1-35 | *N-methylsuccinimide* |
| A1-36 | *N-methylsaccharin* |
| A1-37 | *N-methylpyrrole* |
| A1-38 | *N-methylpyrazole* |
| A1-39 | *N-methyl-1,2,4-triazole* |
| A1-40 | *1,3-dimethyl-1,2,4-triazole* |
| A1-41 | —OH$_2$ |
| A1-42 | —OHMe |
| A1-43 | —OHPh |
| A1-44 | —NH$_3$ |
| A1-45 | —NEt$_3$ |
| A1-46 | —NH$_2$Ph |
| A1-47 | —NCMe |
| A1-48 | —O=C(CH$_3$)$_2$ |
| A1-49 | —O=S(CH$_3$)$_2$ |
| A1-50 | —SHPh |
| A1-51 | *tetrahydrofuran* |
| A1-52 | *N,N-dimethylformamide* |
| A1-53 | *N-phenyl-N-methyl acetimine* |
| A1-54 | *methoxy cyclohexanone* |
| A1-55 | *N-methylpyridinium* |
| A1-56 | *N-methyl-4-(dimethylamino)pyridinium* |
| A1-57 | *N-methylimidazole* |
| A1-58 | *methyl 2-ethylhexanoate* |
| A1-59 | *methyl pivalate* |
| A1-60 | *methyl trifluoroacetate* |
| A1-61 | *methyl heptafluorobutanoate* |
| A1-62 | *methyl pentafluorobenzoate* |
| A1-63 | *methyl 3,5-dimethoxybenzoate* |
| A1-64 | *methyl 2-(butoxycarbonyl)benzoate* |

TABLE 1-continued

A1-65
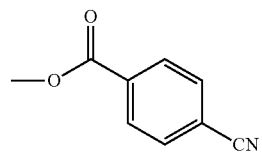

A1-66
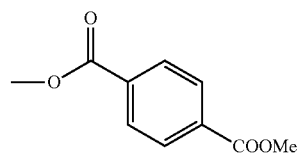

The copper complex used in the present invention may be a cationic complex or an anionic complex in addition to a neutral complex not having an electric charge according to the number of coordination portions performing coordination by anions. In this case, in order to neutralize the electric charge of the copper complex, as necessary, counter ions exist.

In a case where the counter ion is a negative counter ion, for example, the counter ion may be an inorganic anion or an organic anion. Specific examples of the counter ion include a hydroxide ion, a halogen anion (for example, a fluoride ion, a chloride ion, a bromide ion, an iodide ion, and the like), a substituted alkyl carboxylate ion or a non-substituted alkyl carboxylate ion (an acetate ion, a trifluoroacetate ion, and the like), a substituted aryl carboxylate ion or a non-substituted aryl carboxylate ion (a benzoate ion and the like), a substituted alkyl sulfonate ion or a non-substituted alkyl sulfonate ion (a methane sulfonate ion, a trifluoromethanesulfonate ion, and the like), a substituted aryl sulfonate ion or a non-substituted aryl sulfonate ion (for example, a p-toluene sulfonate ion, a p-chlorobenzene sulfonate ion, and the like), an aryl disulfonate ion (for example, a 1,3-benzene disulfonate ion, a 1,5-naphthalene disulfonate ion, a 2,6-naphthalene disulfonate ion, and the like), an alkyl sulfate ion (for example, a methyl sulfate ion and the like), a sulfate ion, a thiocyanate ion, a nitrate ion, a perchlorate ion, a tetrafluoroborate ion, a tetraaryl borate ion, a hexafluorophosphate ion, a picrate ion, an amide ion (including amide substituted with an acyl group or a sulfonyl group), and a methide ion (including methide substituted with an acyl group or a sulfonyl group), and the halogen anion, the substituted alkyl carboxylate ion or the non-substituted alkyl carboxylate ion, the sulfate ion, the nitrate ion, the tetrafluoroborate ion, the tetraaryl borate ion, the hexafluorophosphate ion, the amide ion (including the amide substituted with the acyl group or the sulfonyl group), and the methide ion (including the methide substituted with the acyl group or the sulfonyl group) are preferable.

In a case where the counter ion is a positive counter ion, examples of the counter ion include an inorganic ammonium ion or an organic ammonium ion (for example, a tetraalkyl ammonium ion such as a tetrabutyl ammonium ion, a triethyl benzyl ammonium ion, a pyridinium ion, and the like), a phosphonium ion (for example, a tetraalkyl phosphonium ion such as a tetrabutyl phosphonium ion, an alkyl triphenyl phosphonium ion, a triethyl phenyl phosphonium ion, and the like), an alkali metal ion, or a proton.

In addition, the counter ion may be a metal complex ion, and in particular, the counter ion may be a copper complex, that is, may be a salt of a cationic copper complex and an anionic copper complex.

Here, when the structures of the copper and the compound (A) can be detected from the composition of the present invention, it can be said that a copper complex including the compound (A) as a ligand is formed in the composition of the present invention. As a method of detecting the copper and the compound (A) from the composition of the present invention, inductively coupled plasma (ICP) atomic emission spectrometry is used, for example.

As the copper complex used in the present invention, the following aspects (1) to (5) are used as preferable examples, the aspects (2) to (5) are more preferable, the aspects (3) to (5) are even more preferable, and the aspect (4) or (5) is still more preferable.

(1) Copper complex including one or two compounds having two coordination portions as a ligand (2) Copper complex including a compound having three coordination portions as a ligand (3) Copper complex including a compound having three coordination portions and a compound having two coordination portions as ligands (4) Copper complex including a compound having four coordination portions as a ligand (5) Copper complex including a compound having five coordination portions as a ligand In the aspect (1), the compound having two coordination portions is preferably a compound having two coordination portions performing coordination by an unshared electron pair or a compound having a coordination portion performing coordination by an anion and the coordination portion performing coordination by an unshared electron pair. In a case of including two compounds having two coordination portions as ligands, the compounds as the ligands may be the same as each other or different from each other.

In the aspect (1), the copper complex can further include the unidentate ligand described above. The number of the unidentate ligands can be 0 and can also be 1 to 3. As the type of the unidentate ligand, both of a unidentate ligand performing coordination by an anion and a unidentate ligand performing coordination by an unshared electron pair are preferable. In a case where the compound having two coordination portions is a compound having two coordination portions performing coordination by an unshared electron pair, the unidentate ligand performing coordination by an anion is more preferable from the reason of a strong coordination force, and in a case where the compound having two coordination portions is a compound having a coordination portion performing coordination by an anion and a coordination portion performing coordination by an unshared electron pair, the unidentate ligand performing coordination by an unshared electron pair is more preferable from a viewpoint in which the entire complex does not have an electric charge.

In the aspect (2), the compound having three coordination portions is preferably a compound having a coordination portion performing coordination by an unshared electron pair and more preferably a compound having three coordination portions performing coordination by an unshared electron pair.

In the aspect (2), the copper complex can further include the unidentate ligand described above. The number of the unidentate ligands can be 0. The number of the unidentate ligands can be greater than or equal to 1, is more preferably 1 to 3, even more preferably 1 to 2, and still more preferably 2. As the type of the unidentate ligand, both of a unidentate ligand performing coordination by an anion and a unidentate ligand performing coordination by an unshared electron pair are preferable, and a unidentate ligand performing coordination by an anion is more preferable from the viewpoint described above.

In the aspect (3), the compound having three coordination portions is preferably a compound having a coordination portion performing coordination by an anion and a coordination portion performing coordination by an unshared electron pair and more preferably a compound having two coordination portions performing coordination by an anion and one coordination portion performing coordination by an unshared electron pair. In addition, it is particularly preferable that the two coordination portions performing coordination by an anion are different from each other. The compound having two coordination portions is preferably a compound having a coordination portion performing coordination by an unshared electron pair and more preferably a compound having two coordination portions performing coordination by an unshared electron pair. Among these, a combination in which the compound having three coordination portions is a compound having two coordination portions performing coordination by an anion and one coordination portion performing coordination by an unshared electron pair and the compound having two coordination portions is a compound having two coordination portions performing coordination by an unshared electron pair is particularly preferable.

In addition, in the aspect (3), the copper complex can further include the unidentate ligand described above. The number of the unidentate ligands can be 0 and can also be greater than or equal to 1. The number thereof is more preferably 0.

In the aspect (4), the compound having four coordination portions is preferably a compound having a coordination portion performing coordination by an unshared electron pair, more preferably a compound having two or more coordination portions performing coordination by an unshared electron pair, and even more preferably a compound having four coordination portions performing coordination by an unshared electron pair.

In addition, in the aspect (4), the copper complex can further include the unidentate ligand described above. The number of the unidentate ligands can be 0, can be greater than or equal to 1, or can be greater than or equal to 2. The number thereof is preferably 1. As the type of the unidentate ligand, both of a unidentate ligand performing coordination by an anion and a unidentate ligand performing coordination by an unshared electron pair are preferable.

In the aspect (5), the compound having five coordination portions is preferably a compound having a coordination portion performing coordination by an unshared electron pair, more preferably a compound having two or more coordination portions performing coordination by an unshared electron pair, and even more preferably a compound having five coordination portions performing coordination by an unshared electron pair.

In addition, in the aspect (5), the copper complex can further include the unidentate ligand described above. The number of the unidentate ligands can be 0 and can also be greater than or equal to 1. The number of the unidentate ligands is preferably 0.

<<Compound (A) Having at Least Two Coordination Portions>>

Next, the compound (A) formed of ligands of the copper complex will be described.

The compound (A) has at least two coordination portions in one molecule, or may have three or more coordination portions. Examples of the coordination portion include a coordination portion performing coordination by an anion, a coordination atom performing coordination by an unshared electron pair, and the like. The compound (A) may have only two or more coordination portions performing coordination by an anion, may have only two or more coordination portions performing coordination by an unshared electron pair, or may have one or more of each of a coordination portion performing coordination by an anion and a coordination portion performing coordination by an unshared electron pair, as the coordination portions.

The aspect in which the number of coordination portions is three includes a case of having three coordination portions performing coordination by an anion, a case of having two coordination portions performing coordination by an anion and one coordination portion performing coordination by an unshared electron pair, a case of having one coordination portion performing coordination by an anion and two coordination portions performing coordination by an unshared electron pair, and a case of having three coordination portions performing coordination by an unshared electron pair.

The aspect in which the number of coordination portions is four includes a case of having four coordination portions performing coordination by an anion, a case of having three coordination portions performing coordination by an anion and one coordination portion performing coordination by an unshared electron pair, a case of having two coordination portions performing coordination by an anion and two coordination portions performing coordination by an unshared electron pair, a case of having one coordination portion performing coordination by an anion and three coordination portion performing coordination by an unshared electron pair, and a case of having four coordination portions performing coordination by an unshared electron pair.

The aspect in which the number of coordination portions is five includes a case of having five coordination portions performing coordination by an anion, a case of having four coordination portions performing coordination by an anion and one coordination portion performing coordination by an unshared electron pair, a case of having three coordination portions performing coordination by an anion and two coordination portions performing coordination by an unshared electron pair, a case of having two coordination portions performing coordination by an anion and three coordination portions performing coordination by an unshared electron pair, a case of having one coordination portion performing coordination by an anion and four coordination portions performing coordination by an unshared electron pair, and a case of having five coordination portions performing coordination by an unshared electron pair.

The anion in the compound (A) may be an anion which can coordinate with a copper atom, and an oxygen anion, a nitrogen anion, or a sulfur anion is preferable.

It is preferable that the coordination portion performing coordination by an anion is at least one type selected from the following monovalent functional group Group (AN-1) or divalent functional group Group (AN-2). Wave lines in the following structural formulas are bonding sites with an atomic group configuring the compound (A).

Group (AN-1)

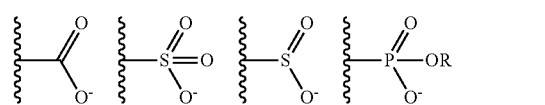

-continued

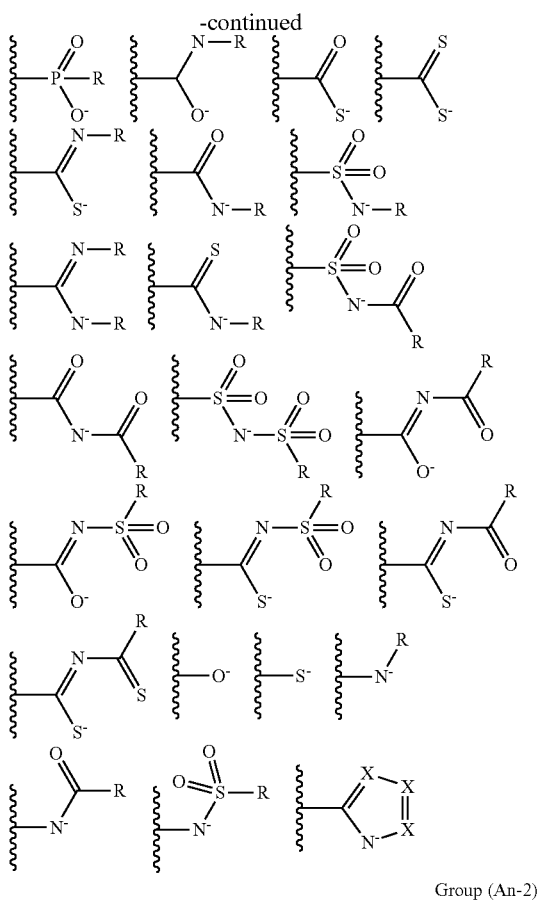

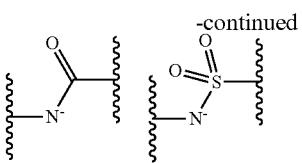

Group (An-2)

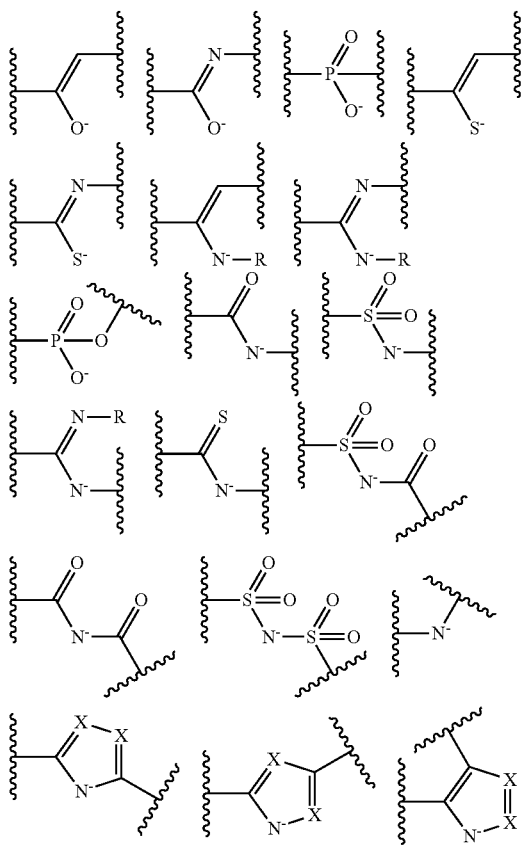

In the coordination portions performing coordination by an anion, it is preferable that X represents N or CR and R represents a hydrogen atom, an alkyl group, an alkenyl group, an alkynyl group, an aryl group, or a heteroaryl group.

The alkyl group may be a linear alkyl group, a branched alkyl group, or a cyclic alkyl group, and the linear alkyl group is preferable. The number of carbon atoms of the alkyl group is preferably 1 to 10, is more preferably 1 to 6, and is even more preferably 1 to 4. Examples of the alkyl group include a methyl group. The alkyl group may have a substituent. Examples of the substituent include a halogen atom, a carboxyl group, and a heterocyclic group. The heterocyclic group as the substituent may be a monocyclic group or a polycyclic group, and may be an aromatic group or a non-aromatic group. The number of hetero atoms configuring a hetero ring is preferably 1 to 3, and is more preferably 1 or 2. The hetero atom configuring the hetero ring is preferably a nitrogen atom. In a case where the alkyl group has the substituent, the substituent may further have a substituent.

The alkenyl group may be a linear alkenyl group, a branched alkenyl group, or a cyclic alkenyl group, and the linear alkenyl group is preferable. The number of carbon atoms of the alkenyl group is preferably 1 to 10 and is more preferably 1 to 6. The alkenyl group may be a non-substituted alkenyl group or may have a substituent. Examples of the substituent include the substituents described above.

The alkynyl group may be a linear alkynyl group, a branched alkynyl group, or a cyclic alkynyl group, and the linear alkynyl group is preferable. The number of carbon atoms of the alkynyl group is preferably 1 to 10 and is more preferably 1 to 6. The alkynyl group may be a non-substituted alkynyl group or may have a substituent. Examples of the substituent include the substituents described above.

The aryl group may be a monocyclic aryl group, or may be a polycyclic aryl group, and the monocyclic aryl group is preferable. The number of carbon atoms of the aryl group is preferably 6 to 18, is more preferably 6 to 12, and is even more preferably 6. The aryl group may be a non-substituted aryl group or may have a substituent. Examples of the substituent include the substituents described above.

The heteroaryl group may be a monocyclic heteroaryl group, or may be a polycyclic heteroaryl group. The number of hetero atoms configuring the heteroaryl group is preferably 1 to 3. The hetero atom configuring the heteroaryl group is preferably a nitrogen atom, a sulfur atom, or an oxygen atom. The number of carbon atoms of the heteroaryl group is preferably 6 to 18, and is more preferably 6 to 12. The heteroaryl group may be a non-substituted heteroaryl group or may have a substituent. Examples of the substituent include the substituents described above.

In the compound (A), the coordination atom performing coordination by an unshared electron pair is preferably an oxygen atom, a nitrogen atom, a sulfur atom, or a phosphorus atom, more preferably an oxygen atom, a nitrogen atom, or a sulfur atom, and even more preferably oxygen atom or a nitrogen atom, and particularly preferably a nitrogen atom.

In the compound (A), in a case where the coordination atom performing coordination by an unshared electron pair is a nitrogen atom, an atom adjacent to the nitrogen atom is preferably a carbon atom or a nitrogen atom and more preferably a carbon atom.

The coordination atom performing coordination by an unshared electron pair is preferably contained in a ring or in at least one type of a partial structure selected from the following monovalent functional group Group (UE-1), divalent functional group Group (UE-2), and trivalent functional group Group (UE-3). Wave lines in the following structural formulas are bonding sites with an atomic group configuring the compound (A).

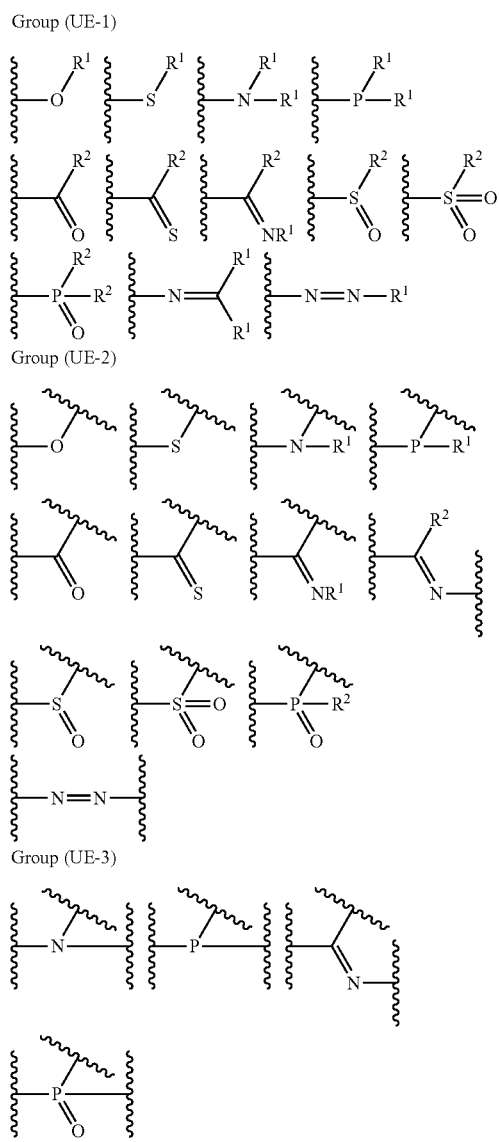

Group (UE-1)

Group (UE-2)

Group (UE-3)

In Groups (UE-1) to (UE-3), $R^1$ represents a hydrogen atom, an alkyl group, an alkenyl group, an alkynyl group, an aryl group, or a heteroaryl group, and $R^2$ represents a hydrogen atom, an alkyl group, an alkenyl group, an alkynyl group, an aryl group, a heteroaryl group, an alkoxy group, an aryloxy group, a heteroaryloxy group, an alkyl thio group, an aryl thio group, a heteroaryl thio group, an amino group, or an acyl group.

The coordination atom performing coordination by an unshared electron pair may be contained in a ring. In a case where the coordination atom performing coordination by an unshared electron pair is contained in the ring, the ring containing the coordination atom performing coordination by an unshared electron pair may be a monocyclic ring, or may be a polycyclic ring, and may be an aromatic ring or a non-aromatic ring. The ring containing the coordination atom performing coordination by an unshared electron pair is preferably a 5-membered ring to 12-membered ring and more preferably a 5-membered ring to a 7-membered ring.

The ring containing a coordination atom performing coordination by an unshared electron pair may have a substituent. Examples of the substituent include a linear alkyl group, a branched alkyl group, or a cyclic alkyl group having 1 to 10 carbon atoms, an aryl group having 6 to 12 carbon atoms, a halogen atom, a silicon atom, an alkoxy group having 1 to 12 carbon atoms, an acyl group having 2 to 12 carbon atoms, an alkyl thio group having 1 to 12 carbon atoms, a carboxyl group, and the like.

In a case where the ring containing a coordination atom performing coordination by an unshared electron pair includes a substituent, the substituent may further have a substituent. Examples thereof include a group formed of a ring containing a coordination atom performing coordination by an unshared electron pair, a group having at least one type of a partial structure selected from Groups (UE-1) to (UE-3) described above, an alkyl group having 2 to 12 carbon atoms, an acyl group having 1 to 12 carbon atoms, a hydroxy group, and the like.

In a case where the coordination atom performing coordination by an unshared electron pair is contained in a partial structure represented by Groups (UE-1) to (UE-3), $R^1$ represents a hydrogen atom, an alkyl group, an alkenyl group, an alkynyl group, an aryl group, or a heteroaryl group, $R^2$ represents a hydrogen atom, an alkyl group, an alkenyl group, an alkynyl group, an aryl group, a heteroaryl group, an alkoxy group, an aryloxy group, a heteroaryloxy group, an alkyl thio group, an aryl thio group, a heteroaryl thio group, an amino group, or an acyl group.

An alkyl group, an alkenyl group, an alkynyl group, an aryl group, and a heteroaryl group are identical to the alkyl group, the alkenyl group, the alkynyl group, the aryl group, and the heteroaryl group described with the coordination portion performing coordination by an anion, and the preferred range thereof is also identical to that of these groups.

The number of carbon atoms of the alkoxy group is preferably 1 to 12 and more preferably 3 to 9.

The number of carbon atoms of the aryloxy group is preferably 6 to 18 and more preferably 6 to 12.

The heteroaryloxy group may be a monocyclic heteroaryloxy group or may be a polycyclic heteroaryloxy group. A heteroaryl group configuring the heteroaryloxy group is identical to the heteroaryl group described with the coordination portion performing coordination by an anion, and the preferred range thereof is also identical to that of the heteroaryl group.

The number of carbon atoms of the alkyl thio group is preferably 1 to 12 and more preferably 1 to 9.

The number of carbon atoms of the aryl thio group is preferably 6 to 18 and more preferably 6 to 12.

The heteroaryl thio group may be a monocyclic heteroaryl thio group, or may be a polycyclic heteroaryl thio group. A heteroaryl group configuring the heteroaryl thio group is identical to the heteroaryl group described with the coordination portion performing coordination by an anion, and the preferred range thereof is also identical to that of the heteroaryl group.

The number of carbon atoms of the acyl group is preferably 2 to 12 and more preferably 2 to 9.

In a case where the compound (A) has a coordination portion performing coordination by an anion and a coordination portion performing coordination by an unshared electron pair in one molecule, the number of atoms linking the coordination portion performing coordination by an anion and the coordination portion performing coordination by an unshared electron pair to each other is preferably 1 to 6 and more preferably 1 to 3. According to such a configuration, a structure of a copper complex is more easily distorted, and thus, a color valency can be further improved and the molar light absorption coefficient is easily increased while increasing visible light transmittance.

The type of the atoms linking the coordination portion performing coordination by an anion and the coordination portion performing coordination by an unshared electron pair to each other may be one type or two or more types. A carbon atom or a nitrogen atom is preferable.

In the following exemplified compounds, in a case where coordination with copper ion is performed by a carboxylate anion obtained due to dissociating of protons of carboxylic acid as a ligand, the anion is an oxygen anion, the coordination atom performing coordination by an unshared electron pair is a nitrogen atom, and the atom linking the anion and the coordination atom performing coordination by an unshared electron pair to each other is a carbon atom. The number of atoms linking the anion and the coordination atom performing coordination by an unshared electron pair to each other is 2. In a case where coordination with the copper ion is performed in a nonionic state without the dissociating of protons of the exemplified compound, it is considered that coordination is performed by two unshared electron pairs which are an oxygen atom and a nitrogen atom on carboxylic acid, but the exemplified compound rarely has such a coordination format.

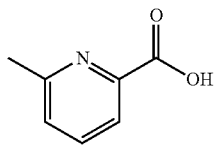

In a case where the compound (A) has two or more coordination atoms performing coordination by an unshared electron pair in one molecule, the number of coordination atoms performing coordination by an unshared electron pair may be greater than or equal to 3, is preferably 2 to 5, and is more preferably 4.

The number of atoms linking the coordination atoms performing coordination by an unshared electron pair to each other is preferably 1 to 6, more preferably 1 to 3, even more preferably 2 to 3, and particularly preferably 3. According to such a configuration, a structure of a copper complex is more easily distorted, and thus, a color valency can be further improved.

The type of the atom linking the coordination atoms performing coordination by an unshared electron pair to each other may be one type or two or more types. The atom linking the coordination atoms performing coordination by an unshared electron pair to each other is preferably a carbon atom.

The compound (A) is also preferably represented by the following General Formulas (IV-1) to (IV-14). For example, in a case where the compound (A) is a compound having four coordination portions, compounds represented by the following Formulas (IV-3), (IV-6), (IV-7), and (IV-12) are preferable, and a compound represented by Formula (IV-12) is more preferable from the reason of more strongly performing coordination in the metal center and easily forming a stable pentacoordinate complex having high heat resistance. $X^{33}$ to $X^{35}$ in the compound represented by Formula (IV-12) are preferably at least one type selected from Group (UE-1). $X^{57}$ preferably represents at least one type selected from Group (UE-3).

For example, in a case where the compound (A) is a compound having five coordination portions, compounds represented by the following Formulas (IV-4), (IV-8) to (IV-11), (IV-13), and (IV-14) are preferable, and compounds represented by Formulas (IV-9) to (IV-10), (IV-13), and (IV-14) are more preferable from the reason of more strongly performing coordination in the metal center and easily forming a stable pentacoordinate complex having high heat resistance, and a compound represented by Formula (IV-13) is particularly preferable. $X^{36}$ and $X^{37}$ in the compound represented by Formula (IV-13) are preferably at least one type selected from Group (UE-1). $X^{56}$ preferably represents at least one type selected from Group (UE-2). $X^{58}$ preferably represents at least one type selected from Group (UE-3).

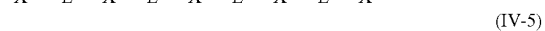
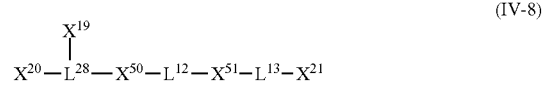
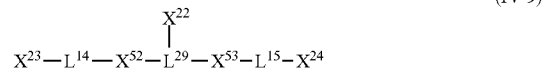

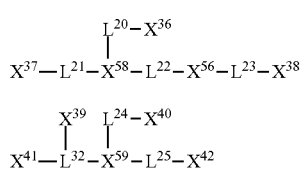

(IV-13)

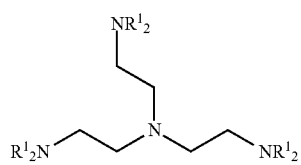

(IV-14)

In General Formulas (IV-1) to (IV-14), $X^1$ to $X^{59}$ each independently represent a coordination portion, $L^1$ to $L^{25}$ each independently represent a single bond or a divalent linking group, $L^{26}$ to $L^{32}$ each independently represent a trivalent linking group, and $L^{33}$ and $L^{34}$ each independently represent a tetravalent linking group.

$X^1$ to $X^{42}$ each independently preferably represent at least one type selected from a group formed of a ring containing a coordination atom performing coordination by an unshared electron pair, or Group (AN-1) or Group (UE-1) described above.

$X^{43}$ to $X^{56}$ each independently preferably represent at least one type selected from a group formed of a ring containing a coordination atom performing coordination by an unshared electron pair, or Group (AN-2) or Group (UE-2) described above.

$X^{57}$ to $X^{59}$ each independently preferably represent at least one type selected from Group (UE-3) described above.

$L^1$ to $L^{25}$ each independently represent a single bond or a divalent linking group. As the divalent linking group, an alkylene group having 1 to 12 carbon atoms, an arylene group having 6 to 12 carbon atoms, —SO—, —O—, —SO$_2$—, or a group formed of a combination thereof is preferable, and an alkylene group having 1 to 3 carbon atoms, a phenylene group, —SO$_2$—, or a group formed of a combination thereof is more preferable.

$L^{26}$ to $L^{32}$ each independently represent a trivalent linking group. As the trivalent linking group, a group obtained by removing one hydrogen atom from the divalent linking group described above is used.

$L^{33}$ and $L^{34}$ each independently represent a tetravalent linking group. As the tetravalent linking group, a group obtained by removing two hydrogen atoms from the divalent linking group described above is used.

The compound represented by Formula (IV-12) is more preferably a compound represented by the following Formula (IV-12').

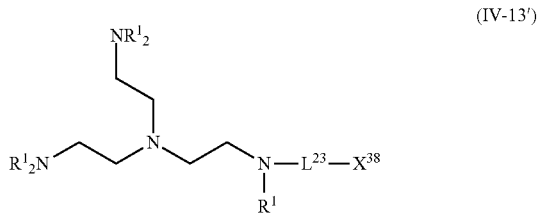

(IV-12')

$R^1$ is identical to $R^1$ of Groups (UE-1) to (UE-3) and represents a hydrogen atom, an alkyl group, an alkenyl group, an alkynyl group, an aryl group, or a heteroaryl group, and $R^2$ represents a hydrogen atom, an alkyl group, an alkenyl group, an alkynyl group, an aryl group, a heteroaryl group, an alkoxy group, an aryloxy group, a heteroaryloxy group, an alkyl thio group, an aryl thio group, a heteroaryl thio group, an amino group, or an acyl group. Both $R^1$'s may be the same as each other or different from each other.

The compound represented by Formula (IV-13) is more preferably a compound represented by the following General Formula (IV-13').

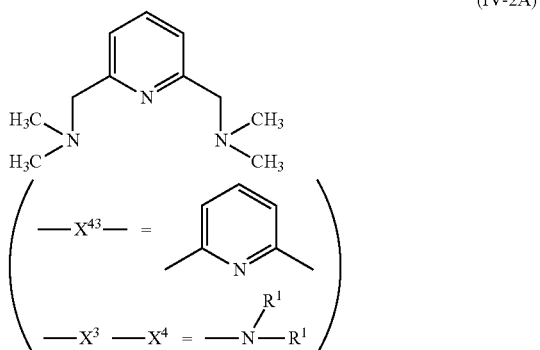

(IV-13')

$R^1$ is identical to $R^1$ of Groups (UE-1) to (UE-3) and represents a hydrogen atom, an alkyl group, an alkenyl group, an alkynyl group, an aryl group, or a heteroaryl group, and $R^2$ represents a hydrogen atom, an alkyl group, an alkenyl group, an alkynyl group, an aryl group, a heteroaryl group, an alkoxy group, an aryloxy group, a heteroaryloxy group, an alkyl thio group, an aryl thio group, a heteroaryl thio group, an amino group, or an acyl group. Both $R^1$'s may be the same as each other or different from each other. $L^{23}$ and $X^{38}$ are identical to $L^{23}$ and $X^{38}$ of Formula (IV-13).

Here, R in Groups (AN-1) and (AN-2) and $R^1$ in Groups (UE-1) to (UE-3) may form rings by linking R's, $R^1$'s, or R and $R^1$ to each other. For example, as a specific example of General Formula (IV-2), the following compound (IV-2A) is used. $X^3$, $X^4$, and $X^{43}$ are groups shown below, $L^2$ and $L^3$ are a methylene group, $R^1$ is a methyl group, and $R^1$'s may be linked to each other to form a ring and form (IV-2B) or (IV-2C).

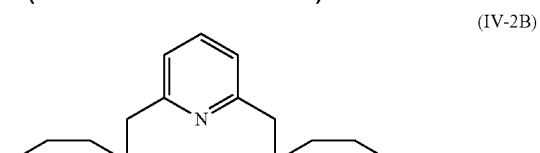

(IV-2A)

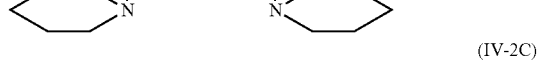

(IV-2B)

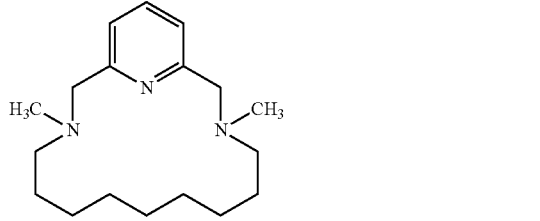

(IV-2C)

In the compound (A), it is preferable that a π conjugated system such as an aromatic group is not linked to have plural bonds, in order to improve visible light transmittance.

The compound (A) is preferably a compound including a 5-membered ring or a 6-membered ring, and it is also preferable that a coordination atom performing coordination by a unshared electron pair configures a 5-membered ring or a 6-membered ring.

The coordination atom performing coordination by an unshared electron pair included in the compound (A) is also preferably a nitrogen atom. In addition, an atom adjacent to the nitrogen atom as the coordination atom performing coordination by an unshared electron pair included in the compound (A) is a carbon atom, and the carbon atom also preferably includes a substituent. According to such a configuration, a structure of a copper complex is more easily distorted, and thus, a color valency can be further improved. The substituent is identical to the substituent which may include a ring containing the coordination atom performing coordination by an unshared electron pair described above, and an alkyl group having 1 to 30 carbon atoms, an aryl group having 6 to 30 carbon atoms, an carboxyl group, an alkoxy group having 1 to 12 carbon atoms, an acyl group having 1 to 12 carbon atoms, an alkyl thio group having 1 to 12 carbon atoms, and a halogen atom are preferable. The alkyl group, the aryl group, the carboxyl group, and the halogen atom are particularly preferable.

A molecular weight of the compound (A) is preferably 50 to 1,000 and more preferably 50 to 500. When the molecular weight thereof is in the range described above, a molecular weight of a complex becomes a small value and an effect of increasing a gram light absorption coefficient is obtained. In the present invention, the molecular weight of the compound (A) is a theoretical value obtained from a structural formula.

Specific examples of the compound (A) include compounds described below and salts (for example, metal salts (alkali metal salts) of sodium or the like) of the compounds described below, but are not limited thereto.

Examples of the compound having two coordination portions include compounds shown in A2-1 to A2-240 described below. Examples of the compound having three coordination portions include compounds shown in A3-1 to A3-142 described below. Examples of the compound having four coordination portions include compounds shown in A4-1 to A4-220 described below. Examples of the compound having five coordination portions include compounds shown in A5-1 to A5-37 described below. All of the compounds shown below are compounds which do not have a maximum absorption wavelength in a wavelength range of 400 to 600 nm.

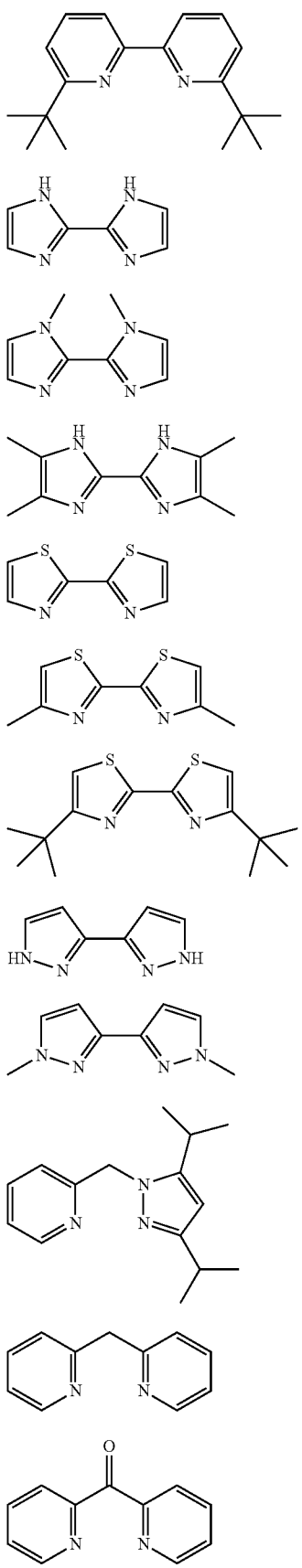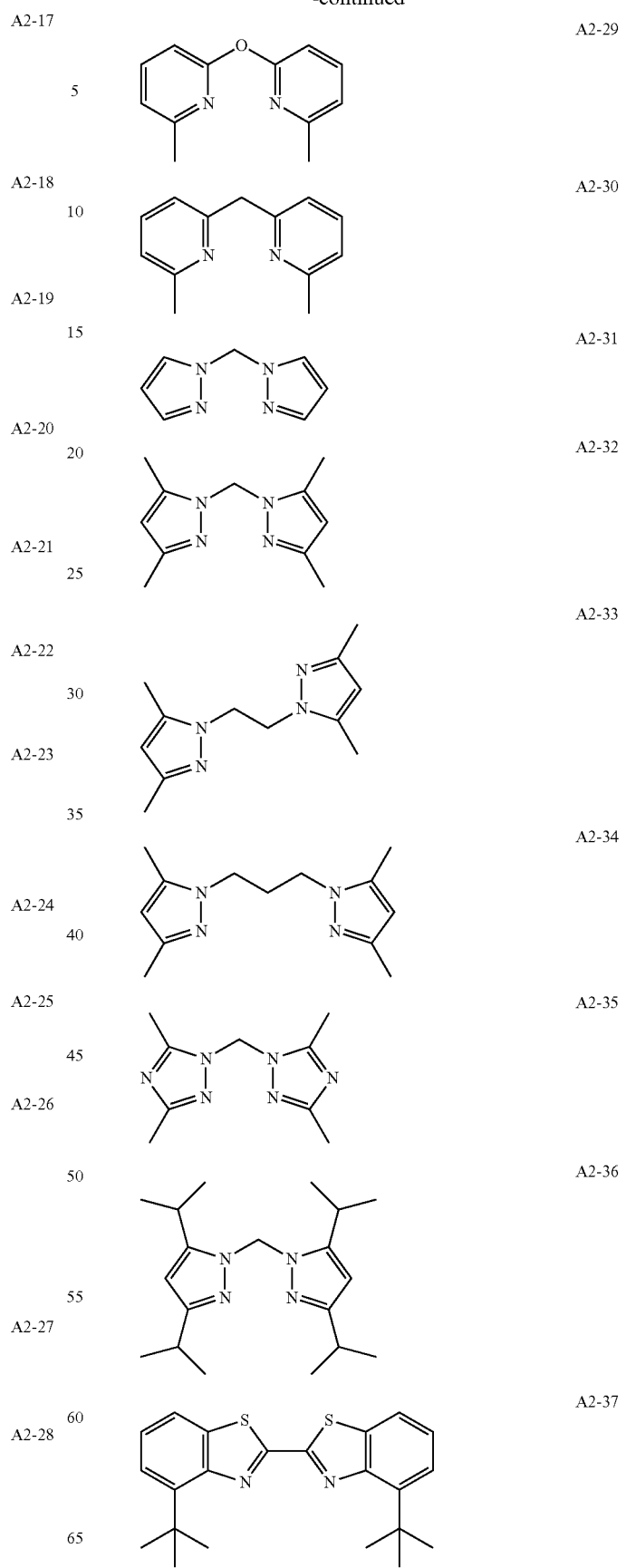

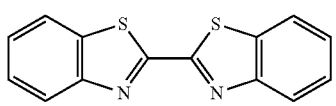
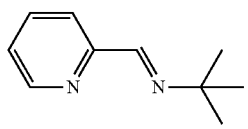
A2-38
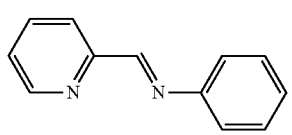
A2-39
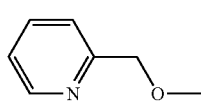
A2-40
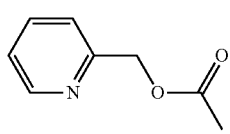
A2-41
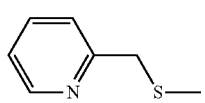
A2-42
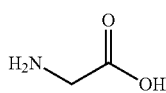
A2-43
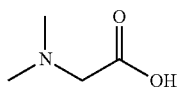
A2-44
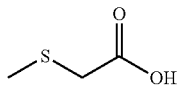
A2-45
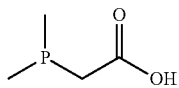
A2-46
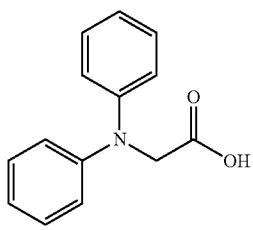
A2-47
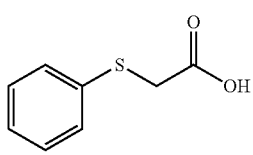
A2-48
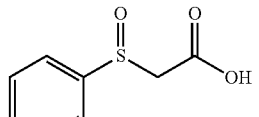
A2-50
A2-51
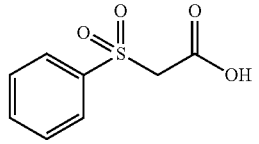
A2-52
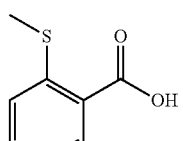
A2-53
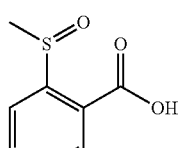
A2-54
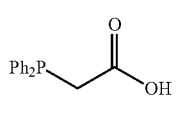
A2-55
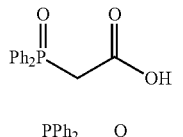
A2-56
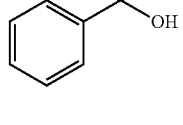
A2-57
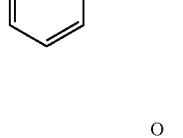
A2-58
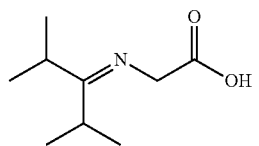
A2-59

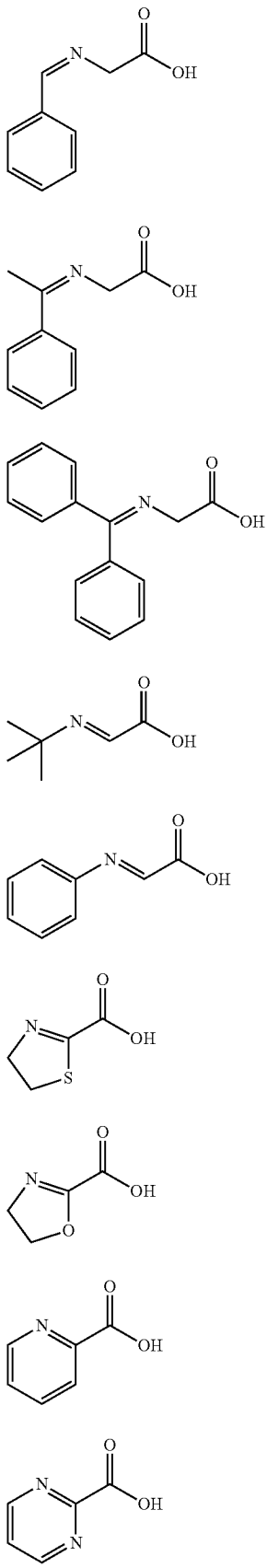
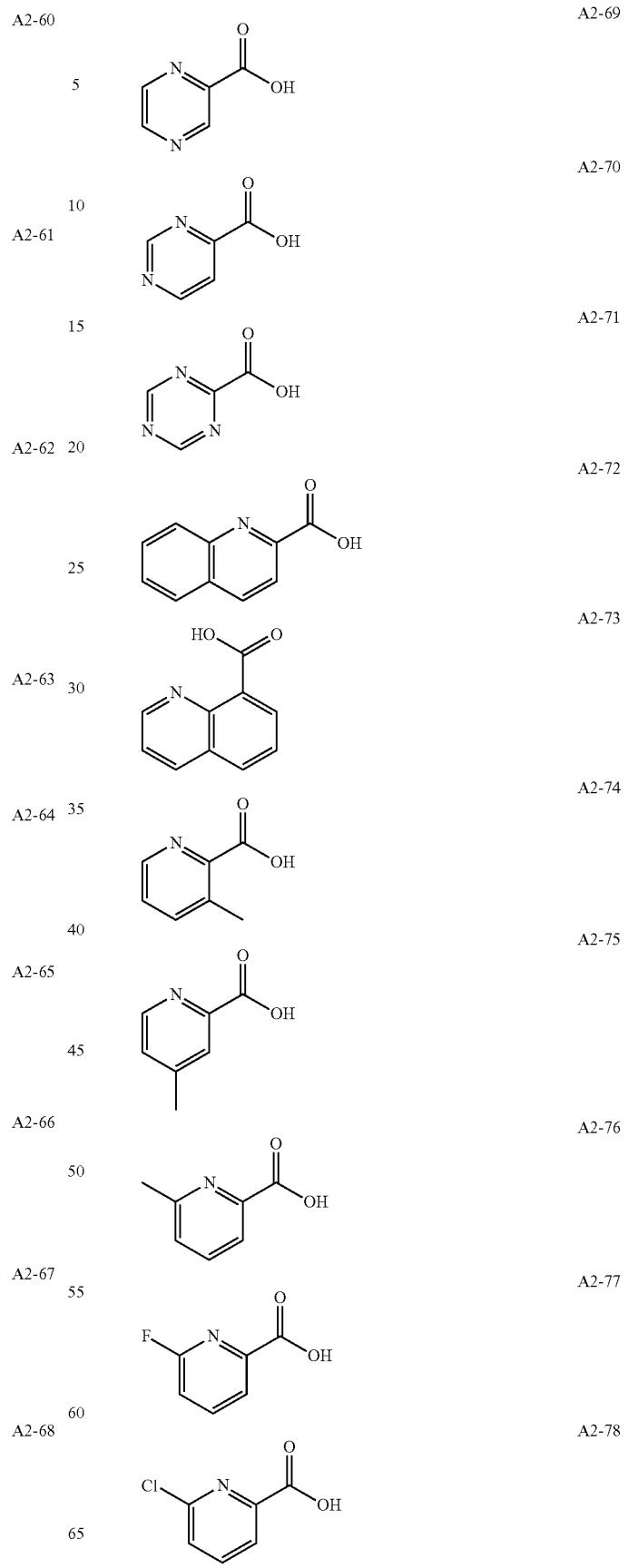

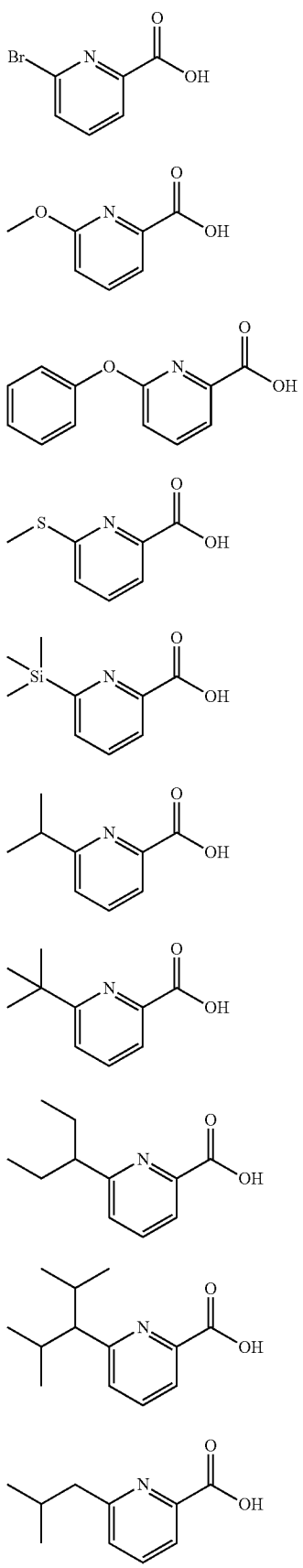
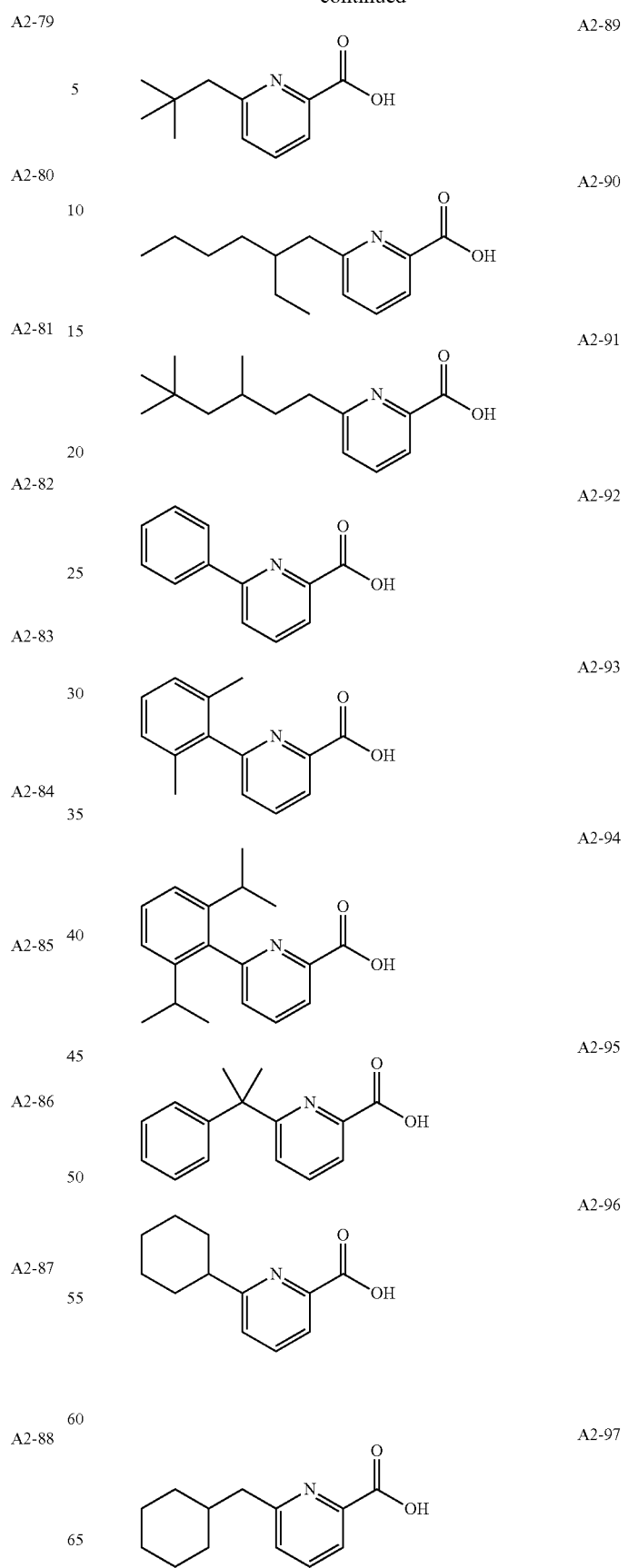

-continued
A2-98 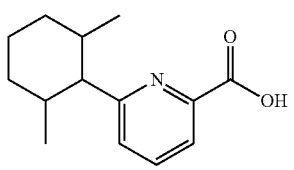
A2-99 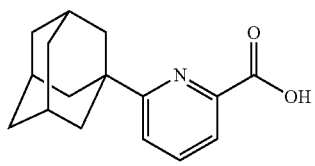
A2-100 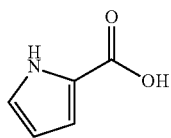
A2-101 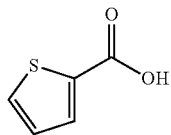
A2-102 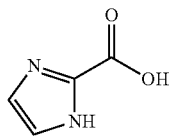
A2-103 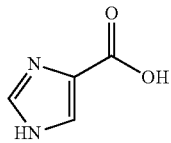
A2-104 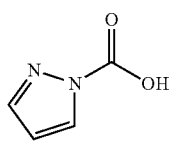
A2-105 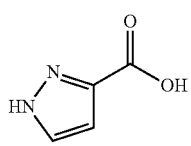
A2-106 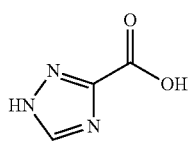
A2-107 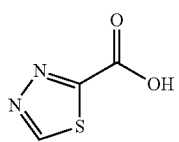
-continued
A2-108 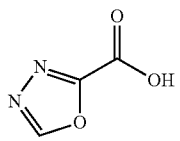
A2-109 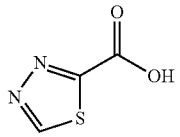
A2-110 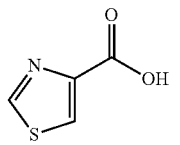
A2-111 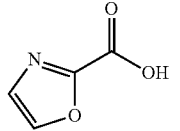
A2-112 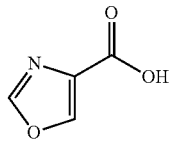
A2-113 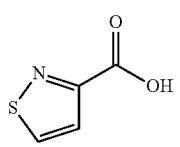
A2-114 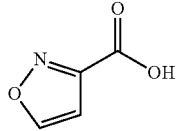
A2-115 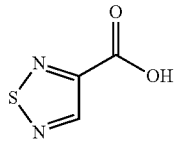
A2-116 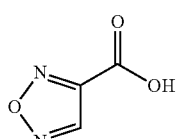
A2-117 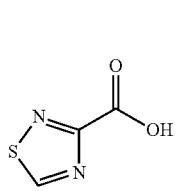

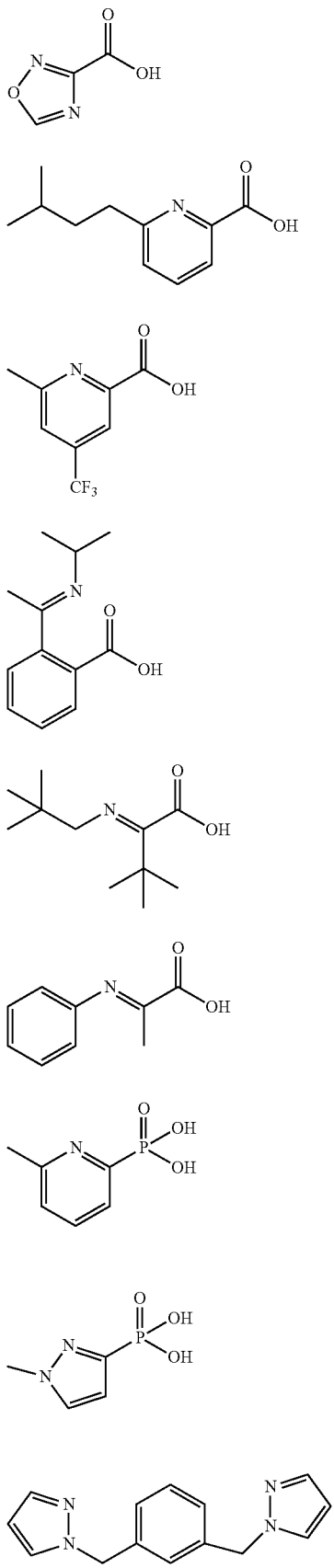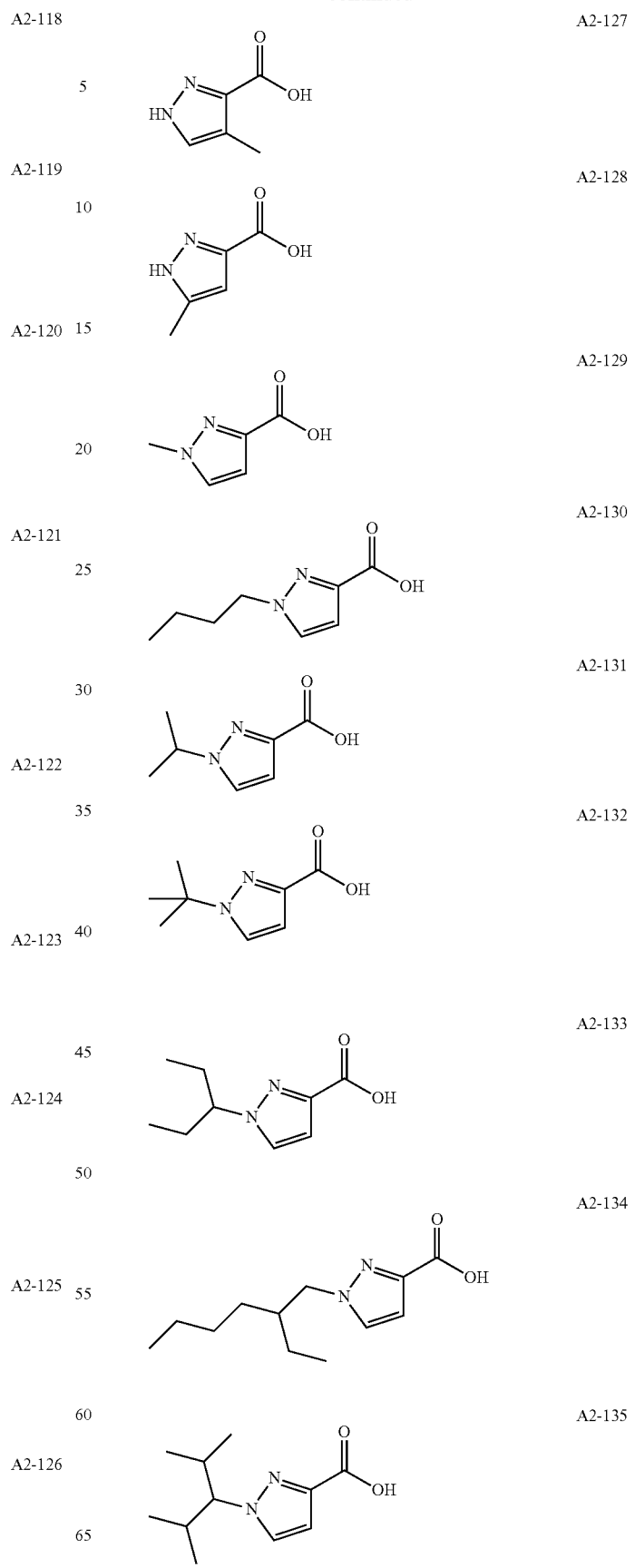

A2-136 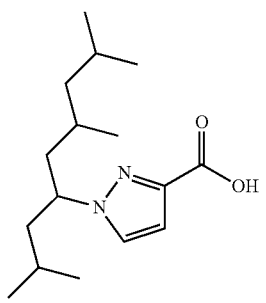
A2-137 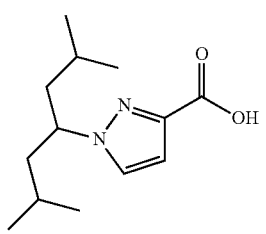
A2-138 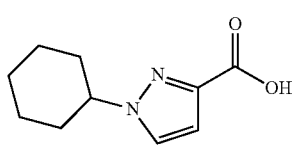
A2-139 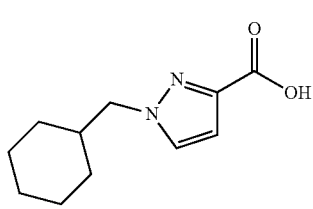
A2-140 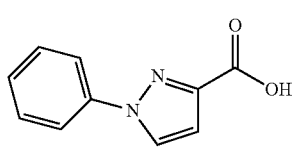
A2-141 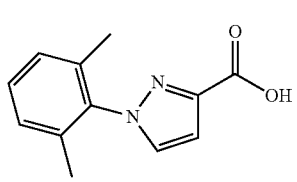
A2-142 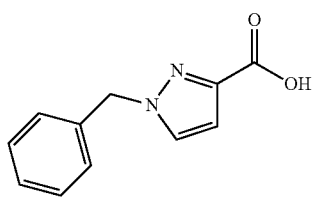
A2-143 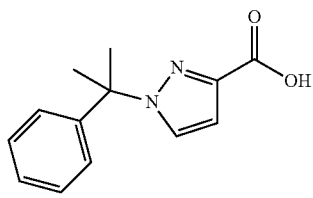
A2-144 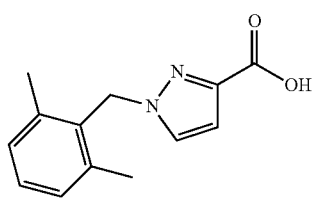
A2-145 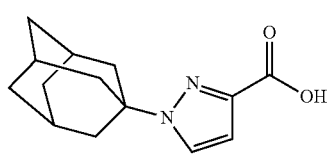
A2-146 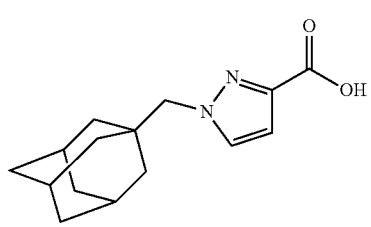
A2-147 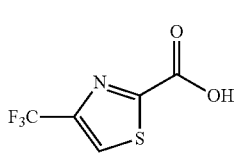
A2-148 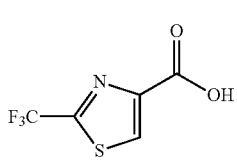
A2-149 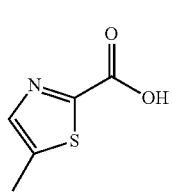
A2-150 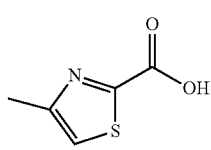
A2-151 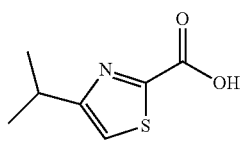
A2-152 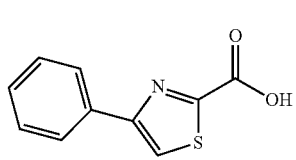

A2-153 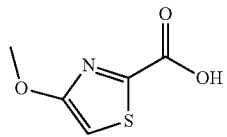
A2-154 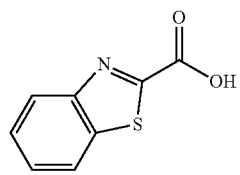
A2-155 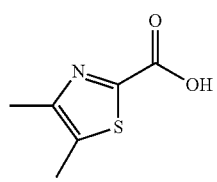
A2-156 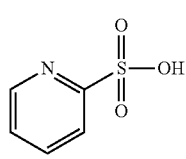
A2-157 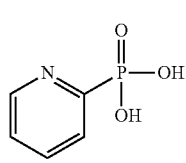
A2-158 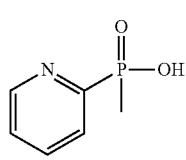
A2-159 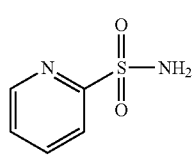
A2-160 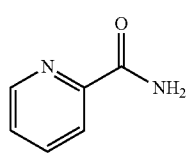
A2-161 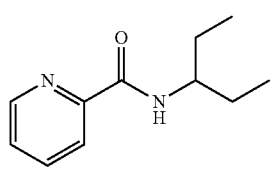
A2-162 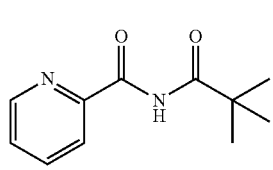
A2-163 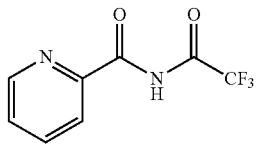
A2-164 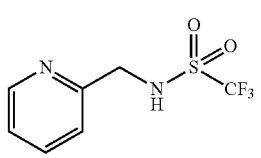
A2-165 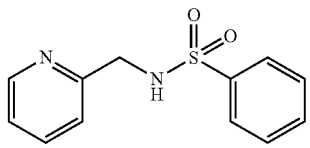
A2-166 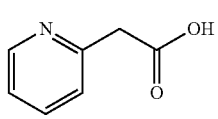
A2-167 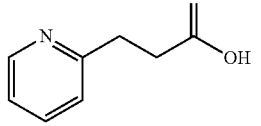
A2-168 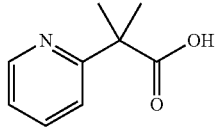
A2-169 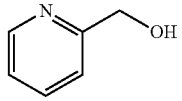
A2-170 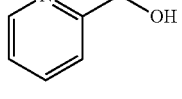
A2-171 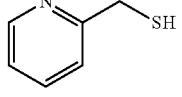
A2-172 
A2-173 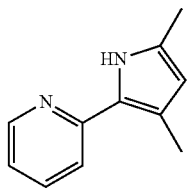

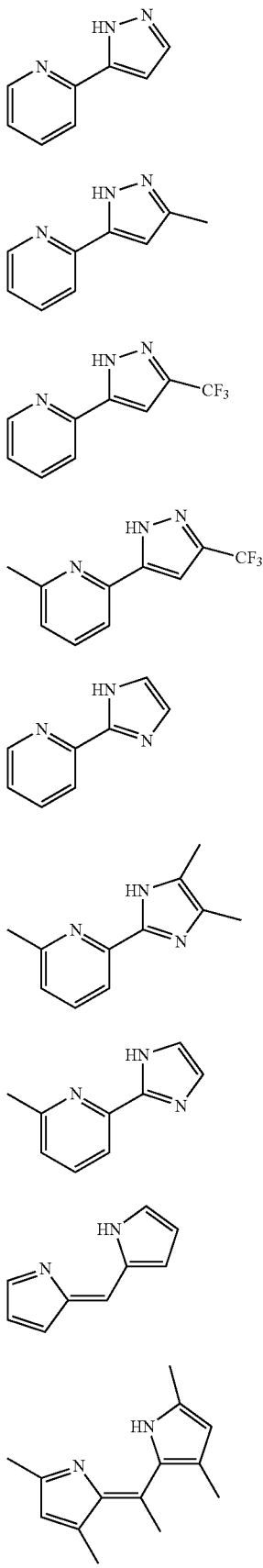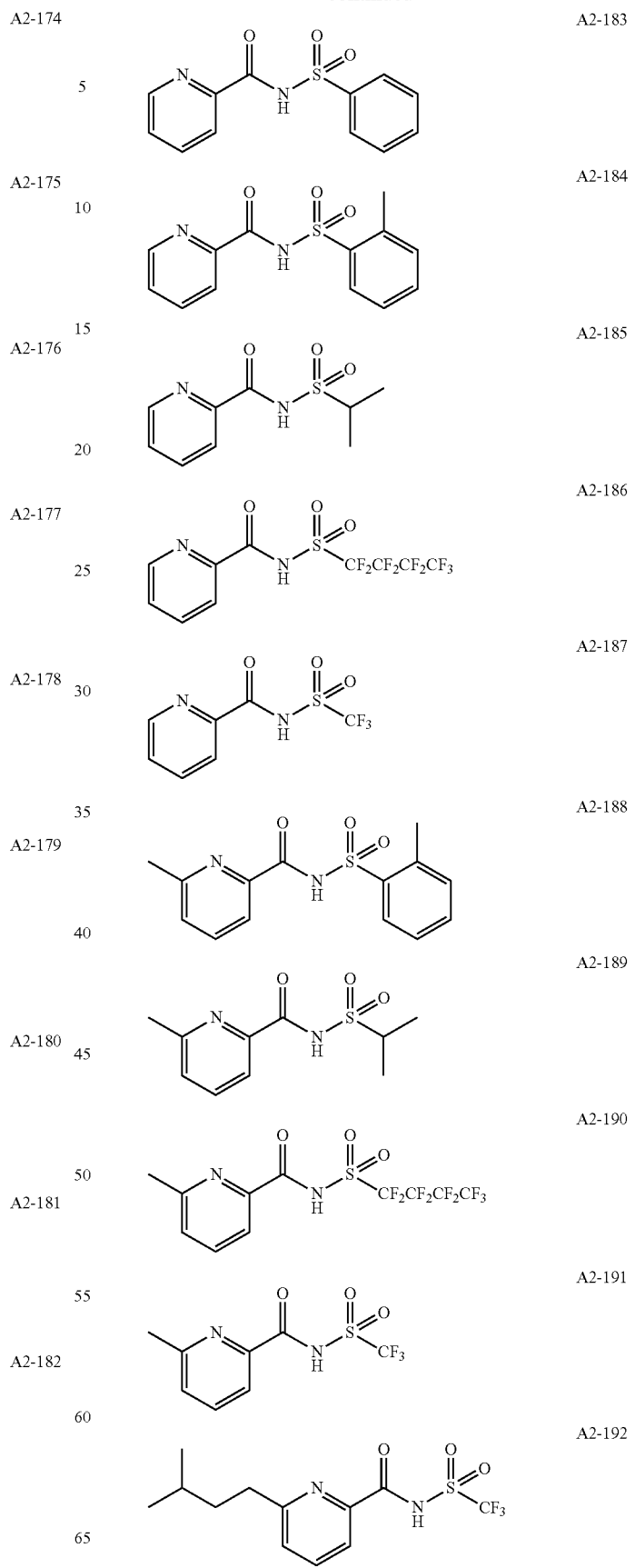

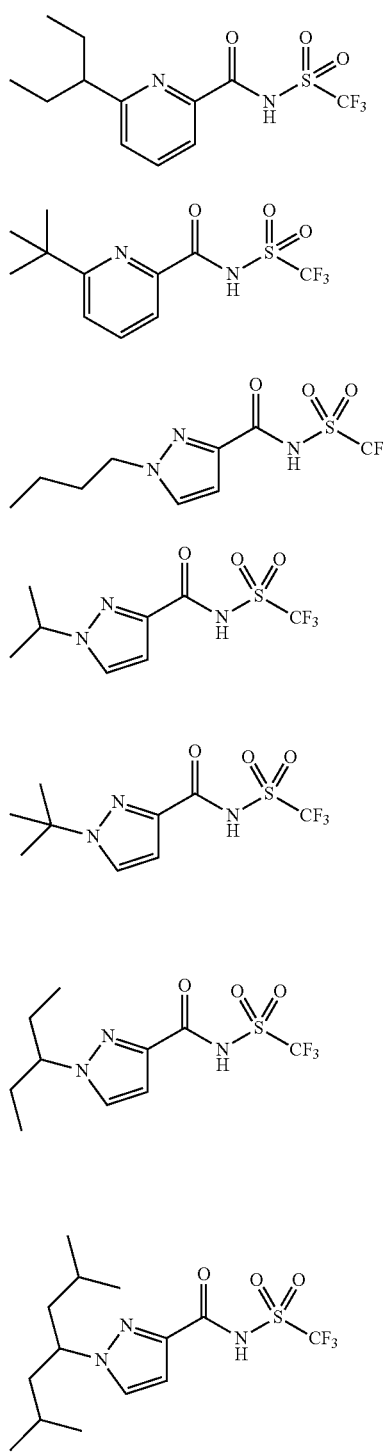
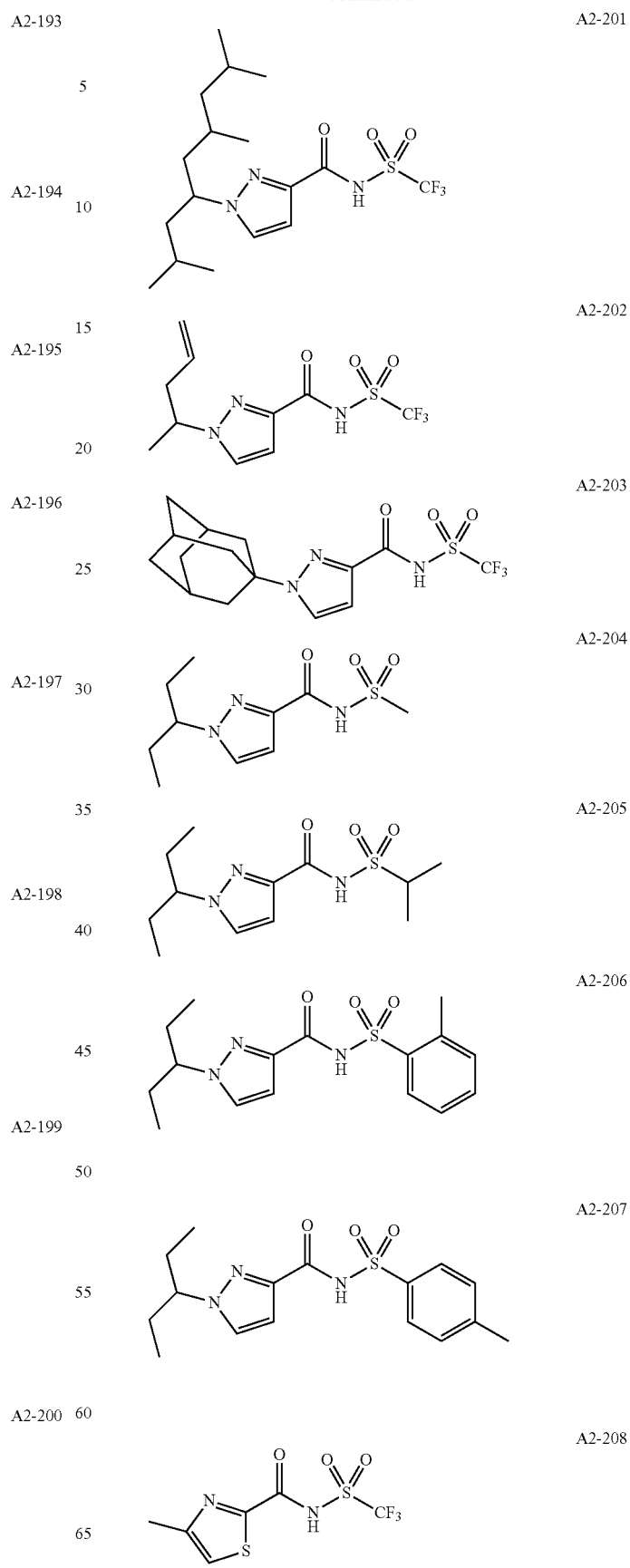

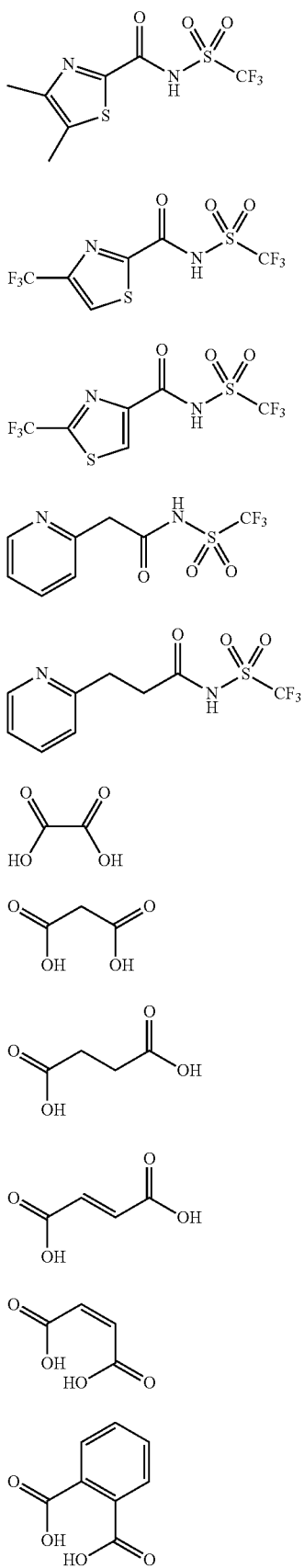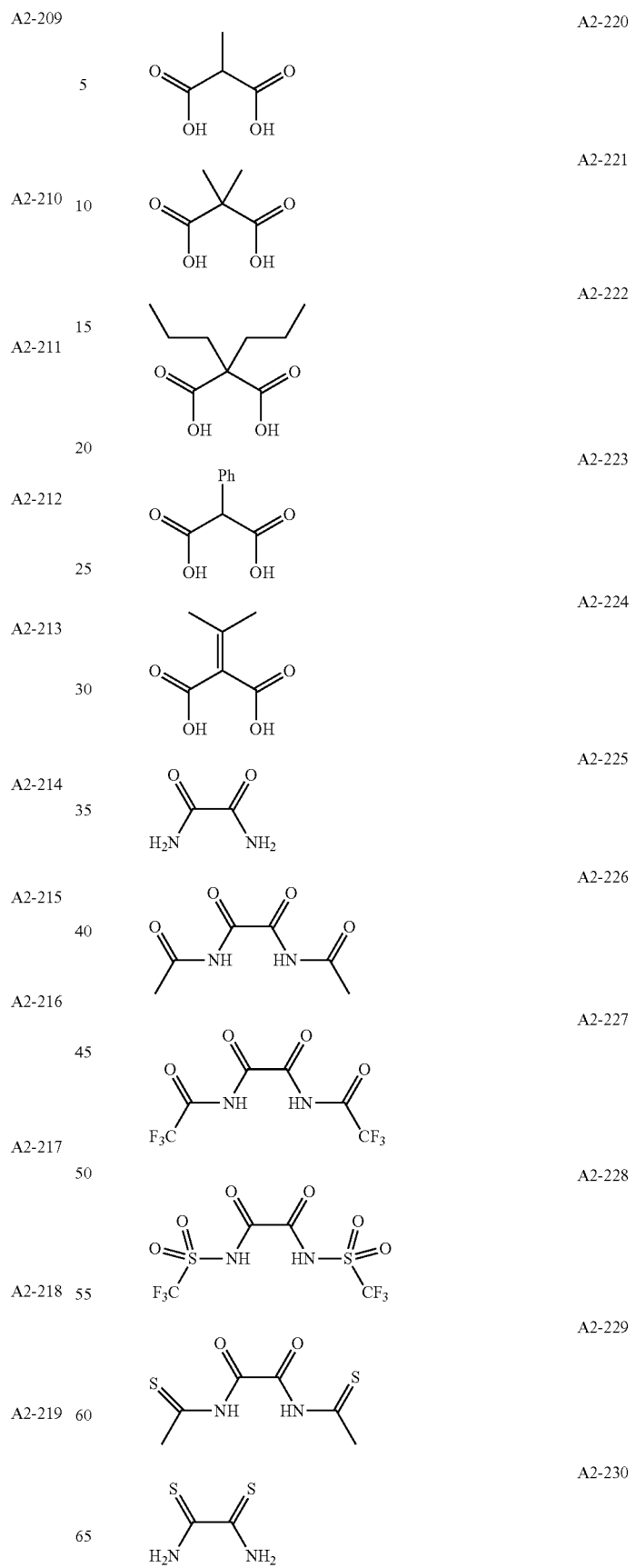

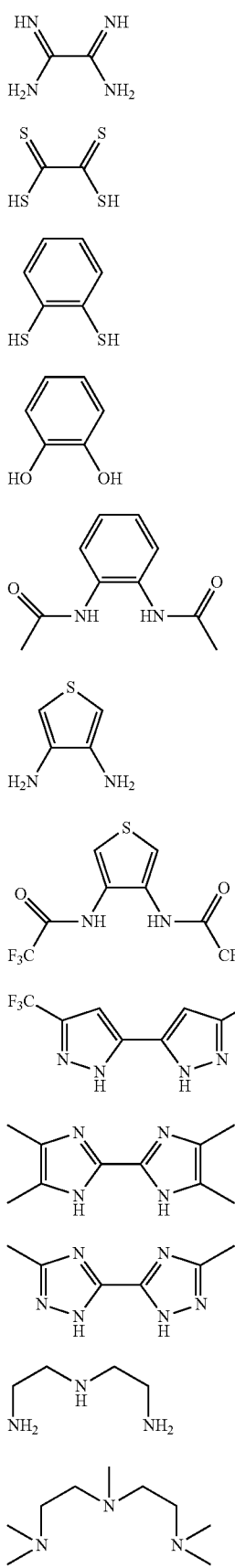
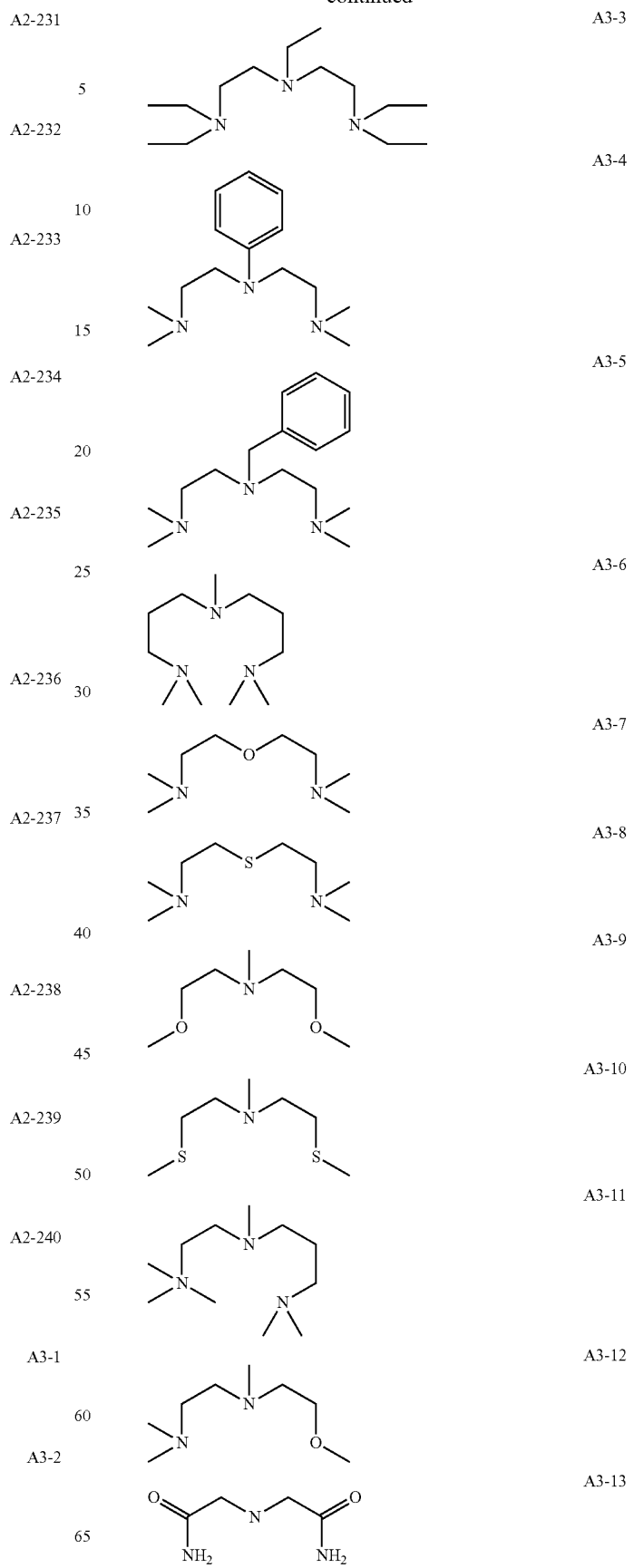

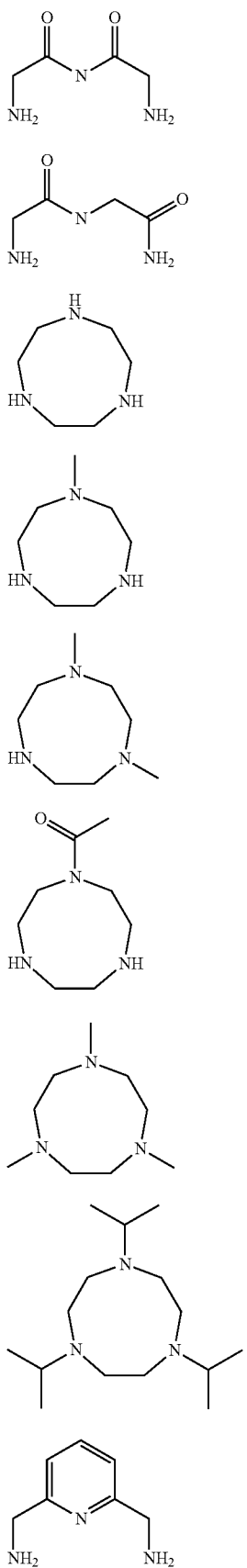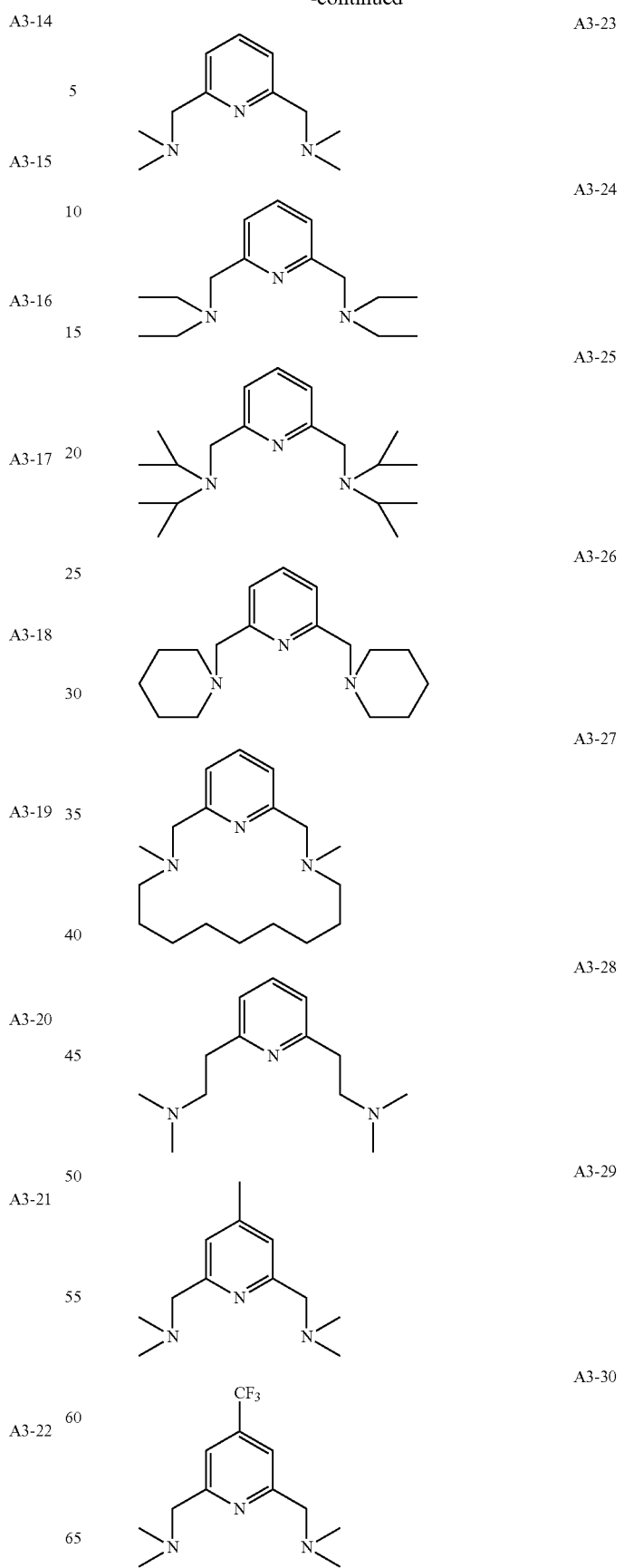

| | |
|---|---|
| A3-31 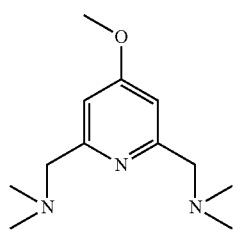 | A3-40 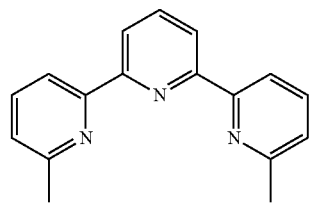 |
| A3-32 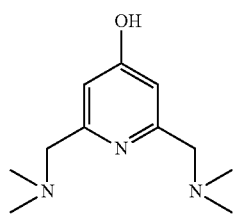 | A3-41 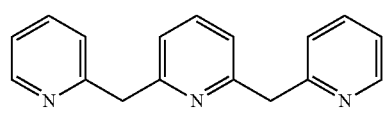 |
| A3-33 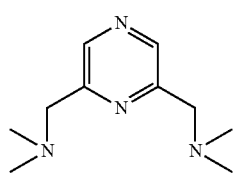 | A3-42 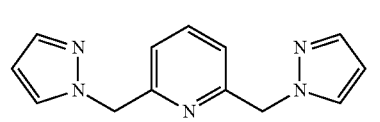 |
| A3-34 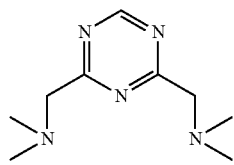 | A3-43 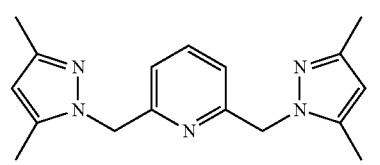 |
| A3-35 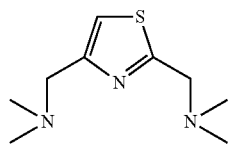 | A3-44 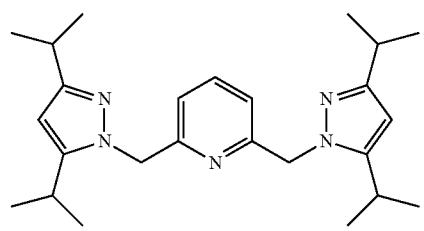 |
| A3-36 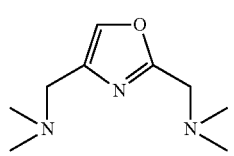 | A3-45 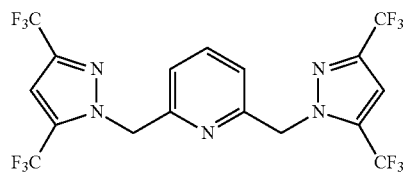 |
| A3-37 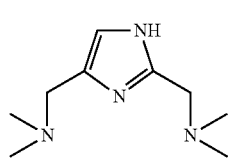 | A3-46 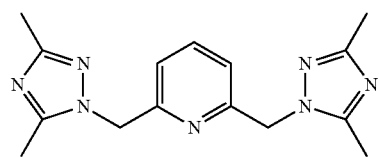 |
| A3-38 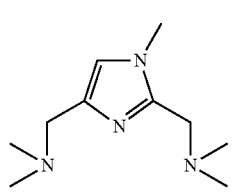 | A3-47 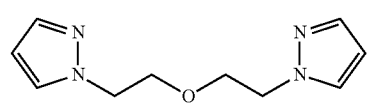 |
| A3-39 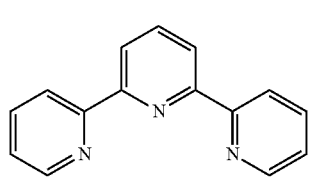 | A3-48 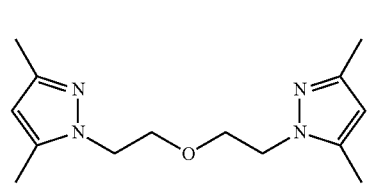 |

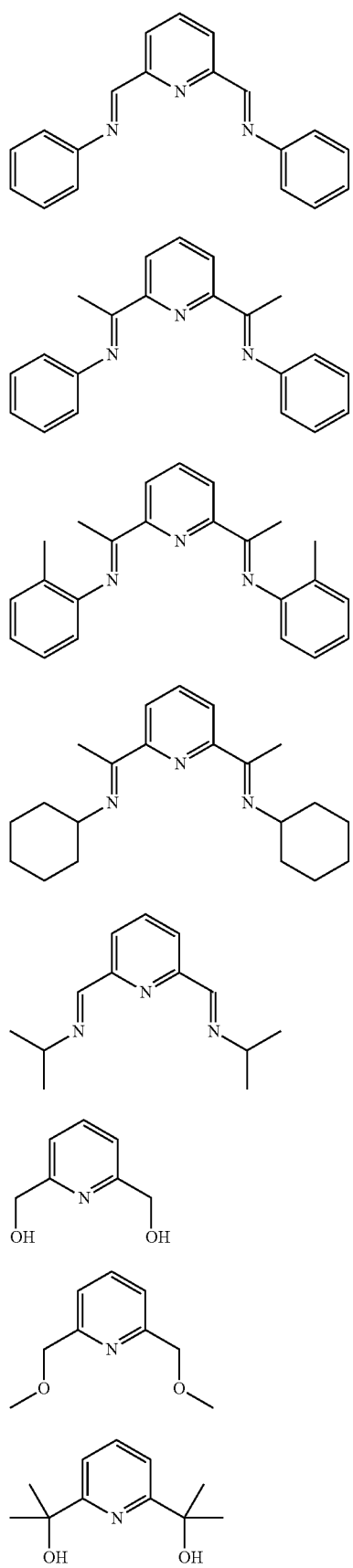
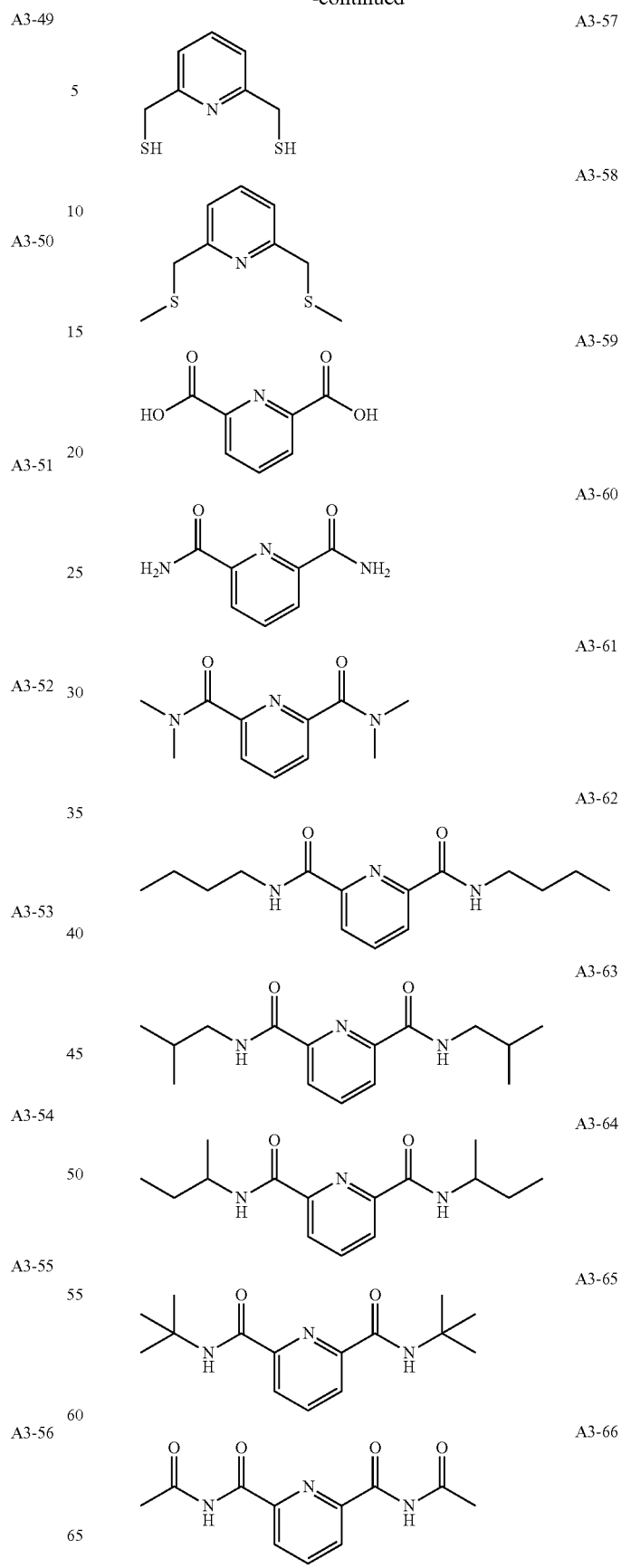

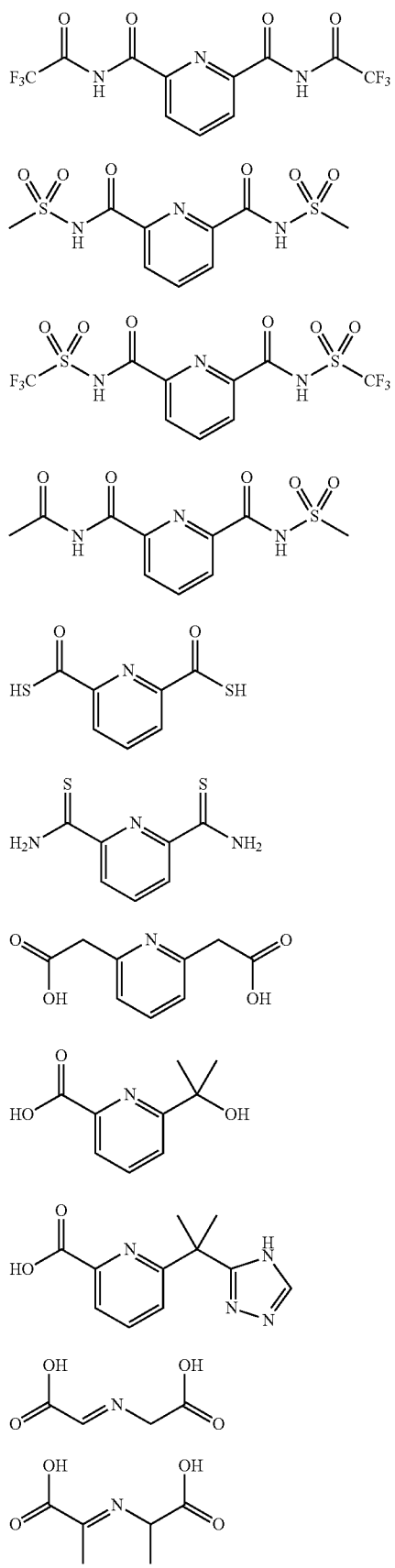
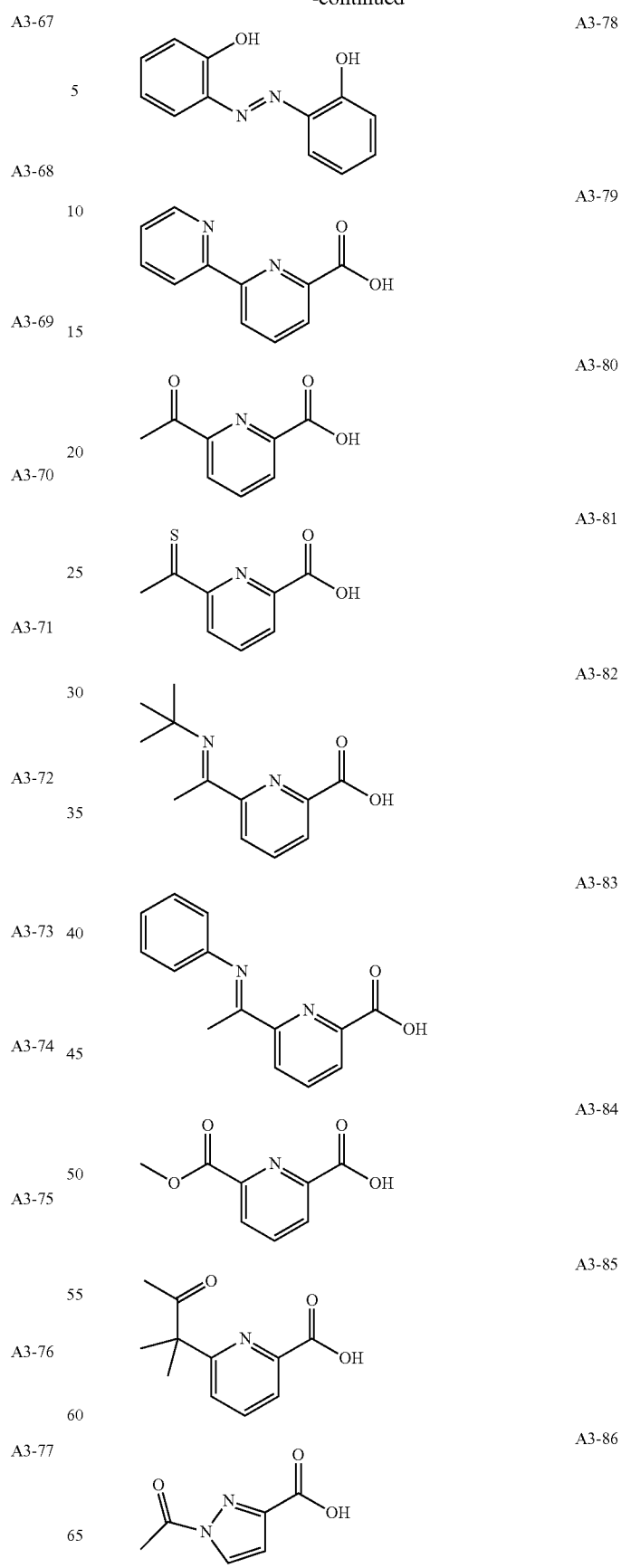

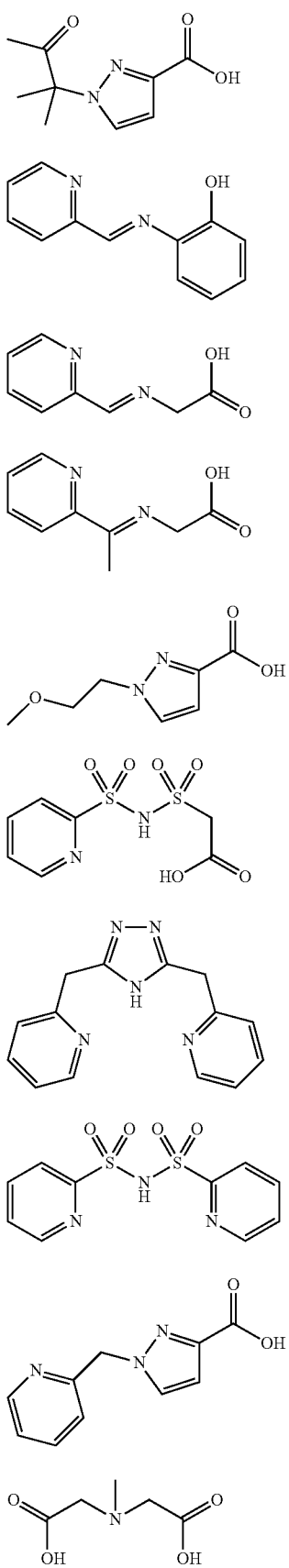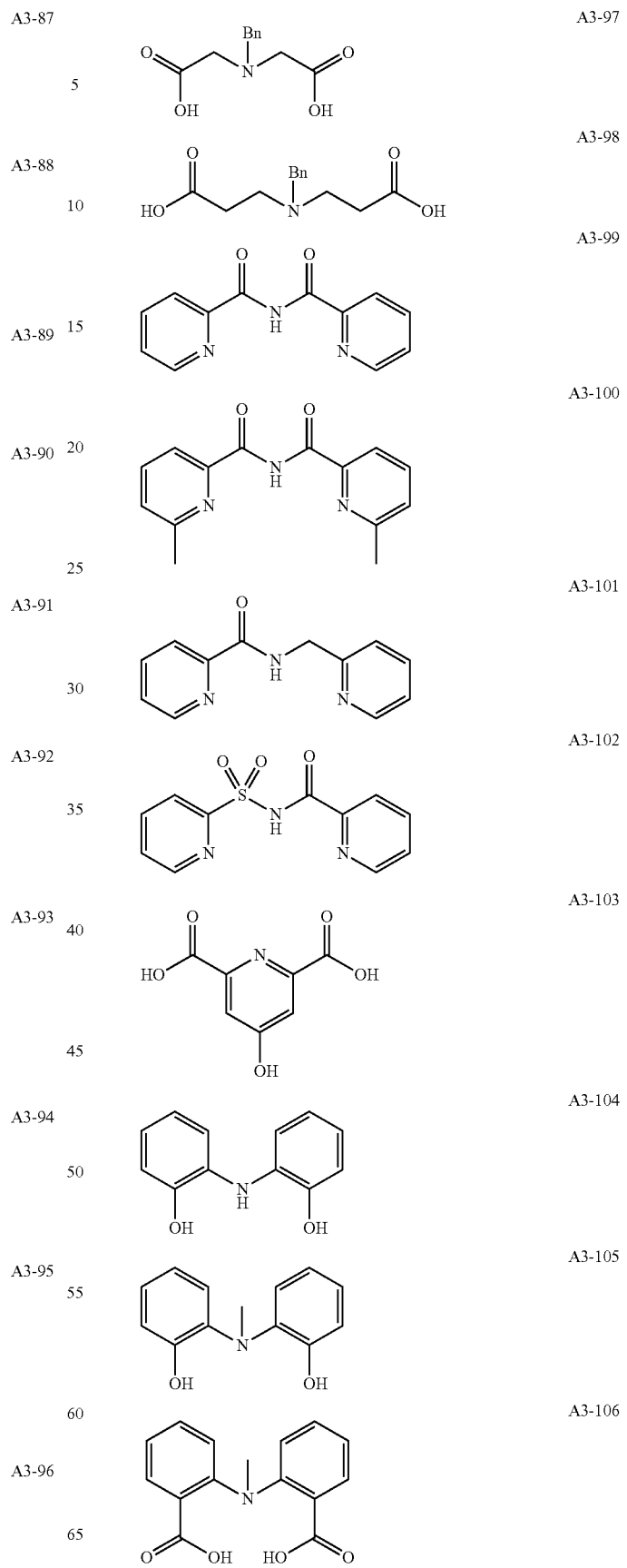

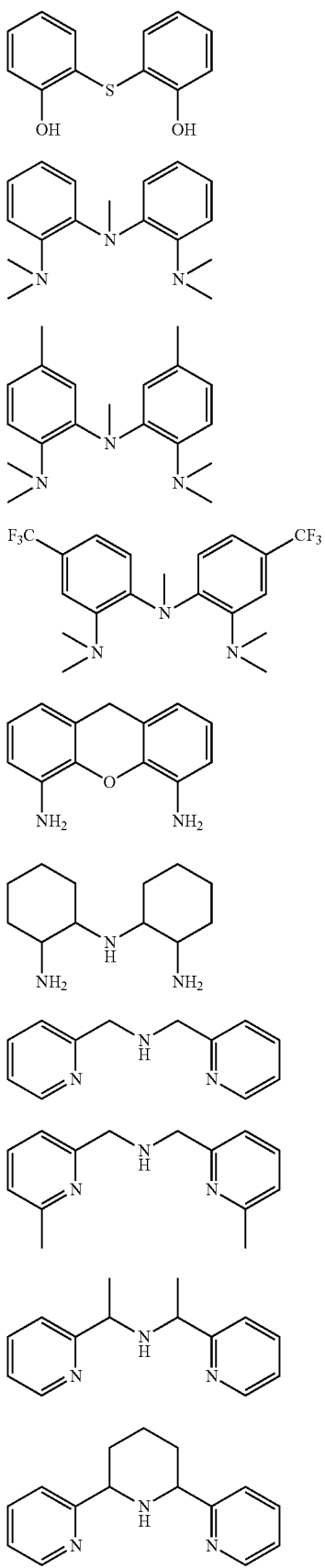
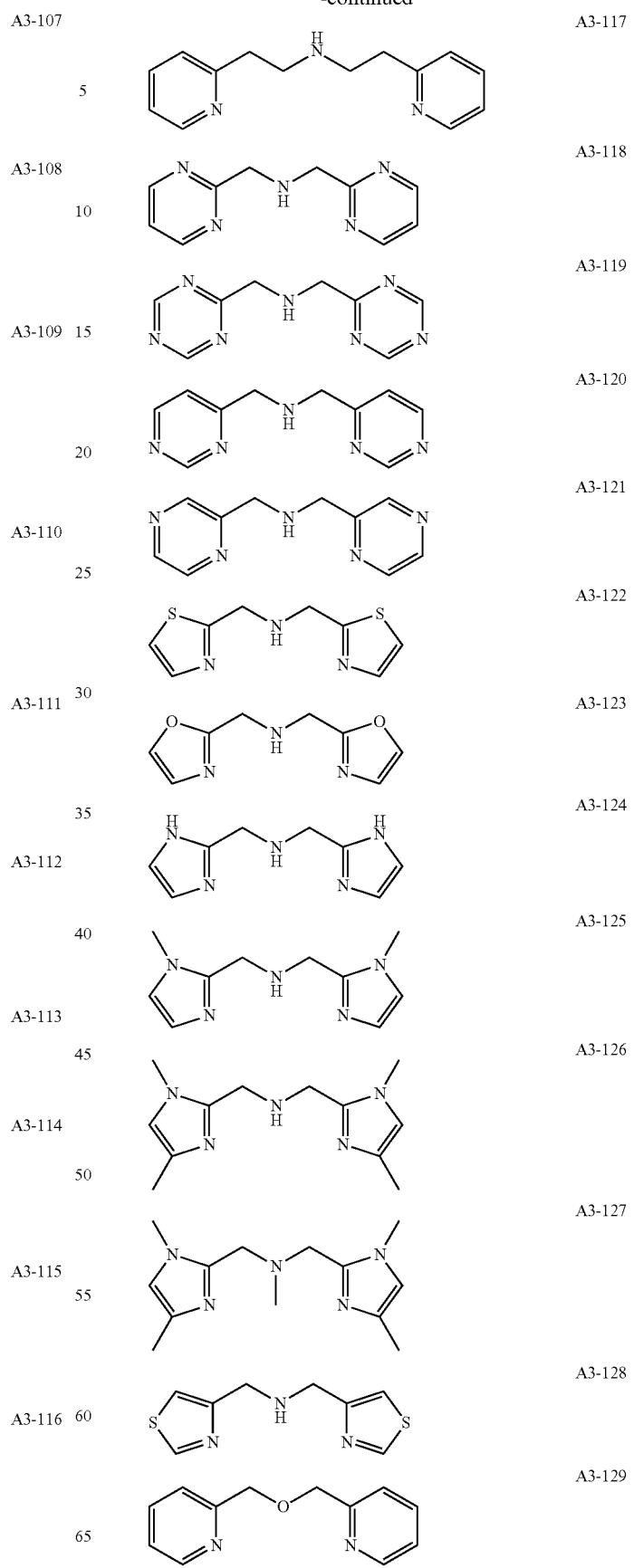

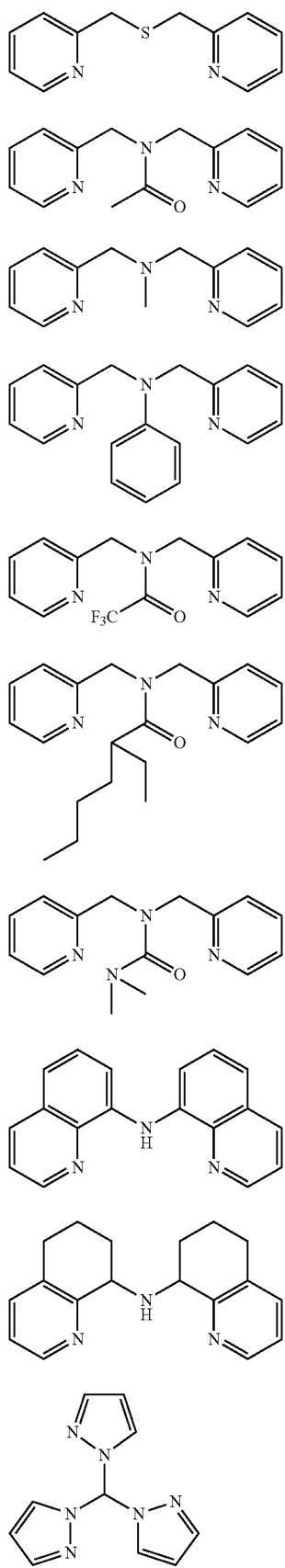
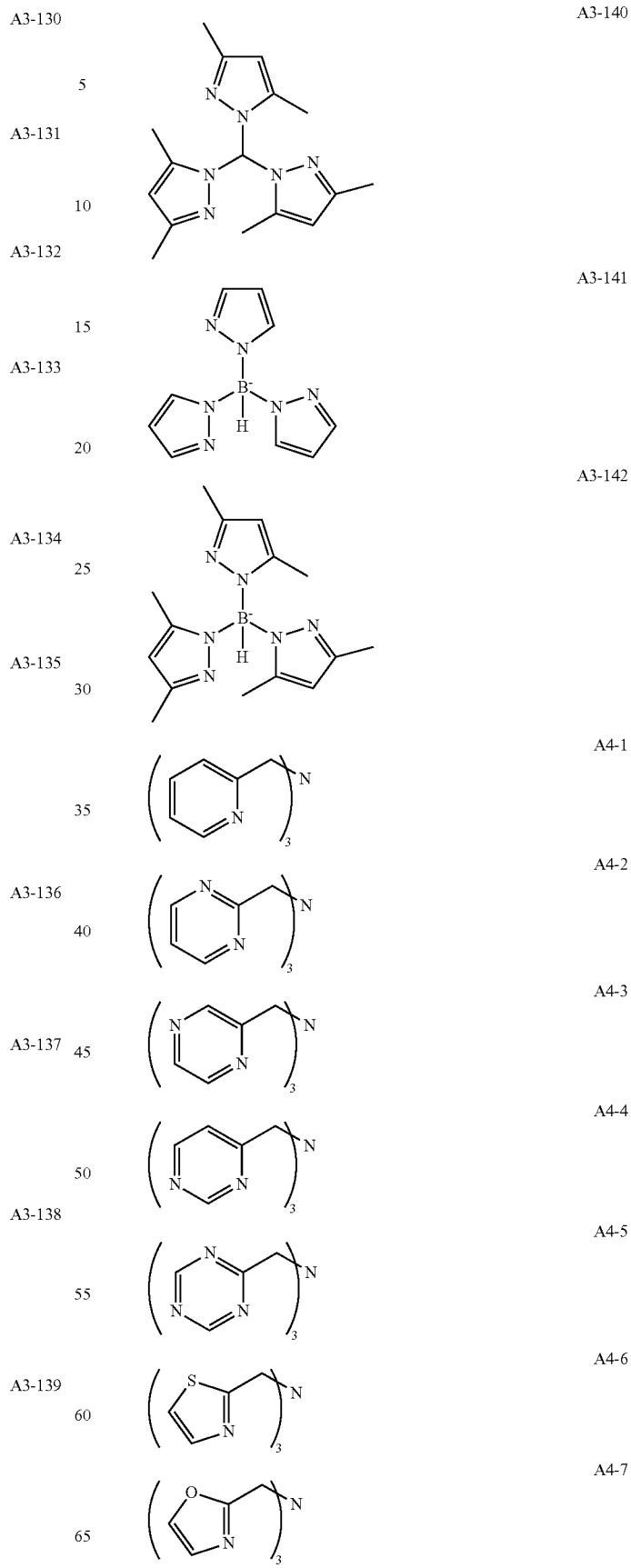

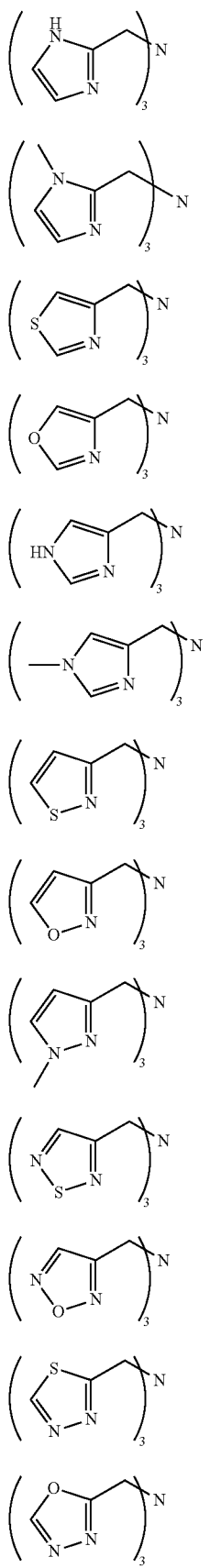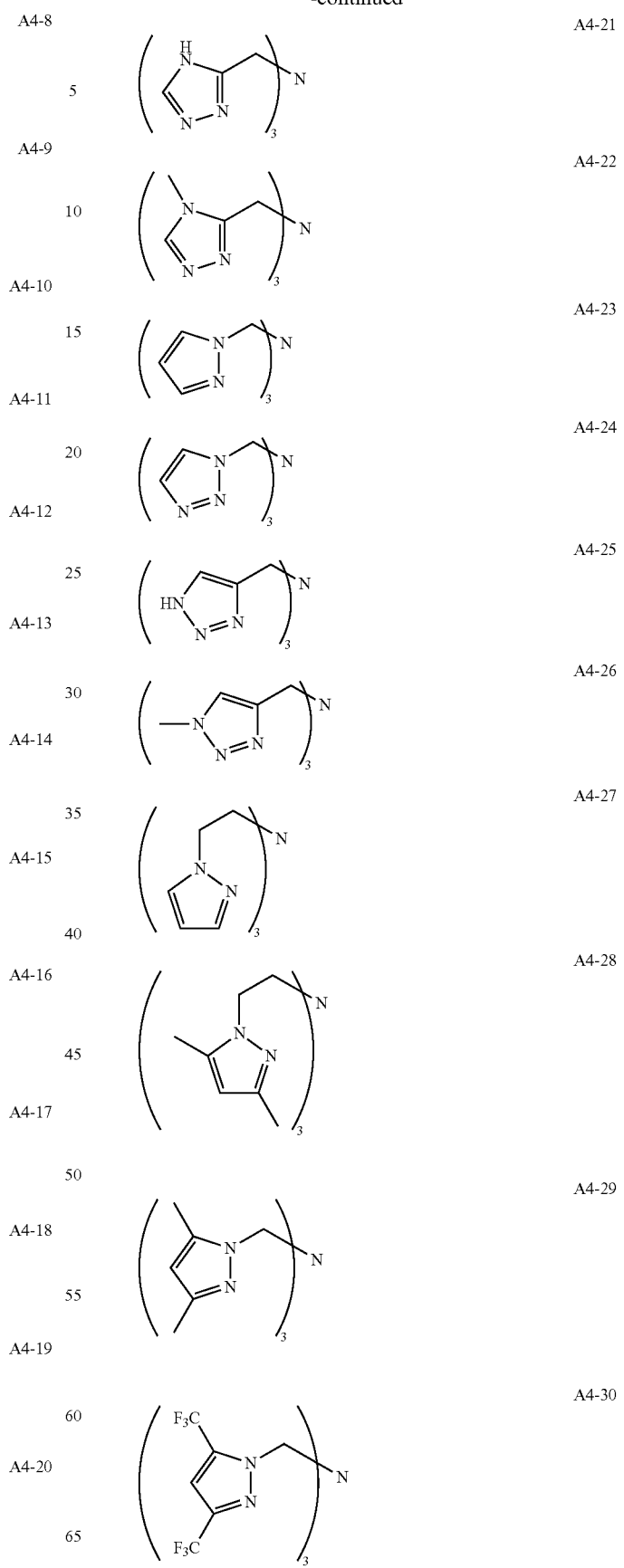

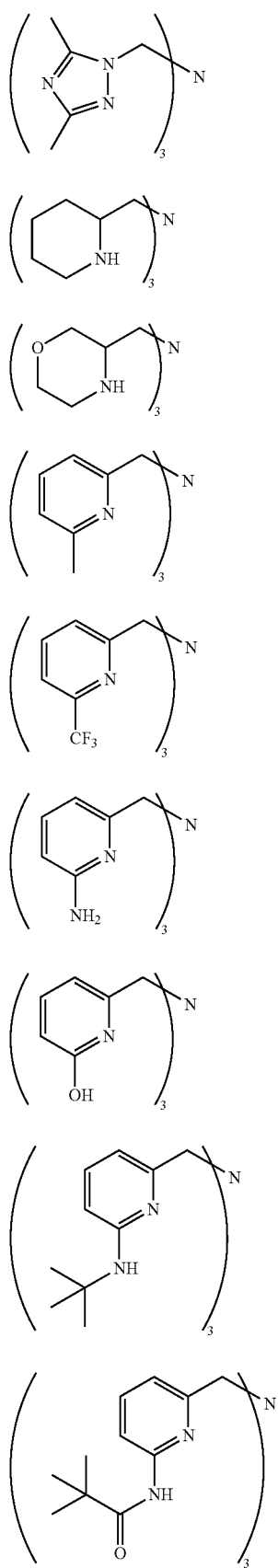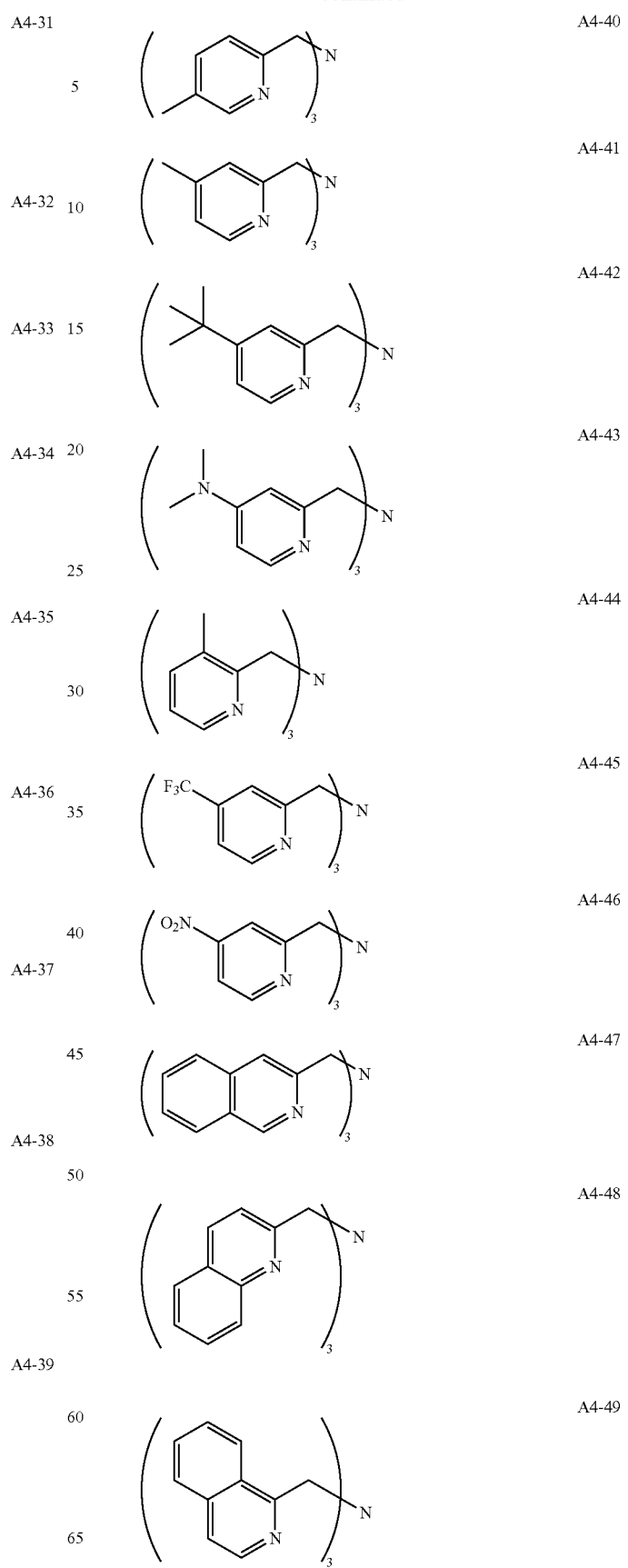

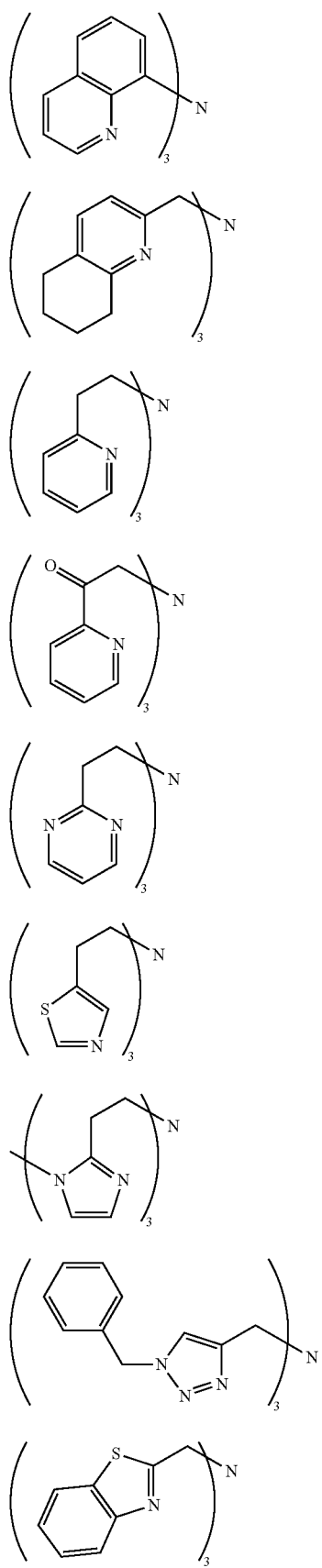
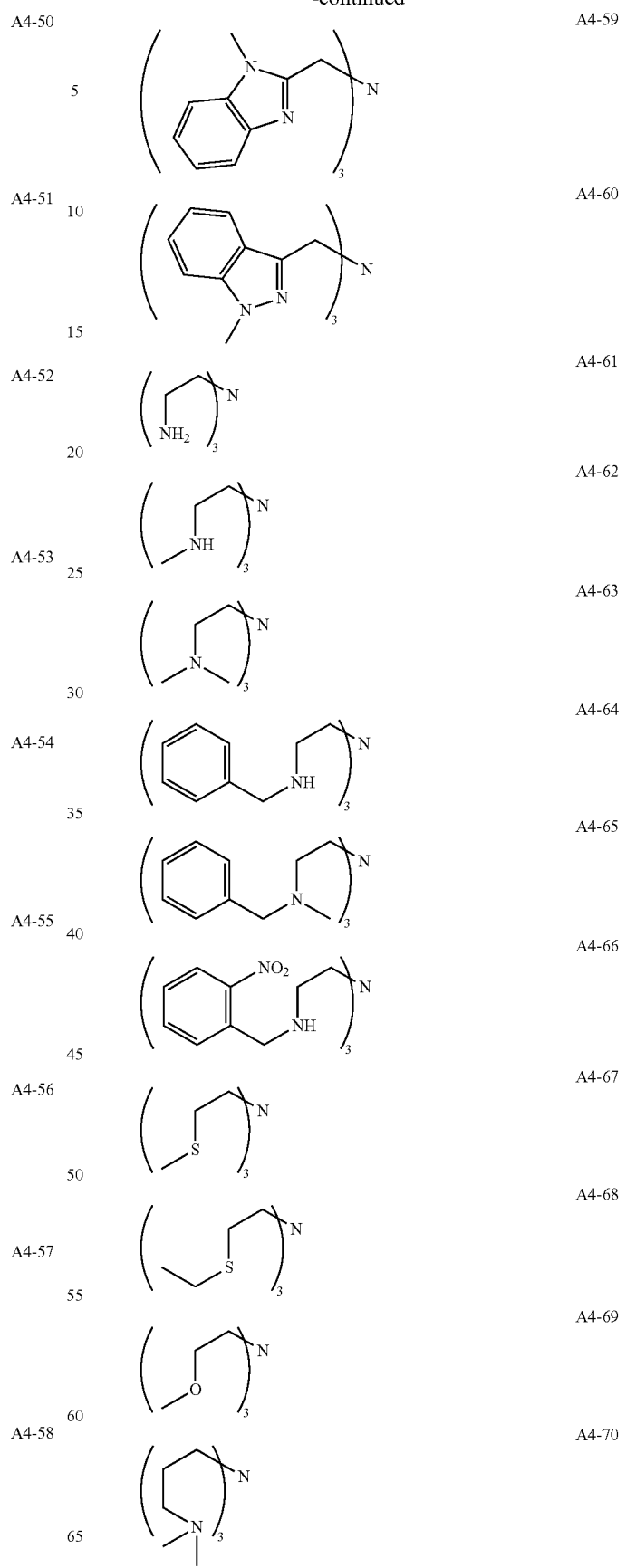

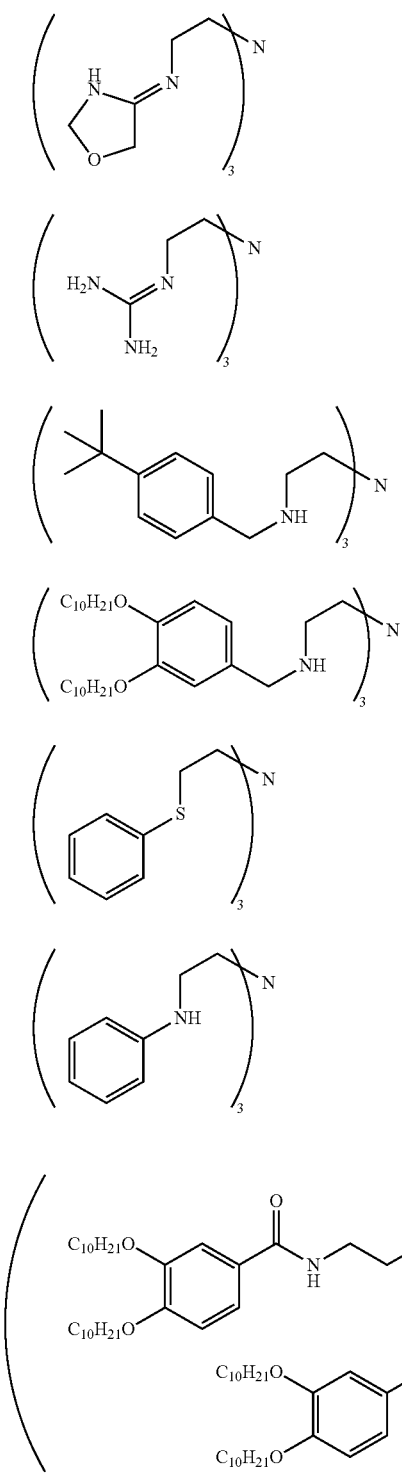
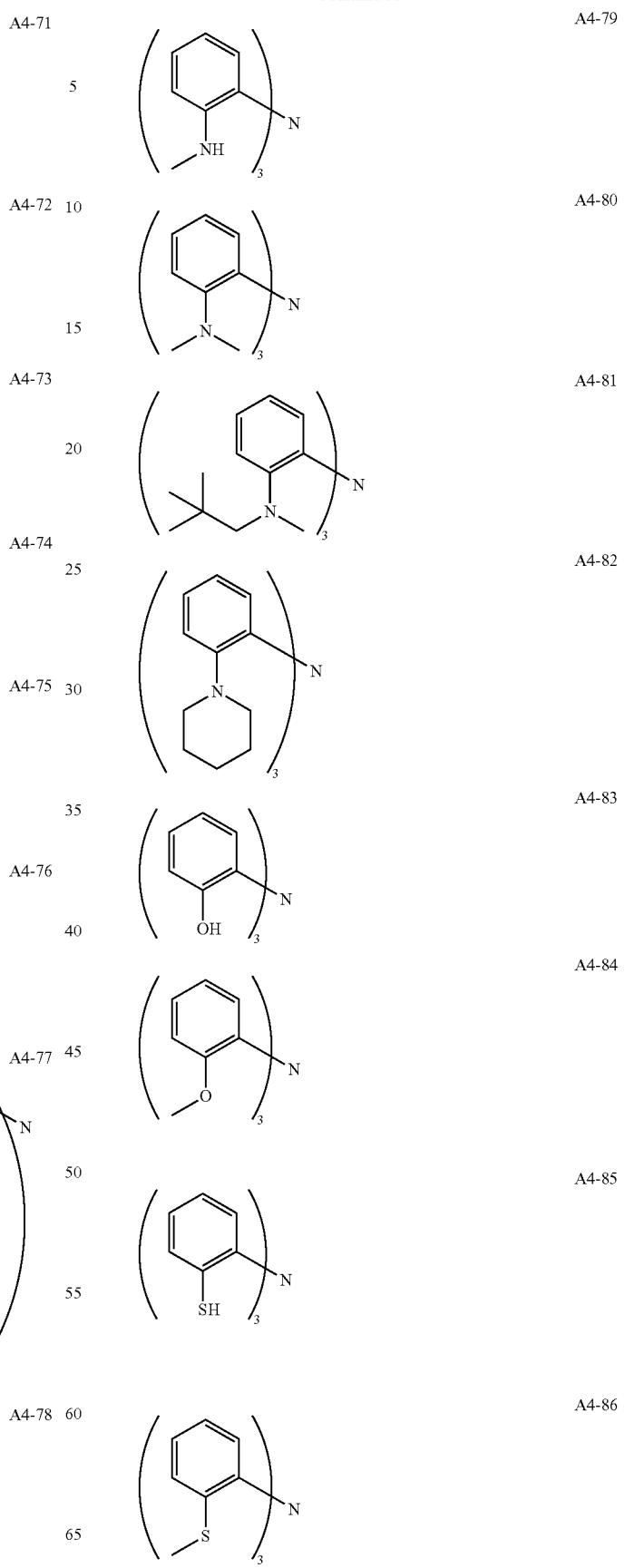

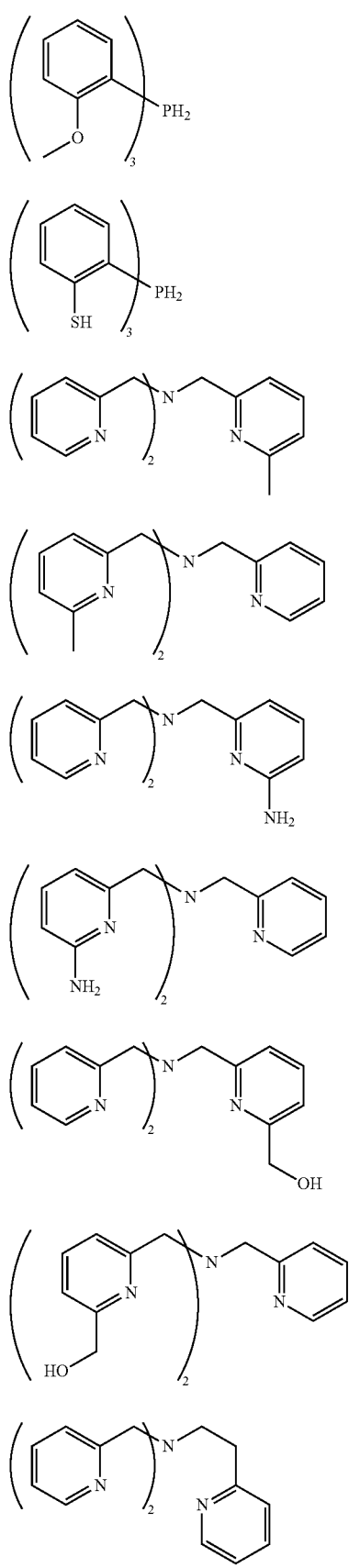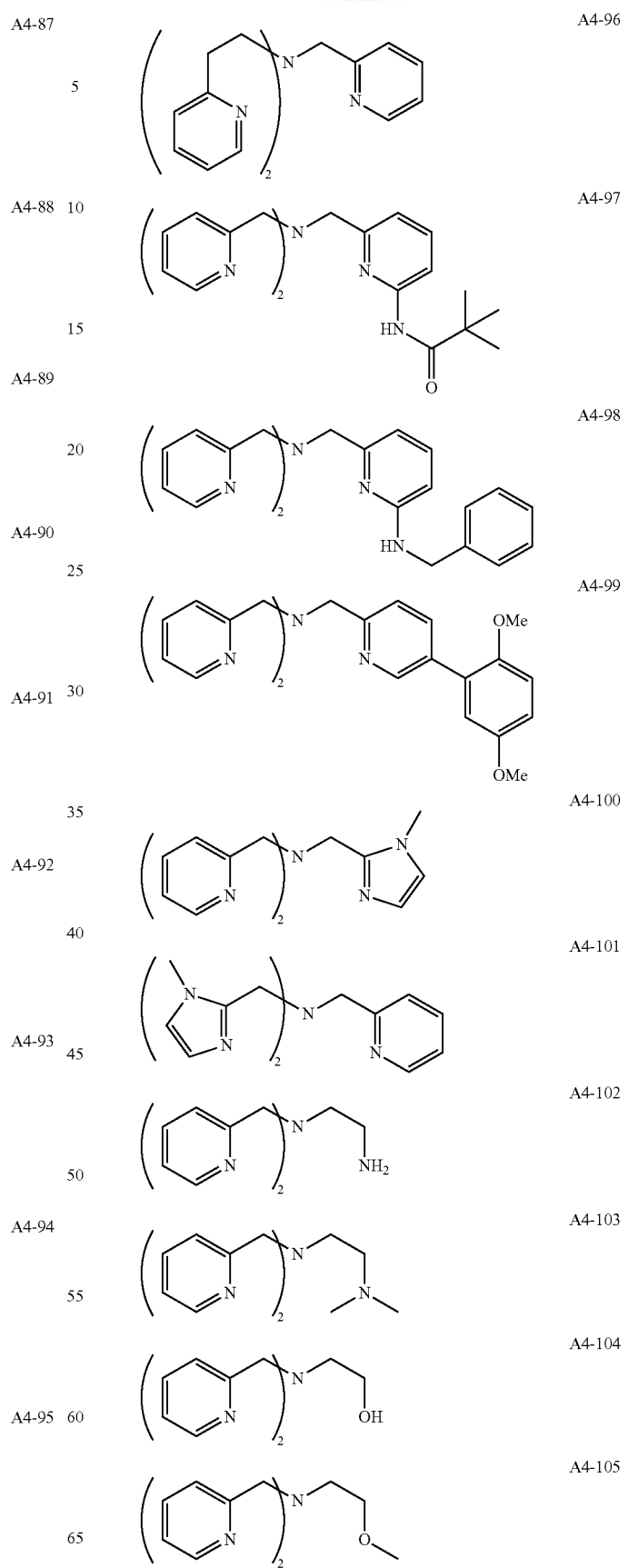

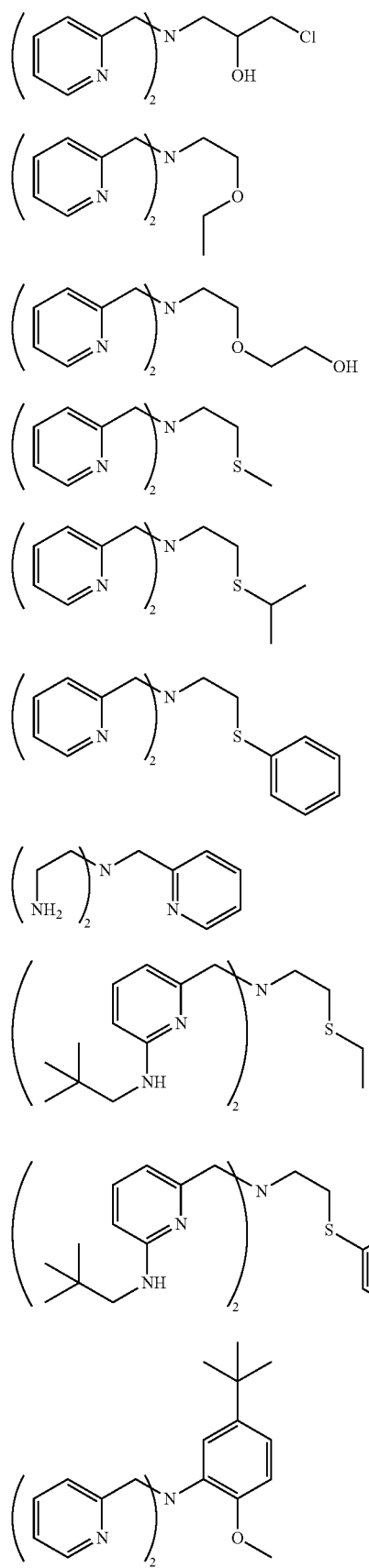
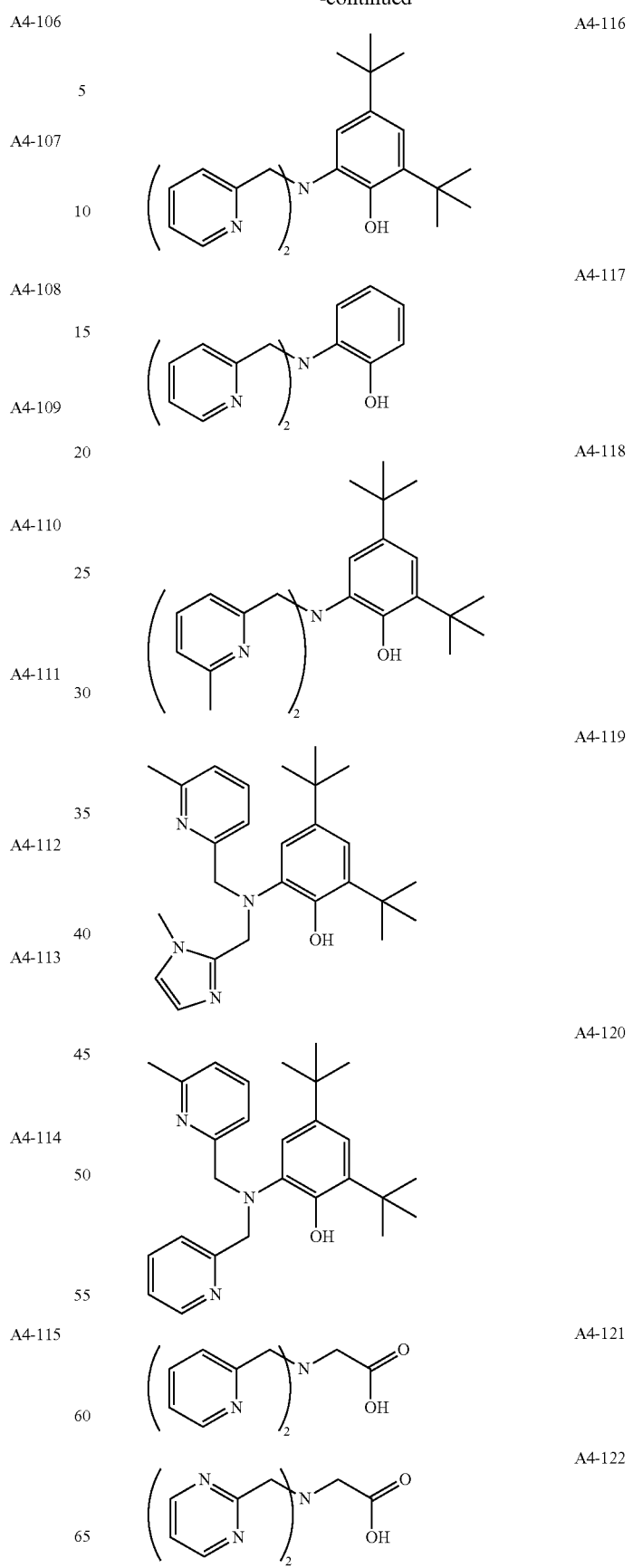

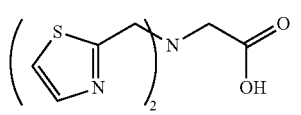
A4-123
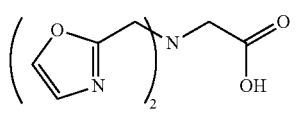
A4-124
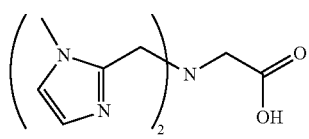
A4-125
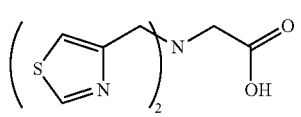
A4-126
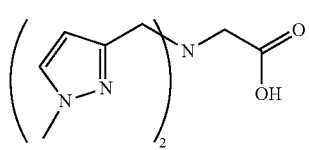
A4-127
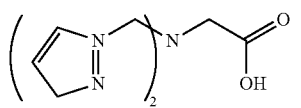
A4-128
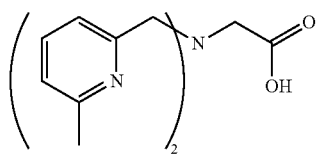
A4-129
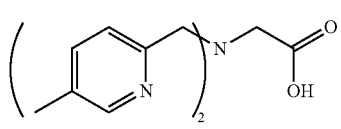
A4-130
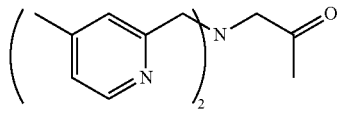
A4-131
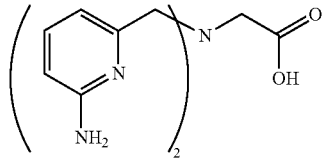
A4-132
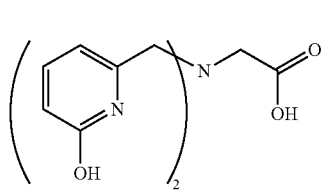
A4-133
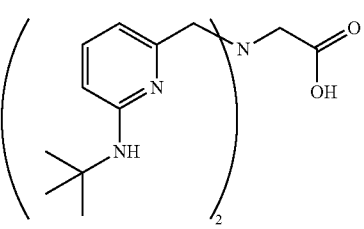
A4-134
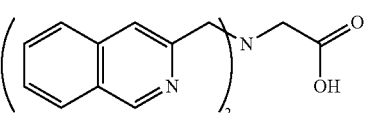
A4-135
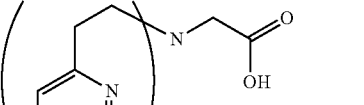
A4-136
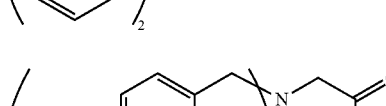
A4-137
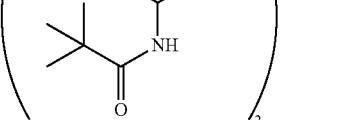
A4-138
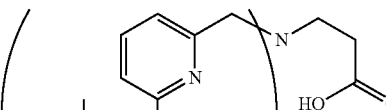
A4-139
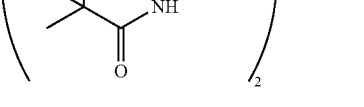
A4-140
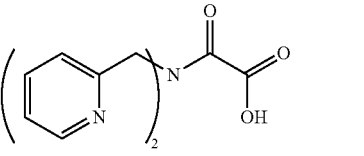
A4-141
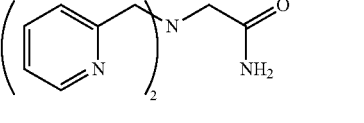
A4-142

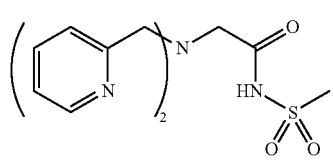 A4-143
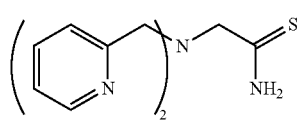 A4-144
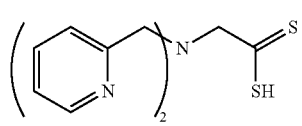 A4-145
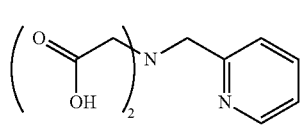 A4-146
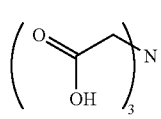 A4-147
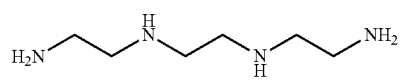 A4-148
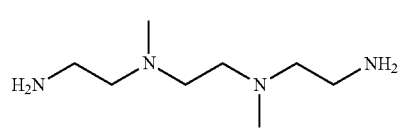 A4-149
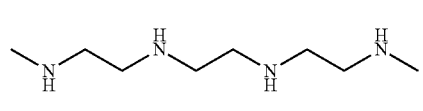 A4-150
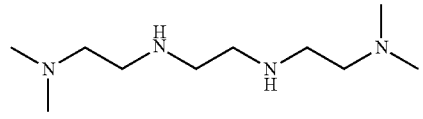 A4-151
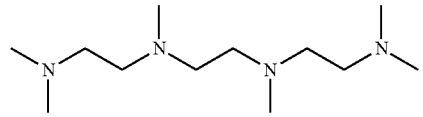 A4-152
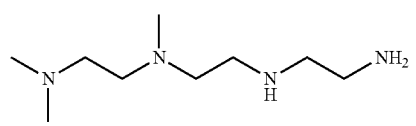 A4-153
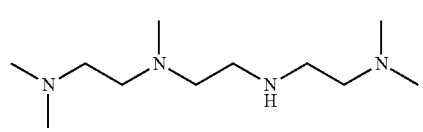 A4-154
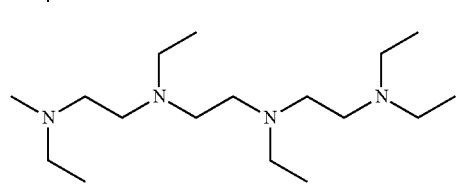 A4-155
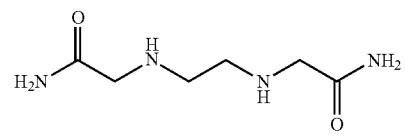 A4-156
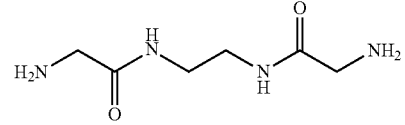 A4-157
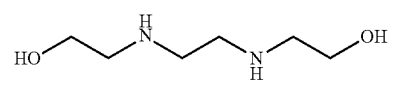 A4-158
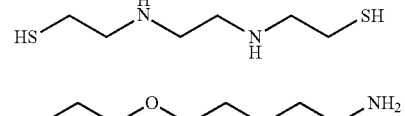 A4-159
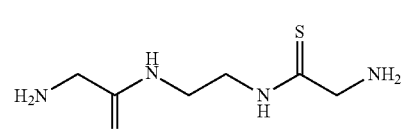 A4-160
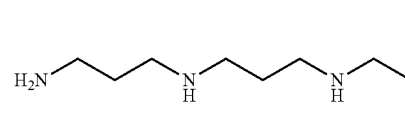 A4-161
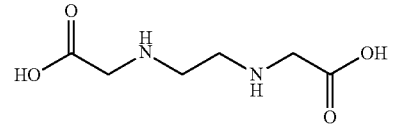 A4-162
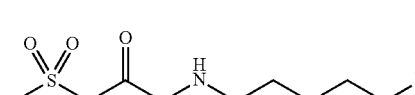 A4-163
 A4-164
 A4-165
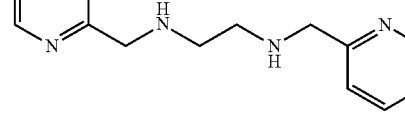 A4-166
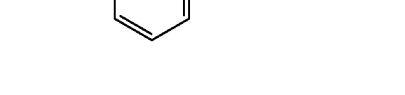 A4-167

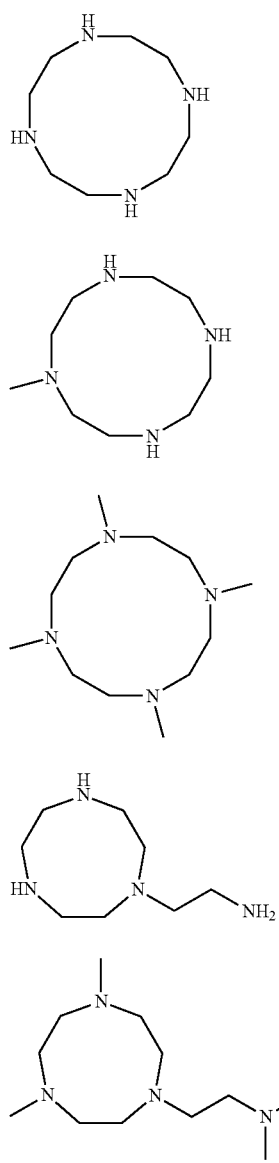
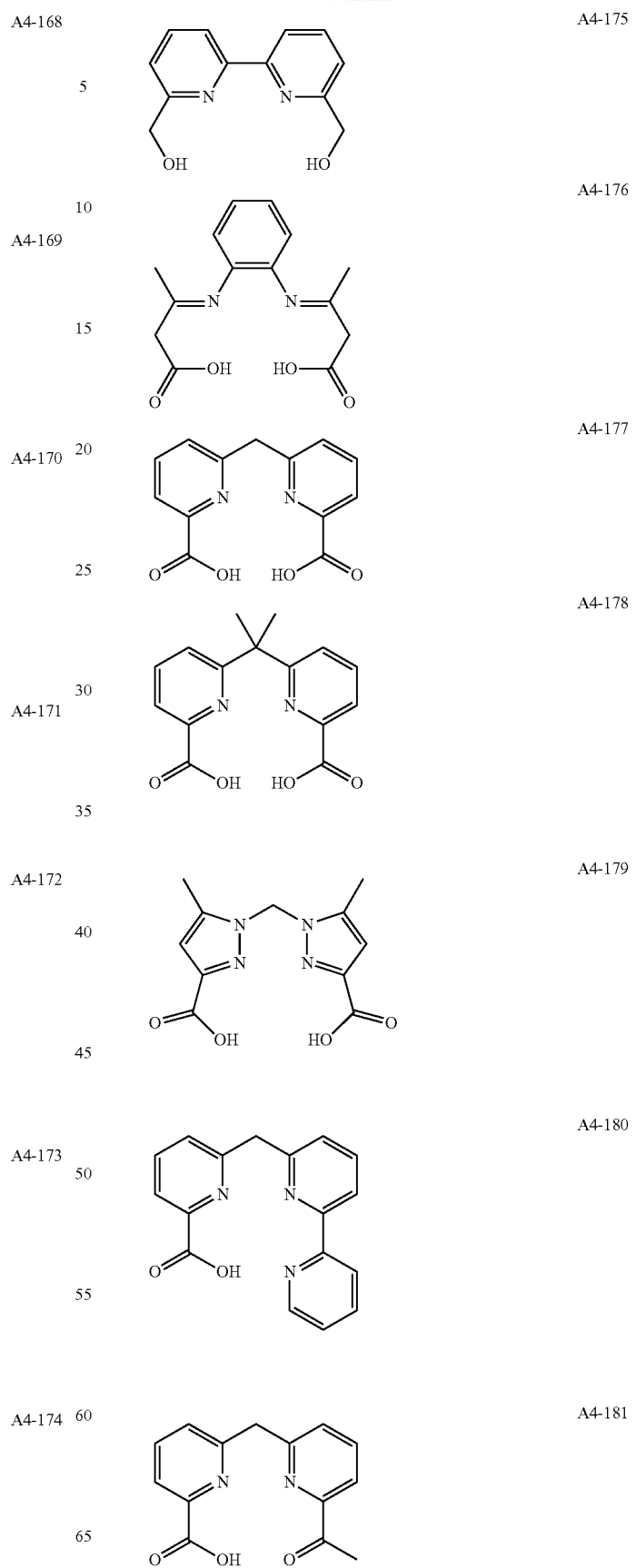

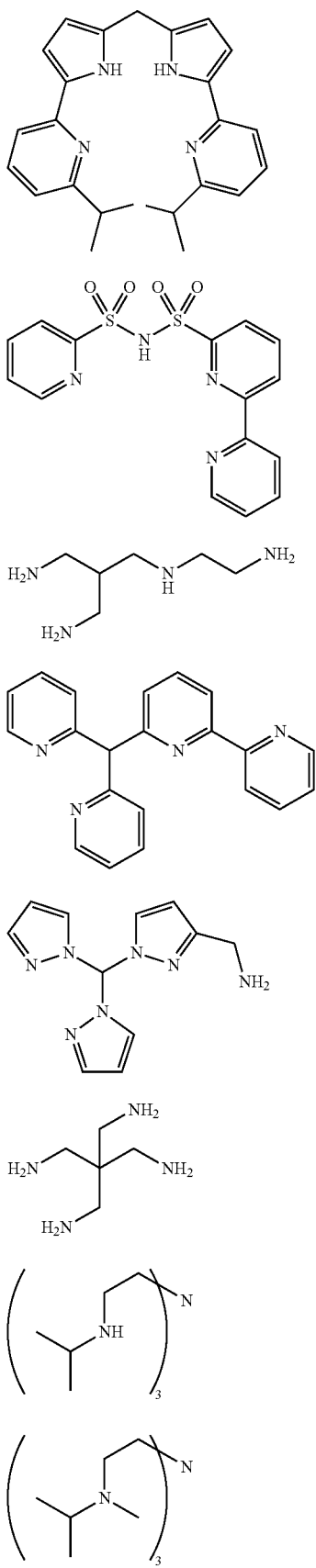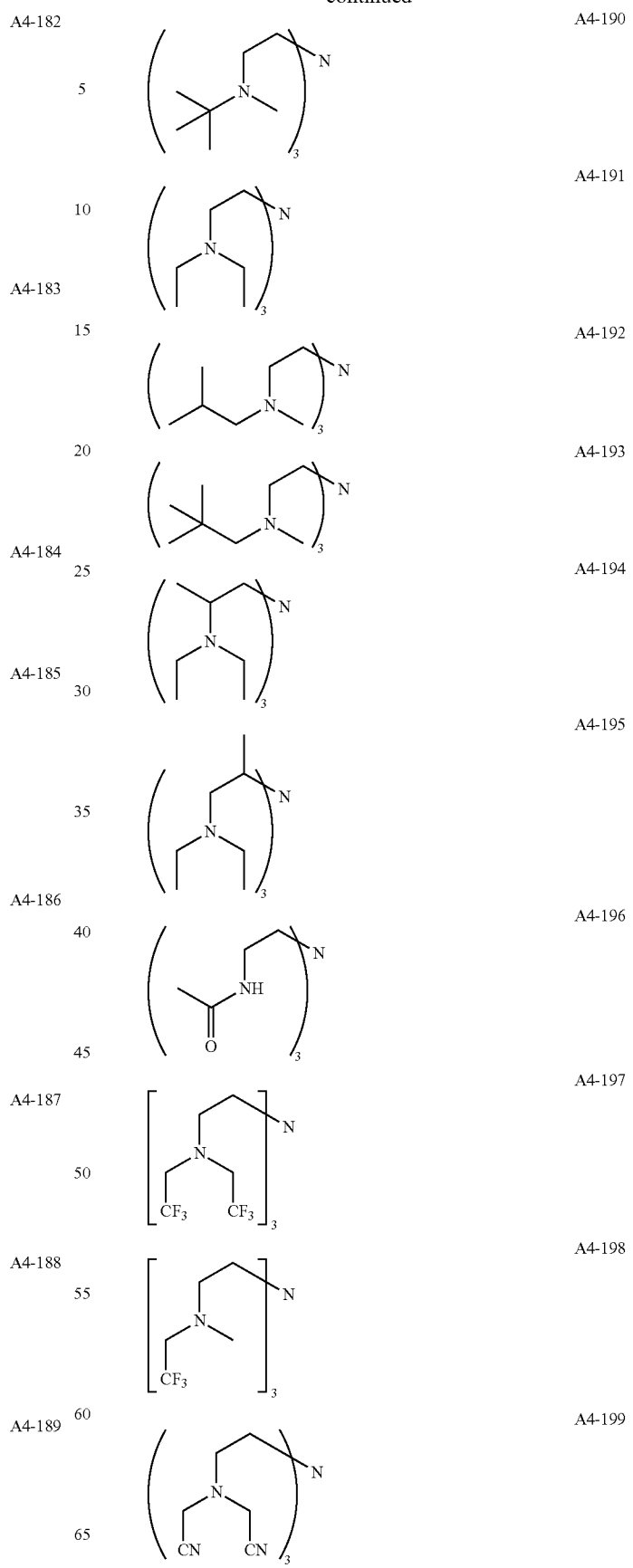

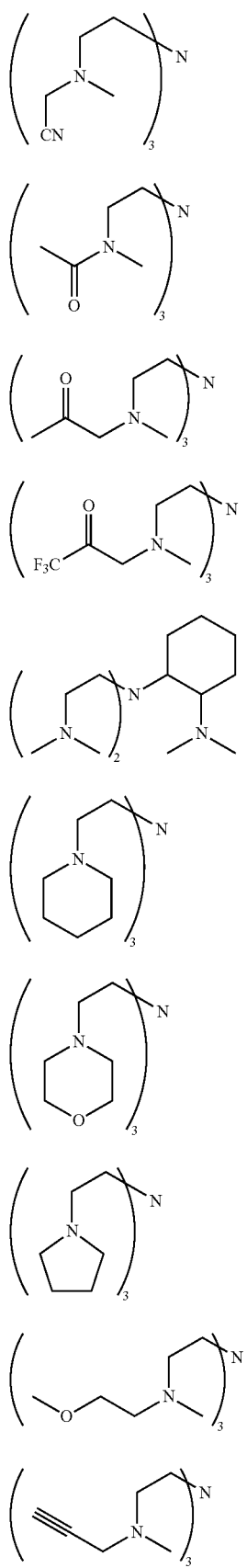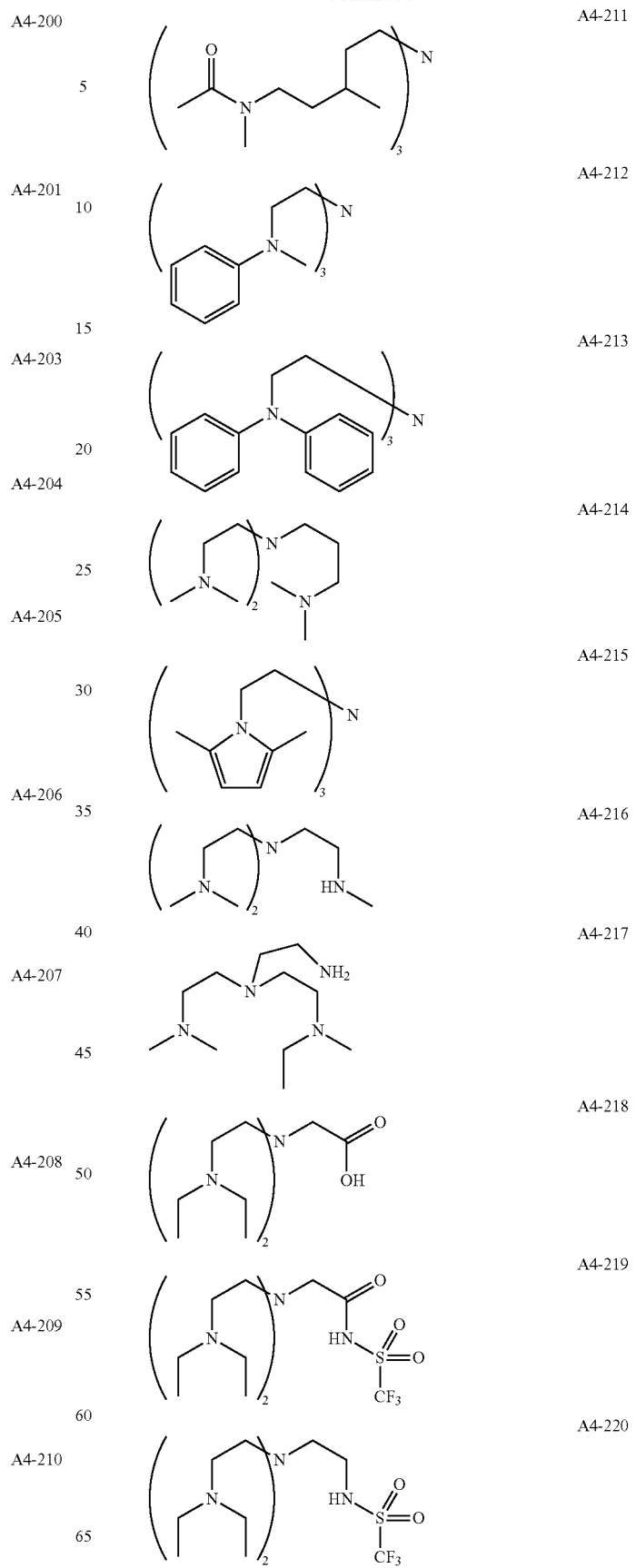

-continued
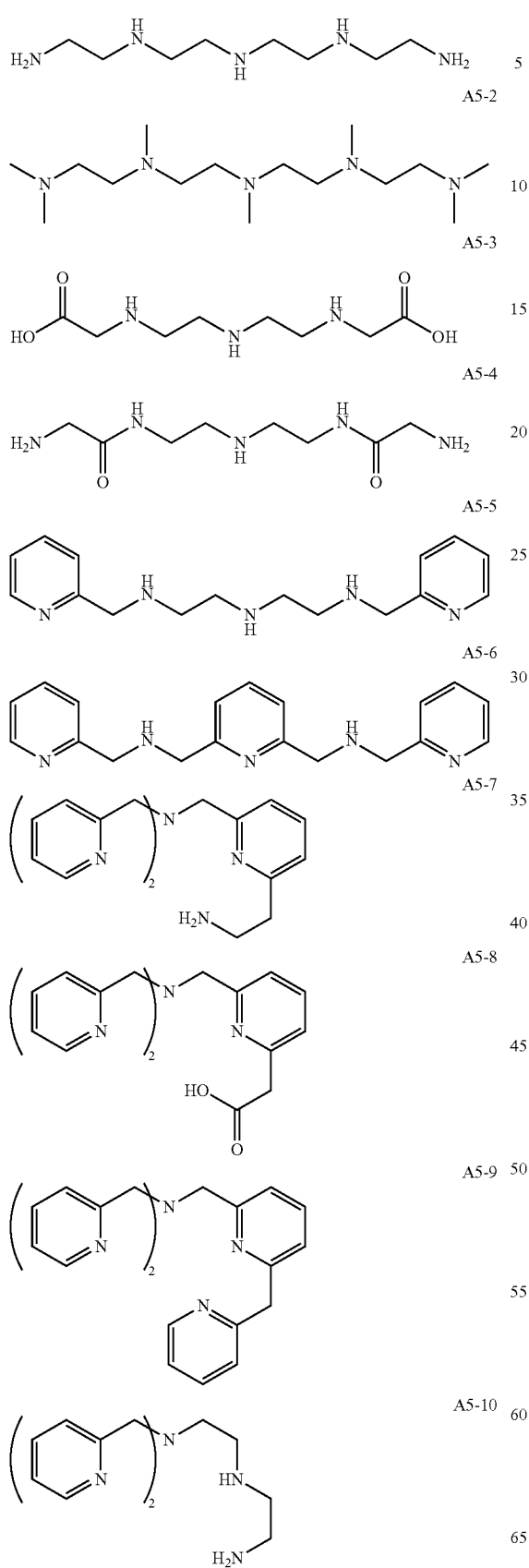
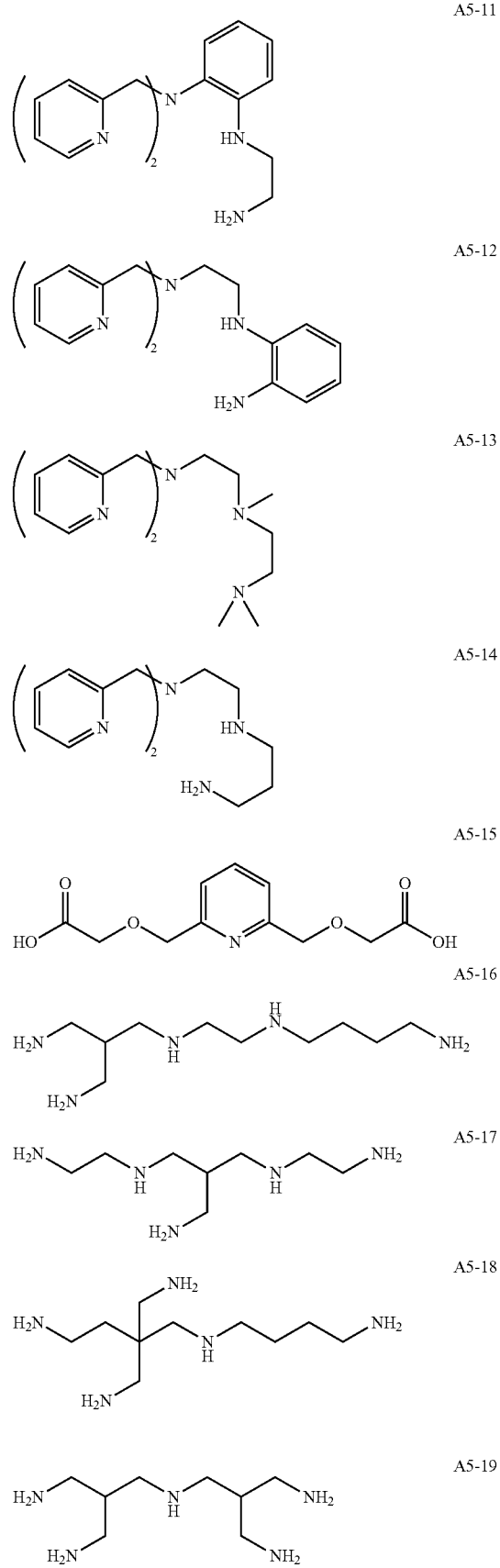

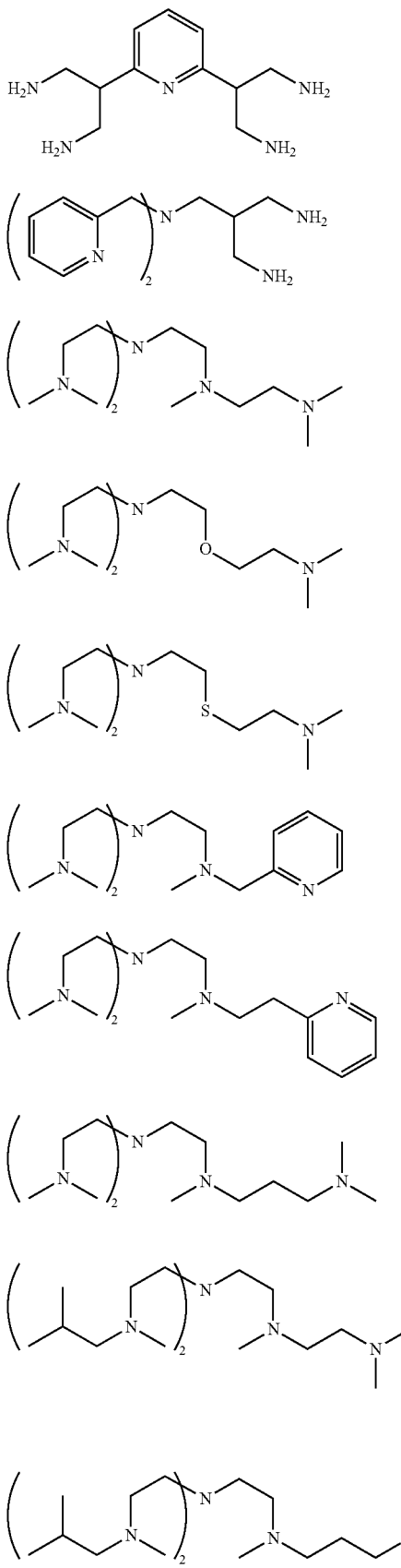
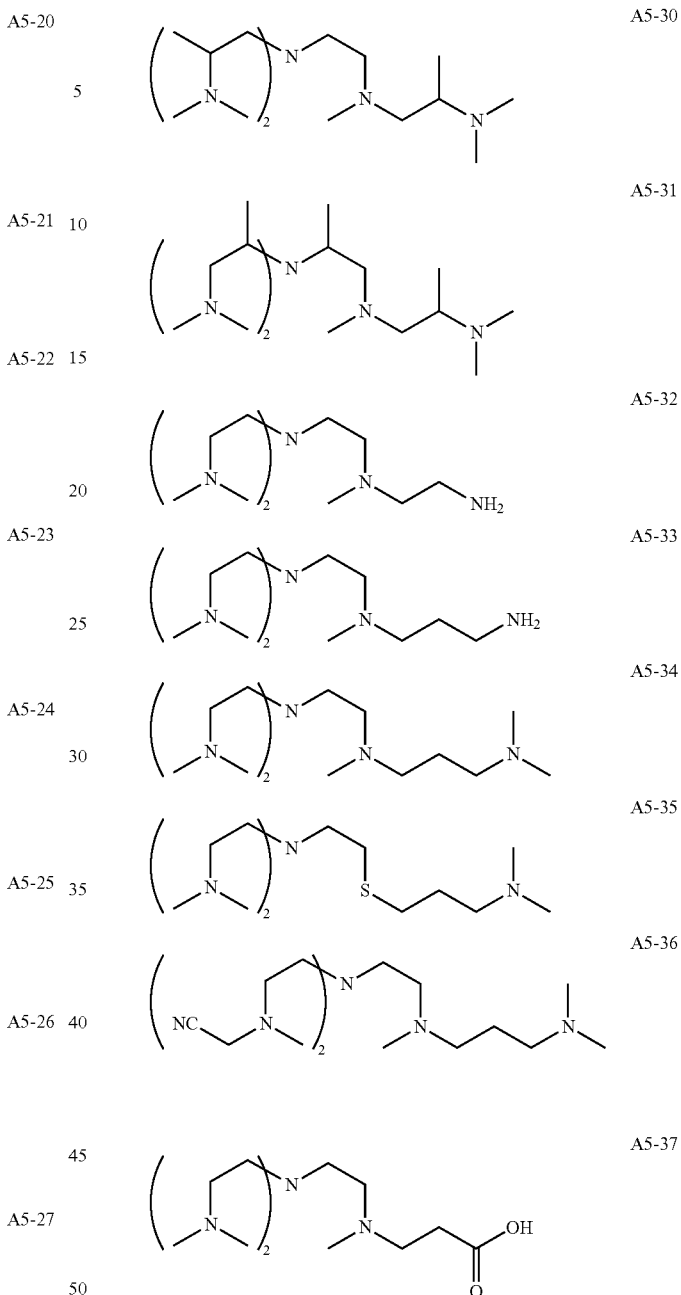

As specific examples of the copper complex which can be used in the present invention, examples shown in the following tables are used, but the present invention is not limited thereto. In the following tables, Ph represents a phenyl group.

In addition, a component other than the copper complex of the near infrared ray absorbent composition (solvent or various additives) may further perform coordination, and some ligands of the copper complex may exist in a state of being replaced with the component other than the copper complex. This is general characteristics for a copper (II) complex having $d^9$ electron disposed with substitution activity.

TABLE 2

| Copper complex | Ligand Compound (A) (1) | Unidentate ligand (2) | Unidentate ligand (3) | (1):(2):(3):Cu (II) Molar ratio | Counter ion |
|---|---|---|---|---|---|
| Cu1-1 | A2-1 | A1-1 | — | 1:2:0:1 | — |
| Cu1-2 | A2-2 | A1-1 | — | 1:2:0:1 | — |
| Cu1-3 | A2-6 | A1-1 | — | 1:2:0:1 | — |
| Cu1-4 | A2-10 | A1-1 | — | 1:2:0:1 | — |
| Cu1-5 | A2-11 | A1-1 | — | 1:2:0:1 | — |
| Cu1-6 | A2-15 | A1-1 | — | 1:2:0:1 | — |
| Cu1-7 | A2-19 | A1-1 | — | 1:2:0:1 | — |
| Cu1-8 | A2-20 | A1-1 | — | 1:2:0:1 | — |
| Cu1-9 | A2-22 | A1-1 | — | 1:2:0:1 | — |
| Cu1-10 | A2-23 | A1-1 | — | 1:2:0:1 | — |
| Cu1-11 | A2-26 | A1-1 | — | 1:2:0:1 | — |
| Cu1-12 | A2-28 | A1-1 | — | 1:2:0:1 | — |
| Cu1-13 | A2-32 | A1-1 | — | 1:2:0:1 | — |
| Cu1-14 | A2-36 | A1-1 | — | 1:2:0:1 | — |
| Cu1-15 | A2-40 | A1-1 | — | 1:2:0:1 | — |
| Cu1-16 | A2-1 | A1-3 | — | 1:2:0:1 | — |
| Cu1-17 | A2-1 | A1-23 | — | 1:2:0:1 | — |
| Cu1-18 | A2-1 | A1-16 | — | 1:2:0:1 | — |
| Cu1-19 | A2-1 | A1-21 | — | 1:2:0:1 | — |
| Cu1-20 | A2-1 | A1-28 | — | 1:2:0:1 | — |
| Cu1-21 | A2-1 | A1-2 | — | 1:2:0:1 | — |
| Cu1-22 | A2-1 | A1-9 | — | 1:2:0:1 | — |
| Cu1-23 | A2-1 | A1-10 | — | 1:2:0:1 | — |
| Cu1-24 | A2-1 | A1-22 | — | 1:2:0:1 | — |
| Cu1-25 | A2-1 | A1-24 | — | 1:2:0:1 | — |
| Cu1-26 | A2-1 | A1-26 | — | 1:2:0:1 | — |
| Cu1-27 | A2-1 | A1-31 | — | 1:2:0:1 | — |
| Cu1-28 | A2-1 | A1-35 | — | 1:2:0:1 | — |
| Cu1-29 | A2-1 | A1-36 | — | 1:2:0:1 | — |
| Cu1-30 | A2-1 | A1-38 | — | 1:2:0:1 | — |
| Cu1-31 | A2-1 | A1-1 | A1-41 | 1:2:1:1 | — |
| Cu1-32 | A2-1 | A1-1 | A1-44 | 1:2:1:1 | — |
| Cu1-33 | A2-1 | A1-1 | A1-47 | 1:2:1:1 | — |
| Cu1-34 | A2-1 | A1-1 | A1-51 | 1:2:1:1 | — |
| Cu1-35 | A2-1 | A1-1 | A1-55 | 1:2:1:1 | — |
| Cu1-36 | A2-1 | A1-1 | — | 2:1:0:1 | Cl |

TABLE 3

| Copper complex | Ligand Compound (A) (1) | Compound (A) (2) | Unidentate ligand (3) | (1):(2):(3):Cu (II) Molar ratio | Counter ion |
|---|---|---|---|---|---|
| Cu2-1 | A2-1 | A2-10 | A1-1 | 1:1:2:1 | — |
| Cu2-2 | A2-1 | A2-23 | A1-1 | 1:1:2:1 | — |
| Cu2-3 | A2-1 | A2-32 | A1-1 | 1:1:2:1 | — |
| Cu2-4 | A2-1 | A2-44 | A1-1 | 1:1:1:1 | — |
| Cu2-5 | A2-1 | A2-76 | A1-1 | 1:1:1:1 | — |
| Cu2-6 | A2-1 | A2-131 | A1-1 | 1:1:1:1 | — |
| Cu2-7 | A2-1 | A2-133 | A1-1 | 1:1:1:1 | — |
| Cu2-8 | A2-1 | A2-148 | A1-1 | 1:1:1:1 | — |
| Cu2-9 | A2-1 | A2-193 | A1-1 | 1:1:1:1 | — |
| Cu2-10 | A2-1 | A2-196 | A1-1 | 1:1:1:1 | — |
| Cu2-11 | A2-1 | A2-214 | — | 1:1:0:1 | — |
| Cu2-12 | A2-1 | A2-230 | — | 1:1:0:1 | — |
| Cu2-13 | A2-44 | — | — | 2:0:0:1 | — |
| Cu2-14 | A2-76 | — | — | 2:0:0:1 | — |
| Cu2-15 | A2-131 | — | — | 2:0:0:1 | — |
| Cu2-16 | A2-133 | — | — | 2:0:0:1 | — |
| Cu2-17 | A2-148 | — | — | 2:0:0:1 | — |
| Cu2-18 | A2-193 | — | — | 2:0:0:1 | — |
| Cu2-19 | A2-196 | — | — | 2:0:0:1 | — |
| Cu2-20 | A2-44 | A2-76 | — | 1:1:0:1 | — |
| Cu2-21 | A2-44 | A2-131 | — | 1:1:0:1 | — |
| Cu2-22 | A2-44 | A2-148 | — | 1:1:0:1 | — |
| Cu2-23 | A2-10 | — | A1-1 | 2:0:2:0 | — |
| Cu2-24 | A2-1 | A2-44 | A1-3 | 1:1:1:1 | — |
| Cu2-25 | A2-1 | A2-44 | A1-16 | 1:1:1:1 | — |
| Cu2-26 | A2-1 | A2-44 | A1-22 | 1:1:1:1 | — |
| Cu2-27 | A2-1 | A2-44 | A1-23 | 1:1:1:1 | — |
| Cu2-28 | A2-1 | A2-44 | A1-27 | 1:1:1:1 | — |

TABLE 4

| Copper complex | Ligand Compound (A) (1) | Unidentate ligand (2) | (1):(2):Cu (II) Molar ratio | Counter ion |
|---|---|---|---|---|
| Cu3-1 | A3-1 | A1-1 | 1:2:1 | — |
| Cu3-2 | A3-2 | A1-1 | 1:2:1 | — |
| Cu3-3 | A3-6 | A1-1 | 1:2:1 | — |
| Cu3-4 | A3-16 | A1-1 | 1:2:1 | — |
| Cu3-5 | A3-20 | A1-1 | 1:2:1 | — |
| Cu3-6 | A3-23 | A1-1 | 1:2:1 | — |
| Cu3-7 | A3-24 | A1-1 | 1:2:1 | — |
| Cu3-8 | A3-25 | A1-1 | 1:1:1 | CuCl$_3$ |
| Cu3-9 | A3-28 | A1-1 | 1:2:1 | — |
| Cu3-10 | A3-43 | A1-1 | 1:2:1 | — |
| Cu3-11 | A3-44 | A1-1 | 1:2:1 | — |
| Cu3-12 | A3-45 | A1-1 | 1:2:1 | — |
| Cu3-13 | A3-46 | A1-1 | 1:2:1 | — |
| Cu3-14 | A3-50 | A1-1 | 1:2:1 | — |
| Cu3-15 | A3-52 | A1-1 | 1:2:1 | — |
| Cu3-16 | A3-54 | A1-1 | 1:2:1 | — |
| Cu3-17 | A3-56 | A1-1 | 1:2:1 | — |
| Cu3-18 | A3-58 | A1-1 | 1:2:1 | — |
| Cu3-19 | A3-59 | A1-1 | 1:2:1 | — |
| Cu3-20 | A3-60 | A1-1 | 1:2:1 | — |
| Cu3-21 | A3-69 | A1-1 | 1:2:1 | — |
| Cu3-22 | A3-73 | A1-1 | 1:2:1 | — |
| Cu3-23 | A3-96 | A1-1 | 1:2:1 | — |
| Cu3-24 | A3-97 | A1-1 | 1:2:1 | — |
| Cu3-25 | A3-98 | A1-1 | 1:2:1 | — |
| Cu3-26 | A3-99 | A1-1 | 1:2:1 | — |
| Cu3-27 | A3-100 | A1-1 | 1:2:1 | — |
| Cu3-28 | A3-103 | A1-1 | 1:2:1 | — |
| Cu3-29 | A3-105 | A1-1 | 1:2:1 | — |
| Cu3-30 | A3-106 | A1-1 | 1:2:1 | — |
| Cu3-31 | A3-113 | A1-1 | 1:2:1 | — |
| Cu3-32 | A3-125 | A1-1 | 1:2:1 | — |
| Cu3-33 | A3-127 | A1-1 | 1:2:1 | — |
| Cu3-34 | A3-131 | A1-1 | 1:2:1 | — |
| Cu3-35 | A3-135 | A1-1 | 1:2:1 | — |

TABLE 5

| Copper complex | Ligand Compound (A) (1) | Unidentate ligand (2) | (1):(2):Cu (II) Molar ratio | Counter ion |
|---|---|---|---|---|
| Cu3-36 | A3-140 | A1-1 | 1:2:1 | — |
| Cu3-37 | A1-141 | A1-1 | 1:1:1 | — |
| Cu3-38 | A3-2 | A1-23 | 1:2:1 | — |
| Cu3-39 | A3-24 | A1-23 | 1:2:1 | — |
| Cu3-40 | A3-43 | A1-23 | 1:2:1 | — |
| Cu3-41 | A3-24 | A1-2 | 1:2:1 | — |
| Cu3-42 | A3-43 | A1-2 | 1:2:1 | — |
| Cu3-43 | A3-24 | A1-31 | 1:2:1 | — |
| Cu3-44 | A3-43 | A1-31 | 1:2:1 | — |
| Cu3-45 | A3-24 | A1-34 | 1:2:1 | — |
| Cu3-46 | A3-43 | A1-34 | 1:2:1 | — |
| Cu3-47 | A3-24 | A1-35 | 1:2:1 | — |
| Cu3-48 | A3-43 | A1-35 | 1:2:1 | — |
| Cu3-49 | A3-24 | A1-36 | 1:2:1 | — |
| Cu3-50 | A3-43 | A1-36 | 1:2:1 | — |
| Cu3-51 | A3-24 | A1-39 | 1:2:1 | — |

TABLE 5-continued

| Copper complex | Ligand Compound (A) (1) | Unidentate ligand (2) | (1):(2):Cu (II) Molar ratio | Counter ion |
|---|---|---|---|---|
| Cu3-52 | A3-43 | A1-39 | 1:2:1 | — |
| Cu3-53 | A3-59 | A1-51 | 1:2:1 | — |
| Cu3-54 | A3-59 | A1-55 | 1:2:1 | — |
| Cu3-55 | A3-2 | A1-22 | 1:2:1 | — |
| Cu3-56 | A3-2 | A1-26 | 1:2:1 | — |
| Cu3-57 | A3-24 | A1-16 | 1:2:1 | — |
| Cu3-58 | A3-43 | A1-16 | 1:2:1 | — |
| Cu3-59 | A3-135 | A1-16 | 1:2:1 | — |
| Cu3-60 | A3-24 | A1-22 | 1:2:1 | — |
| Cu3-61 | A3-43 | A1-22 | 1:2:1 | — |
| Cu3-62 | A3-135 | A1-22 | 1:2:1 | — |
| Cu3-63 | A3-135 | A1-23 | 1:2:1 | — |
| Cu3-64 | A3-24 | A1-24 | 1:2:1 | — |
| Cu3-65 | A3-43 | A1-24 | 1:2:1 | — |
| Cu3-66 | A3-135 | A1-24 | 1:2:1 | — |
| Cu3-67 | A3-24 | A1-26 | 1:2:1 | — |
| Cu3-68 | A3-43 | A1-26 | 1:2:1 | — |
| Cu3-69 | A3-135 | A1-26 | 1:2:1 | — |

TABLE 6

| Copper complex | Ligand Compound (A) (1) | Compound (A) (2) | (1):(2):Cu (II) Molar ratio | Counter ion |
|---|---|---|---|---|
| Cu4-1 | A3-1 | A2-214 | 1:1:1 | — |
| Cu4-2 | A3-2 | A2-214 | 1:1:1 | — |
| Cu4-3 | A3-6 | A2-214 | 1:1:1 | — |
| Cu4-4 | A3-16 | A2-214 | 1:1:1 | — |
| Cu4-5 | A3-20 | A2-214 | 1:1:1 | — |
| Cu4-6 | A3-23 | A2-214 | 1:1:1 | — |
| Cu4-7 | A3-24 | A2-214 | 1:1:1 | — |
| Cu4-8 | A3-25 | A2-214 | 1:1:1 | — |
| Cu4-9 | A3-28 | A2-214 | 1:1:1 | — |
| Cu4-10 | A3-43 | A2-214 | 1:1:1 | — |
| Cu4-11 | A3-44 | A2-214 | 1:1:1 | — |
| Cu4-12 | A3-45 | A2-214 | 1:1:1 | — |
| Cu4-13 | A3-46 | A2-214 | 1:1:1 | — |
| Cu4-14 | A3-50 | A2-214 | 1:1:1 | — |
| Cu4-15 | A3-52 | A2-214 | 1:1:1 | — |
| Cu4-16 | A3-54 | A2-214 | 1:1:1 | — |
| Cu4-17 | A3-56 | A2-214 | 1:1:1 | — |
| Cu4-18 | A3-58 | A2-214 | 1:1:1 | — |
| Cu4-19 | A3-25 | A2-215 | 1:1:1 | — |
| Cu4-20 | A3-43 | A2-215 | 1:1:1 | — |
| Cu4-21 | A3-135 | A2-215 | 1:1:1 | — |
| Cu4-22 | A3-25 | A2-225 | 1:1:1 | — |
| Cu4-23 | A3-43 | A2-225 | 1:1:1 | — |
| Cu4-24 | A3-135 | A2-225 | 1:1:1 | — |
| Cu4-25 | A3-43 | A2-230 | 1:1:1 | — |
| Cu4-26 | A3-135 | A2-230 | 1:1:1 | — |
| Cu4-27 | A3-43 | A2-237 | 1:1:1 | — |
| Cu4-28 | A3-135 | A2-239 | 1:1:1 | — |
| Cu4-29 | A3-59 | A2-2 | 1:1:1 | — |
| Cu4-30 | A3-69 | A2-2 | 1:1:1 | — |
| Cu4-31 | A3-96 | A2-2 | 1:1:1 | — |
| Cu4-32 | A3-59 | A2-10 | 1:1:1 | — |
| Cu4-33 | A3-69 | A2-10 | 1:1:1 | — |
| Cu4-34 | A3-96 | A2-10 | 1:1:1 | — |
| Cu4-35 | A3-98 | A2-10 | 1:1:1 | — |

TABLE 7

| Copper complex | Ligand Compound (A) (1) | Compound (A) (2) | (1):(2):Cu (II) Molar ratio | Counter ion |
|---|---|---|---|---|
| Cu4-36 | A3-59 | A2-15 | 1:1:1 | — |
| Cu4-37 | A3-69 | A2-15 | 1:1:1 | — |
| Cu4-38 | A3-96 | A2-15 | 1:1:1 | — |
| Cu4-39 | A3-59 | A2-22 | 1:1:1 | — |
| Cu4-40 | A3-69 | A2-22 | 1:1:1 | — |
| Cu4-41 | A3-96 | A2-22 | 1:1:1 | — |
| Cu4-42 | A3-59 | A2-23 | 1:1:1 | — |
| Cu4-43 | A3-69 | A2-23 | 1:1:1 | — |
| Cu4-44 | A3-96 | A2-23 | 1:1:1 | — |
| Cu4-45 | A3-59 | A2-32 | 1:1:1 | — |
| Cu4-46 | A3-60 | A2-32 | 1:1:1 | — |
| Cu4-47 | A3-69 | A2-32 | 1:1:1 | — |
| Cu4-48 | A3-73 | A2-32 | 1:1:1 | — |
| Cu4-49 | A3-96 | A2-32 | 1:1:1 | — |
| Cu4-50 | A3-97 | A2-32 | 1:1:1 | — |
| Cu4-51 | A3-98 | A2-32 | 1:1:1 | — |
| Cu4-52 | A3-103 | A2-32 | 1:1:1 | — |
| Cu4-53 | A3-105 | A2-32 | 1:1:1 | — |
| Cu4-54 | A3-106 | A2-32 | 1:1:1 | — |
| Cu4-55 | A3-59 | A2-36 | 1:1:1 | — |
| Cu4-56 | A3-69 | A2-36 | 1:1:1 | — |
| Cu4-57 | A3-96 | A2-36 | 1:1:1 | — |
| Cu4-58 | A3-99 | A2-67 | 1:1:1 | — |
| Cu4-59 | A3-99 | A2-76 | 1:1:1 | — |
| Cu4-60 | A3-100 | A2-67 | 1:1:1 | — |
| Cu4-61 | A3-100 | A2-76 | 1:1:1 | — |
| Cu4-62 | A3-59 | A2-26 | 1:1:1 | — |
| Cu4-63 | A3-59 | A2-28 | 1:1:1 | — |
| Cu4-64 | A3-74 | A2-22 | 1:1:1 | — |
| Cu4-65 | A3-75 | A2-22 | 1:1:1 | — |
| Cu4-66 | A3-81 | A2-22 | 1:1:1 | — |

TABLE 8

| Copper complex | Ligand Compound (A) (1) | Unidentate ligand (2) | (1):(2):Cu (II) | Counter ion |
|---|---|---|---|---|
| Cu5-1 | A4-1 | A1-1 | 1:1:1 | Cl |
| Cu5-2 | A4-2 | A1-1 | 1:1:1 | Cl |
| Cu5-3 | A4-6 | A1-1 | 1:1:1 | Cl |
| Cu5-4 | A4-7 | A1-1 | 1:1:1 | Cl |
| Cu5-5 | A4-8 | A1-1 | 1:1:1 | Cl |
| Cu5-6 | A4-9 | A1-1 | 1:1:1 | Cl |
| Cu5-7 | A4-10 | A1-1 | 1:1:1 | Cl |
| Cu5-8 | A4-13 | A1-1 | 1:1:1 | Cl |
| Cu5-9 | A4-29 | A1-1 | 1:1:1 | Cl |
| Cu5-10 | A4-34 | A1-1 | 1:1:1 | Cl |
| Cu5-11 | A4-36 | A1-1 | 1:1:1 | Cl |
| Cu5-12 | A4-37 | A1-1 | 1:1:1 | Cl |
| Cu5-13 | A4-38 | A1-1 | 1:1:1 | Cl |
| Cu5-14 | A4-39 | A1-1 | 1:1:1 | Cl |
| Cu5-15 | A4-41 | A1-1 | 1:1:1 | Cl |
| Cu5-16 | A4-47 | A1-1 | 1:1:1 | Cl |
| Cu5-17 | A4-52 | A1-1 | 1:1:1 | Cl |
| Cu5-18 | A4-61 | A1-1 | 1:1:1 | Cl |
| Cu5-19 | A4-62 | A1-1 | 1:1:1 | Cl |
| Cu5-20 | A4-63 | A1-1 | 1:1:1 | Cl |
| Cu5-21 | A4-64 | A1-1 | 1:1:1 | Cl |
| Cu5-22 | A4-65 | A1-1 | 1:1:1 | Cl |
| Cu5-23 | A4-70 | A1-1 | 1:1:1 | Cl |
| Cu5-24 | A4-74 | A1-1 | 1:1:1 | Cl |
| Cu5-25 | A4-77 | A1-1 | 1:1:1 | Cl |
| Cu5-26 | A4-80 | A1-1 | 1:1:1 | Cl |
| Cu5-27 | A4-81 | A1-1 | 1:1:1 | Cl |
| Cu5-28 | A4-89 | A1-1 | 1:1:1 | Cl |
| Cu5-29 | A4-91 | A1-1 | 1:1:1 | Cl |
| Cu5-30 | A4-92 | A1-1 | 1:1:1 | Cl |

TABLE 9

| Copper complex | Ligand Compound (A) (1) | Unidentate ligand (2) | (1):(2):Cu (II) | Counter ion |
|---|---|---|---|---|
| Cu5-31 | A4-93 | A1-1 | 1:1:1 | Cl |
| Cu5-32 | A4-94 | A1-1 | 1:1:1 | Cl |
| Cu5-33 | A4-95 | A1-1 | 1:1:1 | Cl |
| Cu5-34 | A4-97 | A1-1 | 1:1:1 | Cl |
| Cu5-35 | A4-100 | A1-1 | 1:1:1 | Cl |
| Cu5-36 | A4-103 | A1-1 | 1:1:1 | Cl |
| Cu5-37 | A4-121 | A1-1 | 1:1:1 | — |
| Cu5-38 | A4-125 | A1-1 | 1:1:1 | — |
| Cu5-39 | A4-137 | A1-1 | 1:1:1 | — |
| Cu5-40 | A4-140 | A1-1 | 1:1:1 | — |
| Cu5-41 | A4-143 | A1-1 | 1:1:1 | — |
| Cu5-42 | A4-152 | A1-1 | 1:1:1 | Cl |
| Cu5-43 | A4-168 | A1-1 | 1:1:1 | Cl |
| Cu5-44 | A4-173 | A1-1 | 1:1:1 | Cl |
| Cu5-45 | A4-1 | A1-2 | 1:1:1 | Br |
| Cu5-46 | A4-1 | A1-41 | 1:1:1 | $SO_4$ |
| Cu5-47 | A4-1 | A1-23 | 1:1:1 | $OCOCH_3$ |
| Cu5-48 | A4-63 | A1-23 | 1:1:1 | $OCOCH_3$ |
| Cu5-49 | A4-1 | A1-28 | 1:1:1 | $NO_3$ |
| Cu5-50 | A4-61 | A1-41 | 1:1:1 | $SO_4$ |
| Cu5-51 | A4-62 | A1-41 | 1:1:1 | $(SO_4)_{0.5}$ |
| Cu5-52 | A4-63 | A1-41 | 1:1:1 | $(SO_4)_{0.5}$ |
| Cu5-53 | A4-1 | A1-35 | 1:1:1 | $(SO_4)_{0.5}$ |
| Cu5-54 | A4-61 | A1-35 | 1:1:1 | $(SO_4)_{0.5}$ |
| Cu5-55 | A4-62 | A1-35 | 1:1:1 | $(SO_4)_{0.5}$ |
| Cu5-56 | A4-63 | A1-35 | 1:1:1 | $(SO_4)_{0.5}$ |
| Cu5-57 | A4-1 | A1-36 | 1:1:1 | $(SO_4)_{0.5}$ |
| Cu5-58 | A4-61 | A1-36 | 1:1:1 | $(SO_4)_{0.5}$ |
| Cu5-59 | A4-62 | A1-36 | 1:1:1 | $(SO_4)_{0.5}$ |
| Cu5-60 | A4-63 | A1-36 | 1:1:1 | $(SO_4)_{0.5}$ |

TABLE 10

| Copper complex | Ligand Compound (A) (1) | Unidentate ligand (2) | (1):(2):Cu (II) | Counter ion |
|---|---|---|---|---|
| Cu5-61 | A4-1 | A1-9 | 1:1:1 | $(SO_4)_{0.5}$ |
| Cu5-62 | A4-61 | A1-11 | 1:1:1 | $(SO_4)_{0.5}$ |
| Cu5-63 | A4-62 | A1-22 | 1:1:1 | $(SO_4)_{0.5}$ |
| Cu5-64 | A4-63 | A1-26 | 1:1:1 | $(SO_4)_{0.5}$ |
| Cu5-65 | A4-1 | A1-28 | 1:1:1 | $(SO_4)_{0.5}$ |
| Cu5-66 | A4-1 | A1-32 | 1:1:1 | $(SO_4)_{0.5}$ |
| Cu5-67 | A4-1 | A1-33 | 1:1:1 | $(SO_4)_{0.5}$ |
| Cu5-68 | A4-1 | A1-34 | 1:1:1 | $(SO_4)_{0.5}$ |
| Cu5-69 | A4-1 | A1-39 | 1:1:1 | $(SO_4)_{0.5}$ |
| Cu5-70 | A4-177 | — | 1:0:1 | — |
| Cu5-71 | A4-180 | A1-1 | 1:1:1 | — |
| Cu5-72 | A4-1 | A1-1 | 1:1:1 | $BF_4$ |
| Cu5-73 | A4-61 | A1-1 | 1:1:1 | $BF_4$ |
| Cu5-74 | A4-62 | A1-1 | 1:1:1 | $BF_4$ |
| Cu5-75 | A4-63 | A1-1 | 1:1:1 | $BF_4$ |
| Cu5-76 | A4-1 | A1-1 | 1:1:1 | $BPh_4$ |
| Cu5-77 | A4-61 | A1-1 | 1:1:1 | $BPh_4$ |
| Cu5-78 | A4-62 | A1-1 | 1:1:1 | $BPh_4$ |
| Cu5-79 | A4-63 | A1-1 | 1:1:1 | $BPh_4$ |
| Cu5-80 | A4-1 | A1-1 | 1:1:1 | $B(C_6F_5)_4$ |
| Cu5-81 | A4-61 | A1-1 | 1:1:1 | $B(C_6F_5)_4$ |
| Cu5-82 | A4-62 | A1-1 | 1:1:1 | $B(C_6F_5)_4$ |
| Cu5-83 | A4-63 | A1-1 | 1:1:1 | $B(C_6F_5)_4$ |
| Cu5-84 | A4-1 | A1-1 | 1:1:1 | $PF_6$ |
| Cu5-85 | A4-61 | A1-1 | 1:1:1 | $PF_6$ |
| Cu5-86 | A4-62 | A1-1 | 1:1:1 | $PF_6$ |
| Cu5-87 | A4-63 | A1-1 | 1:1:1 | $PF_6$ |
| Cu5-88 | A4-1 | A1-1 | 1:1:1 | $B(CN)_4$ |
| Cu5-89 | A4-61 | A1-1 | 1:1:1 | $B(CN)_4$ |
| Cu5-90 | A4-62 | A1-1 | 1:1:1 | $B(CN)_4$ |
| Cu5-91 | A4-63 | A1-1 | 1:1:1 | $B(CN)_4$ |
| Cu5-92 | A4-1 | A1-1 | 1:1:1 | $N(SO_2CF_3)_2$ |
| Cu5-93 | A4-61 | A1-1 | 1:1:1 | $N(SO_2CF_3)_2$ |
| Cu5-94 | A4-62 | A1-1 | 1:1:1 | $N(SO_2CF_3)_2$ |
| Cu5-95 | A4-63 | A1-1 | 1:1:1 | $N(SO_2CF_3)_2$ |
| Cu5-96 | A4-61 | A1-2 | 1:1:1 | Br |
| Cu5-97 | A4-188 | A1-1 | 1:1:1 | $B(C_6F_5)_4$ |
| Cu5-98 | A4-63 | A1-1 | 1:1:1 | $C(SO_2CF_3)_3$ |
| Cu5-99 | A4-63 | A1-23 | 1:1:1 | $B(C_6F_5)_4$ |
| Cu5-100 | A4-63 | A1-2 | 1:1:1 | $B(C_6F_5)_4$ |

TABLE 11

| Copper complex | Ligand Compound (A)(1) | Unidentate ligand(2) | (1):(2):Cu(II) | Counter ion |
|---|---|---|---|---|
| Cu5-101 | A4-1 | A1-11 | 1:1:1 | $B(C_6F_5)_4$ |
| Cu5-102 | A4-1 | A1-23 | 1:1:1 | $B(C_6F_5)_4$ |
| Cu5-103 | A4-1 | A1-24 | 1:1:1 | $B(C_6F_5)_4$ |
| Cu5-104 | A4-63 | A1-41 | 1:1:1 | $[N(SO_2CF_3)_2]_2$ |
| Cu5-105 | A4-65 | A1-1 | 1:1:1 | $BF_4$ |
| Cu5-106 | A4-90 | A1-1 | 1:1:1 | Cl |
| Cu5-107 | A4-189 | A1-1 | 1:1:1 | Cl |
| Cu5-108 | A4-190 | A1-1 | 1:1:1 | Cl |
| Cu5-109 | A4-191 | A1-1 | 1:1:1 | Cl |
| Cu5-110 | A4-192 | A1-1 | 1:1:1 | Cl |
| Cu5-111 | A4-193 | A1-1 | 1:1:1 | Cl |
| Cu5-112 | A4-194 | A1-1 | 1:1:1 | Cl |
| Cu5-113 | A4-195 | A1-1 | 1:1:1 | Cl |
| Cu5-114 | A4-196 | A1-1 | 1:1:1 | Cl |
| Cu5-115 | A4-63 | A1-1 | 1:1:1 | $[Cu(dpa)_2]_{0.5}$ |
| Cu5-116 | A4-63 | A1-41 | 1:1:1 | $Cu(dpa)_2$ |
| Cu5-117 | A4-29 | A1-1 | 1:1:1 | $BF_4$ |
| Cu5-118 | A4-65 | A1-1 | 1:1:1 | $B(C_6F_5)_4$ |
| Cu5-119 | A4-65 | A1-41 | 1:1:1 | $SO_4$ |
| Cu5-120 | A4-63 | A1-1 | 1:1:1 | $N(SO_2CF_2CF_3)_2$ |
| Cu5-121 | A4-63 | A1-1 | 1:1:1 | $N(SO_2CF_2CF_2CF_2CF_3)_2$ |
| Cu5-122 | A4-63 | A1-1 | 1:1:1 | cyclic imide (structure shown) |
| Cu5-123 | A4-216 | A1-1 | 1:1:1 | $B(C_6F_5)_4$ |
| Cu5-124 | A4-216 | A1-1 | 1:1:1 | $N(SO_2CF_3)_2$ |
| Cu5-125 | A4-217 | A1-1 | 1:1:1 | $B(C_6F_5)_4$ |
| Cu5-126 | A4-217 | A1-1 | 1:1:1 | $N(SO_2CF_3)_2$ |

$Cu(dpa)_2$ = [dipicolinate copper complex, 2− charge]

TABLE 12

| Copper complex | Ligand Compound (A)(1) | Unidentate ligand(2) | (1):(2):Cu(II) | Counter ion |
|---|---|---|---|---|
| Cu5-127 | A4-63 | A1-58 | 1:1:1 | $B(C_6F_5)_4$ |
| Cu5-128 | A4-63 | A1-59 | 1:1:1 | $B(C_6F_5)_4$ |
| Cu5-129 | A4-63 | A1-60 | 1:1:1 | $B(C_6F_5)_4$ |
| Cu5-130 | A4-63 | A1-61 | 1:1:1 | $B(C_6F_5)_4$ |
| Cu5-131 | A4-63 | A1-62 | 1:1:1 | $B(C_6F_5)_4$ |
| Cu5-132 | A4-63 | A1-63 | 1:1:1 | $B(C_6F_5)_4$ |
| Cu5-133 | A4-63 | A1-64 | 1:1:1 | $B(C_6F_5)_4$ |
| Cu5-134 | A4-63 | A1-65 | 1:1:1 | $B(C_6F_5)_4$ |
| Cu5-135 | A4-63 | A1-66 | 1:1:1 | $B(C_6F_5)_4$ |
| Cu5-136 | A4-63 | A1-23 | 1:1:1 | 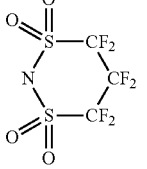 |
| Cu5-137 | A4-63 | A1-23 | 1:1:1 | $PF_6$ |
| Cu5-138 | A4-63 | A1-24 | 1:1:1 | PhCOO |
| Cu5-139 | A4-63 | A1-24 | 1:1:1 | $C_4F_9SO_3$ |
| Cu5-140 | A4-63 | A1-24 | 1:1:1 | $N(SO_2CF_3)_2$ |
| Cu5-141 | A4-63 | A1-24 | 1:1:1 | 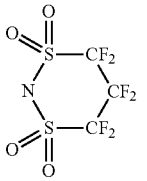 |
| Cu5-142 | A4-63 | A1-24 | 1:1:1 | $C(SO_2CF_3)_3$ |
| Cu5-143 | A4-63 | A1-24 | 1:1:1 | $PF_6$ |
| Cu5-144 | A4-63 | A1-58 | 1:1:1 | 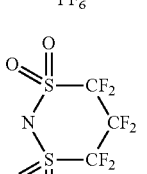 |
| Cu5-145 | A4-63 | A1-58 | 1:1:1 | $C(SO_2CF_3)_3$ |
| Cu5-146 | A4-63 | A1-58 | 1:1:1 | $PF_6$ |
| Cu5-147 | A4-63 | A1-59 | 1:1:1 | (same cyclic structure) |
| Cu5-148 | A4-63 | A1-59 | 1:1:1 | $C(SO_2CF_3)_3$ |
| Cu5-149 | A4-63 | A1-59 | 1:1:1 | $PF_6$ |
| Cu5-150 | A4-63 | A1-60 | 1:1:1 | (same cyclic structure) |
| Cu5-151 | A4-63 | A1-60 | 1:1:1 | $C(SO_2CF_3)_3$ |
| Cu5-152 | A4-63 | A1-60 | 1:1:1 | $PF_6$ |

TABLE 13

| Copper complex | Ligand Compound (A) (1) | (1):Cu (II) | Counter ion |
|---|---|---|---|
| Cu6-1 | A5-2 | 1:1 | $(Cl)_2$ |
| Cu6-2 | A5-6 | 1:1 | $(Cl)_2$ |
| Cu6-3 | A5-7 | 1:1 | $(Cl)_2$ |
| Cu6-4 | A5-8 | 1:1 | Cl |
| Cu6-5 | A5-9 | 1:1 | $(Cl)_2$ |
| Cu6-6 | A5-13 | 1:1 | $(Cl)_2$ |
| Cu6-7 | A5-15 | 1:1 | — |
| Cu6-8 | A5-19 | 1:1 | $(Cl)_2$ |
| Cu6-9 | A5-20 | 1:1 | $(Cl)_2$ |
| Cu6-10 | A5-21 | 1:1 | $(Cl)_2$ |
| Cu6-11 | A5-2 | 1:1 | $(OH)_2$ |
| Cu6-12 | A5-2 | 1:1 | $(OCOCH_3)_2$ |
| Cu6-13 | A5-2 | 1:1 | $SO_4$ |
| Cu6-14 | A5-2 | 1:1 | $(NO_3)_2$ |
| Cu6-15 | A5-2 | 1:1 | $(ClO_4)_2$ |
| Cu6-16 | A5-2 | 1:1 | $(Br)_2$ |
| Cu6-17 | A5-2 | 1:1 | $(BF_4)_2$ |
| Cu6-18 | A5-7 | 1:1 | $(BF_4)_2$ |
| Cu6-19 | A5-8 | 1:1 | $BF_4$ |
| Cu6-20 | A5-13 | 1:1 | $(BF_4)_2$ |
| Cu6-21 | A5-2 | 1:1 | $(BPh_4)_2$ |
| Cu6-22 | A5-7 | 1:1 | $(BPh_4)_2$ |
| Cu6-23 | A5-8 | 1:1 | $BPh_4$ |
| Cu6-24 | A5-13 | 1:1 | $(BPh_4)_2$ |
| Cu6-25 | A5-2 | 1:1 | $[B(C_6F_5)_4]_2$ |
| Cu6-26 | A5-7 | 1:1 | $[B(C_6F_5)_4]_2$ |
| Cu6-27 | A5-8 | 1:1 | $B(C_6F_5)_4$ |
| Cu6-28 | A5-13 | 1:1 | $[B(C_6F_5)_4]_2$ |
| Cu6-29 | A5-2 | 1:1 | $(PF_6)_2$ |
| Cu6-30 | A5-7 | 1:1 | $(PF_6)_2$ |

TABLE 14

| Copper complex | Ligand Compound (A) (1) | (1):Cu (II) | Counter ion |
|---|---|---|---|
| Cu6-31 | A5-8 | 1:1 | $PF_6$ |
| Cu6-32 | A5-13 | 1:1 | $(PF_6)_2$ |
| Cu6-33 | A5-2 | 1:1 | $[B(CN)_4]_2$ |
| Cu6-34 | A5-7 | 1:1 | $[B(CN)_4]_2$ |
| Cu6-35 | A5-8 | 1:1 | $B(CN)_4$ |
| Cu6-36 | A5-13 | 1:1 | $[B(CN)_4]_2$ |
| Cu6-37 | A5-22 | 1:1 | $(Cl)_2$ |
| Cu6-38 | A5-23 | 1:1 | $(Cl)_2$ |
| Cu6-39 | A5-24 | 1:1 | $(Cl)_2$ |
| Cu6-40 | A5-25 | 1:1 | $(Cl)_2$ |
| Cu6-41 | A5-26 | 1:1 | $(Cl)_2$ |
| Cu6-42 | A5-27 | 1:1 | $(Cl)_2$ |
| Cu6-43 | A5-28 | 1:1 | $(Cl)_2$ |
| Cu6-44 | A5-29 | 1:1 | $(Cl)_2$ |
| Cu6-45 | A5-30 | 1:1 | $(Cl)_2$ |
| Cu6-46 | A5-31 | 1:1 | $(Cl)_2$ |
| Cu6-47 | A5-33 | 1:1 | $(Cl)_2$ |
| Cu6-48 | A5-33 | 1:1 | $[B(C_6F_5)_4]_2$ |
| Cu6-49 | A5-33 | 1:1 | $[N(SO_2CF_3)_2]_2$ |
| Cu6-50 | A5-33 | 1:1 | $SO_4$ |
| Cu6-51 | A5-37 | 1:1 | Cl |
| Cu6-52 | A5-37 | 1:1 | $B(C_6F_5)_4$ |
| Cu6-53 | A5-37 | 1:1 | $N(SO_2CF_3)_2$ |

A content of the copper complex of the near infrared ray absorbent composition of the present invention (the same applies to a copper complex formed by reacting the compound (A) and a copper component) is preferably greater than or equal to 1 mass %, and more preferably greater than or equal to 5 mass %, with respect to the content of the near infrared ray absorbent composition of the present invention (including a solvent). The upper limit thereof is, for example, preferably less than or equal to 60 mass %, more preferably less than or equal to 40 mass %, and even more preferably less than or equal to 20 mass %.

The content of the copper complex of the near infrared ray absorbent composition of the present invention is preferably greater than or equal to 15 mass %, more preferably greater than or equal to 20 mass %, and even more preferably greater than or equal to 25 mass %, with respect to the total solid content of the composition. The upper limit thereof is, for example, preferably less than or equal to 60 mass %, more preferably less than or equal to 50 mass %, and even more preferably less than or equal to 45 mass %.

A percentage of the compound formed with a reaction between the compound (A) and the copper component in near infrared ray absorbent substances included in the near infrared ray absorbent composition of the present invention is preferably greater than or equal to 80 mass %, more preferably greater than or equal to 90 mass %, and even more preferably greater than or equal to 95 mass %.

The content of copper of the near infrared ray absorbent composition of the present invention is preferably greater than or equal to 0.1 mass %, more preferably greater than or equal to 1 mass %, and even more preferably greater than or equal to 5 mass %, with respect to the total solid content of the composition. The upper limit thereof is preferably less than or equal to 30 mass %, more preferably less than or equal to 20 mass %, and even more preferably less than or equal to 15 mass %.

The total solid content of the near infrared ray absorbent composition of the present invention is preferably greater than or equal to 1 mass % and more preferably greater than or equal to 10 mass % with respect to the content of the composition. The upper limit thereof is preferably less than or equal to 60 mass %, more preferably less than or equal to 40 mass %, and even more preferably less than or equal to 20 mass %.

In the near infrared ray absorbent composition of the present invention, only one type of the copper complex used in the present invention described above may be used, or two or more types thereof may be used together. In a case of using two or more types of the copper complex used in the present invention described above, the total amount thereof is preferably in the range described above.

<<Other Near Infrared Ray Absorbent Compounds>>

In the near infrared ray absorbent composition of the present invention, formulation of near infrared ray absorbent compounds other than the copper complex described above (hereinafter, also referred to as other near infrared ray absorbent compounds) may be performed in order to adjust film spectra.

In a case where the near infrared ray absorbent composition of the present invention includes the other near infrared ray absorbent compounds, a content of the other near infrared ray absorbent compounds is preferably greater than or equal to 0.01 mass %, more preferably greater than or equal to 1 mass %, and even more preferably greater than or equal to 5 mass % with respect to the total solid content of the near infrared ray absorbent composition of the present invention. The upper limit thereof is preferably less than or equal to 60 mass %, more preferably less than or equal to 40 mass %, and even more preferably less than or equal to 20 mass %. In addition, in the present invention, composition in which the other near infrared ray absorbent compounds are not included can also be used.

The other near infrared ray absorbent compounds are not particularly limited, as long as the maximum absorption wavelength range is in a range of 700 to 2,500 nm, and preferably 700 to 1,200 nm. For example, a copper complex having a maximum absorption wavelength in a wavelength range of 700 to 1,200 nm and in which a molar light absorption coefficient at the maximum absorption wavelength is smaller than 100 (L/mol·cm) and the like are used.

In addition, a pyrrolo pyrrole-based compound, a cyanine-based compound, a phthalocyanine-based compound (including a copper phthalocyanine complex), a naphthalocyanine-based compound, an immonium-based compound, a thiol complex-based compound, a transition metal oxide-based compound, a squarylium-based compound, a quaterrylene-based compound, a dithiol metal complex-based compound, a croconium-based compound, and the like can also be used.

The pyrrolo pyrrole-based compound may be a pigment, or may be a dye, and the pigment is preferable from the reason of easily forming a film having excellent heat resistance. Examples of the pyrrolo pyrrole-based compound include pyrrolo pyrrole compounds disclosed in paragraphs 0016 to 0058 of JP2009-263614A, and the like.

Compounds disclosed in paragraphs 0010 to 0081 of JP2010-111750A may be used as the cyanine-based compound, the phthalocyanine-based compound, the immonium-based compound, the squarylium-based compound, and the croconium-based compound, and the contents thereof are incorporated herein. In addition, the cyanine-based compound, for example, can be referred to "Functional Coloring Agent, written by OKAWARA Makoto/MATSUOKA Masaru/KITAO Teijiro/HIRASHIMA Tsuneaki and published by Kodansha Scientific Ltd.", and the contents thereof are incorporated herein. In addition, the phthalocyanine-based compound can be referred to the description in paragraphs 0013 to 0029 of JP2013-195480A, and the contents thereof are incorporated herein.

As the copper complex in which a molar light absorption coefficient is smaller than 100 (L/mol·cm), a low molecular type copper complex obtained by a reaction between the compound having a coordination portion and a copper component, and a polymer type copper complex obtained by a reaction between a polymer having a coordination portion (also referred to as a polymer (B)) and a copper component can be used.

<<Inorganic Fine Particles>>

The near infrared ray absorbent composition of the present invention may contain inorganic fine particles, in order to obtain desired near infrared ray shielding properties. Only one type of the inorganic fine particles may be used, or two or more types thereof may be used.

The inorganic fine particles are particles which mainly have a function of shielding (absorbing) an infrared ray. It is preferable that the inorganic fine particles are metal oxide fine particles or metal fine particles from the viewpoint of more excellent infrared ray shielding properties.

Examples of the metal oxide particles include indium tin oxide (ITO) particles, antimony tin oxide (ATO) particles, zinc oxide (ZnO) particles, Al-doped zinc oxide (Al-doped ZnO) particles, fluorine-doped tin dioxide (F-doped $SnO_2$) particles, niobium-doped titanium dioxide (Nb-doped $TiO_2$) particles, and the like.

Examples of the metal fine particles include silver (Ag) particles, gold (Au) particles, copper (Cu) particles, nickel (Ni) particles, and the like. Furthermore, in order to make infrared ray shielding properties and photolithographic properties compatible, it is desirable that a transmittance in an exposure wavelength (365 to 405 nm) is high, and thus, the indium tin oxide (ITO) particles or the antimony tin oxide (ATO) particles are preferable.

The shape of the inorganic fine particles is not particularly limited, and may be not only a spherical shape and a non-spherical shape, but also a sheet-like shape, a wire-like shape, and a tubular shape.

In addition, a tungsten oxide-based compound can be used as the inorganic fine particles, and specifically, a tungsten oxide-based compound represented by General Formula (Compositional Formula) (I) described below is more preferable.

$$M_xW_yO_z \tag{I}$$

M represents metal, W represents tungsten, and O represents oxygen.

$$0.001 \leq x/y \leq 1.1$$

$$2.2 \leq z/y \leq 3.0$$

Examples of the metal represented by M include alkali metal, alkali earth metal, Mg, Zr, Cr, Mn, Fe, Ru, Co, Rh, Ir, Ni, Pd, Pt, Cu, Ag, Au, Zn, Cd, Al, Ga, In, Tl, Sn, Pb, Ti, Nb, V, Mo, Ta, Re, Be, Hf, Os, and Bi, the alkali metal is preferable, Rb or Cs is more preferable, and Cs is particularly preferable. Only one type of the metals of M may be used or two or more types thereof may be used.

By setting x/y to be greater than or equal to 0.001, it is possible to sufficiently shield an infrared ray, and by setting X/Y to be less than or equal to 1.1, it is possible to reliably prevent an impurity phase from being generated in the tungsten oxide-based compound.

By setting z/y to be greater than or equal to 2.2, it is possible to further improve chemical stability as a material, and by setting z/y to be less than or equal to 3.0, it is possible to sufficiently shield an infrared ray.

Specific examples of the tungsten oxide-based compound represented by General Formula (I) described above can include $Cs_{0.33}WO_3$, $Rb_{0.33}WO_3$, $K_{0.33}WO_2$, $Ba_{0.33}WO_3$, and the like, $Cs_{0.33}WO_3$ or $Rb_{0.33}WO_3$ is preferable, and $Cs_{0.33}WO_3$ is more preferable.

The tungsten oxide-based compound, for example, can be available as a dispersion of tungsten fine particles such as YMF-02, YMF-02A, YMS-01A-2, or YMF-10A-1 manufactured by Sumitomo Metal Mining Co., Ltd.

The average particle diameter of the inorganic fine particles is preferably less than or equal to 800 nm, is more preferably less than or equal to 400 nm, and is even more preferably less than or equal to 200 nm. By setting the average particle diameter of the inorganic fine particles to be in such a range, it is possible to make light transmittance in a visible light range more reliable. It is preferable that the average particle diameter is small from the viewpoint of preventing light scattering, and the average particle diameter of the inorganic fine particles is generally greater than or equal to 1 nm from the reason of handling easiness or the like at the time of manufacturing.

The content of the inorganic fine particles is preferably 0.01 to 30 mass % with respect to the total solid content of the near infrared ray absorbent composition. The lower limit is preferably greater than or equal to 0.1 mass %, and is more preferably greater than or equal to 1 mass %. The upper limit is preferably less than or equal to 20 mass %, and is more preferably less than or equal to 10 mass %.

<<Solvent>>

The near infrared ray absorbent composition of the present invention may contain a solvent. The solvent is not particularly limited, and can be suitably selected according to the purpose, insofar as each component can be homogeneously dissolved or dispersed in the solvent. For example, water and an organic solvent can be used. In addition, water and an organic solvent can be used together.

Examples of the organic solvent preferably include alcohols, ketones, esters, aromatic hydrocarbons, halogenated hydrocarbons, dimethyl formamide, dimethyl acetamide, dimethyl sulfoxide, sulfolane, and the like. Only one type of the organic solvent may be used, or two or more types thereof may be used together.

Specific examples of the alcohols, the aromatic hydrocarbons, and the halogenated hydrocarbons include those described in paragraph 0136 of JP2012-194534A and the like, and the contents thereof are incorporated herein.

Specific examples of the esters, the ketones, and the ethers include those described in paragraph 0497 of JP2012-208494A ([0609] of the specification of corresponding US2012/0235099A). Further, the specific examples include n-amyl acetate, ethyl propionate, dimethyl phthalate, ethyl benzoate, methyl sulfate, acetone, methyl isobutyl ketone, diethyl ether, ethylene glycol monobutyl ether acetate, and the like.

It is preferable that at least one type selected from cyclopentanone, cyclohexanone, propylene glycol monomethyl ether acetate, N-methyl-2-pyrrolidone, butyl acetate, ethyl lactate, and propylene glycol monomethyl ether is used as the solvent.

The content of the solvent is preferably 5 to 60 mass %, and is more preferably 10 to 40 mass %, with respect to the total solid content of the near infrared ray absorbent composition of the present invention.

In addition, in a case where water and the organic solvent are used together, a mass ratio of water to the organic solvent is preferably 0.1:99.9 to 30:70, is more preferably 0.2:99.8 to 20:80, and is even more preferably 0.5:99.5 to 10:90.

Only one type of the solvent may be used, or two or more types thereof may be used, and in a case where two or more types of the solvents are used, it is preferable that the total amount is in the range described above.

<<Curable Compound>>

The near infrared ray absorbent composition of the present invention may contain a curable compound. The curable compound may be a compound having a polymerizable group or may be a non-polymerizable compound such as a binder. The curable compound may have any one of chemical forms such as a monomer, an oligomer, a prepolymer, and a polymer. The curable compound, for example, can be referred to the description of paragraphs 0070 to 0191 of JP2014-41318A (paragraphs 0071 to 0192 of the pamphlet of corresponding WO2014/017669A), paragraphs 0045 to 0216 of JP2014-32380A, and the like, and the contents thereof are incorporated herein.

Examples of the curable compound include a compound including a group having an ethylenically unsaturated bond, and a compound including a cyclic ether group (for example, an epoxy group, an oxetanyl group, and the like). As vinyl group, a styryl group, a (meth)acryloyl group, and a (meth)allyl group are preferable as the group having an ethylenically unsaturated bond. The compound including the group having an ethylenically unsaturated bond may be a monofunctional compound having one group described above, or may be a polyfunctional compound having two or more groups described above, and is preferably a polyfunctional compound. The near infrared ray absorbent composition contains the polyfunctional compound, and thus, heat resistance can be further improved.

Examples of the curable compound include monofunctional (meth)acrylate, polyfunctional (meth)acrylate (preferably trifunctional (meth)acrylate to hexafunctional (meth)

acrylate), a polybasic acid-modified acryl oligomer, an epoxy resin, a polyfunctional epoxy resin, and the like.

In the present invention, a compound having a partial structure represented by M-X can be used as the curable compound. M is an atom selected from Si, Ti, Zr, and Al. X is one type selected from a hydroxy group, an alkoxy group, an acyloxy group, a phosphoryloxy group, a sulfonyloxy group, an amino group, an oxime group, and O=C($R^a$)($R^b$). $R^a$ and $R^b$ each independently represent monovalent organic group.

A cured material obtained by the compound having a partial structure represented by M-X is crosslinked by a strong chemical bond, and thus, has excellent heat resistance. In addition, a mutual interaction with respect to the near infrared ray absorbent compound (in particular, a copper complex) is hardly generated, and thus, can suppress a decrease in properties of the near infrared ray absorbent compound. For this reason, it is possible to form a cured film having excellent heat resistance while maintaining high near infrared ray shielding properties.

In a case where the near infrared ray absorbent composition of the present invention contains the curable compound, the content of the curable compound is preferably 1 to 90 mass % with respect to the total solid content of the near infrared ray absorbent composition. The lower limit is preferably greater than or equal to 5 mass %, is more preferably greater than or equal to 10 mass %, and is even more preferably greater than or equal to 20 mass %. The upper limit is preferably less than or equal to 80 mass %, and is more preferably less than or equal to 75 mass %. In addition, in a case where a polymer which has a repeating unit having a polymerizable group is used as the curable compound, the content of the curable compound is preferably 10 to 75 mass % with respect to the total solid content of the near infrared ray absorbent composition. The lower limit is preferably greater than or equal to 20 mass %. The upper limit is preferably less than or equal to 65 mass %, and is more preferably less than or equal to 60 mass %.

Only one type of the curable compound may be used, or two or more types thereof may be used. In a case where two or more types of the curable compounds are used, it is preferable that the total amount is in the range described above.

It is possible that the near infrared ray absorbent composition of the present invention does not substantially contain the curable compound. "Not substantially containing the curable compound", for example, indicates that the content of the curable compound is preferably less than or equal to 0.5 mass %, and is more preferably less than or equal to 0.1 mass %, with respect to the total solid content of the near infrared ray absorbent composition, and it is even more preferable that the curable compound is not contained.

<<<Compound Including Group Having Ethylenically Unsaturated Bond>>>

In the present invention, a compound including a group having an ethylenically unsaturated bond can be used as the curable compound. Examples of the compound including a group having an ethylenically unsaturated bond can be referred to the description of paragraphs 0033 and 0034 of JP2013-253224A, and the contents thereof are incorporated herein.

Ethylene oxy-modified pentaerythritol tetraacrylate (NK ESTER ATM-35E; manufactured by Shin Nakamura Chemical Co., Ltd. as a commercially available product), dipentaerythritol triacrylate (KAYARAD D-330; manufactured by Nippon Kayaku Co., Ltd. as a commercially available product), dipentaerythritol tetraacrylate (KAY-ARAD D-320; manufactured by Nippon Kayaku Co., Ltd. as a commercially available product), dipentaerythritol penta(meth)acrylate (KAYARAD D-310; manufactured by Nippon Kayaku Co., Ltd. as a commercially available product), dipentaerythritol hexa(meth)acrylate (KAYARAD DPHA; manufactured by Nippon Kayaku Co., Ltd. and A-DPH-12E; manufactured by Shin Nakamura Chemical Co., Ltd. as commercially available products), and a structure in which (meth)acryloyl groups thereof interpose ethylene glycol and a propylene glycol residue therebetween are preferable as the compound including a group having an ethylenically unsaturated bond. In addition, oligomer type compounds thereof can also be used.

In addition, the compound can be referred to the description of a polymerizable compound of paragraphs 0034 to 0038 of JP2013-253224A, and the contents thereof are incorporated herein.

In addition, examples of the compound include a polymerizable monomer described in paragraph 0477 of JP2012-208494A ([0585] of the specification of corresponding US2012/0235099A), and the like, and the contents thereof are incorporated herein.

In addition, diglycerin ethylene oxide (EO)-modified (meth)acrylate (M-460; manufactured by TOAGOSEI CO., LTD. as a commercially available product) is preferable. Pentaerythritol tetraacrylate (manufactured by Shin Nakamura Chemical Co., Ltd., A-TMMT) and 1,6-hexanediol diacrylate (manufactured by Nippon Kayaku Co., Ltd., KAYARAD HDDA) are also preferable. Oligomer type compounds thereof are can also be used. For example, RP-1040 (manufactured by Nippon Kayaku Co., Ltd.) is included.

The compound including a group having an ethylenically unsaturated bond may have an acid group such as a carboxyl group, a sulfo group, and a phosphoric acid group.

Examples of the compound having an acid group include ester of an aliphatic polyhydroxy compound and an unsaturated carboxylic acid, and the like. A compound having an acid group by allowing a non-aromatic carboxylic acid anhydride to react with an unreacted hydroxyl group of the aliphatic polyhydroxy compound is preferable, and a compound in which the aliphatic polyhydroxy compound is pentaerythritol and/or dipentaerythritol in the ester described above is particularly preferable. Polybasic acid-modified acryl oligomer manufactured by TOAGOSEI CO., LTD. is a commercially available product, and examples thereof include M-305, M-510, and M-520 of ARONIX series, and the like.

An acid value of the compound having an acid group is preferably 0.1 to 40 mgKOH/g. The lower limit is preferably greater than or equal to 5 mgKOH/g. The upper limit is preferably less than or equal to 30 mgKOH/g.

<<<Compound Having Epoxy Group or Oxetanyl Group>>>

In the present invention, a compound having an epoxy group or an oxetanyl group can be used as the curable compound. Examples of the compound having an epoxy group or an oxetanyl group include a polymer having an epoxy group on a side chain, a monomer or an oligomer having two or more epoxy groups in the molecules, and the like. Examples of the compound can include a bisphenol A type epoxy resin, a bisphenol F type epoxy resin, a phenol novolac type epoxy resin, a cresol novolac type epoxy resin, an aliphatic epoxy resin, and the like. In addition, examples of the compound also include a monofunctional glycidyl ether compound or a polyfunctional glycidyl ether compound, and the polyfunctional aliphatic glycidyl ether compound is preferable.

The weight-average molecular weight thereof is preferably 500 to 5,000,000, and is more preferably 1,000 to 500,000.

A commercially available product may be used as the compound, or a compound obtained by introducing an epoxy group to the side chain of the polymer may be used.

A commercially available product, for example, can be referred to the description of paragraph 0191 of JP2012-155288A and the like, and the contents thereof are incorporated herein.

In addition, examples of the commercially available product include a polyfunctional aliphatic glycidyl ether compound such as DENACOL EX-212L, EX-214L, EX-216L, EX-321L, and EX-850L (which are manufactured by Nagase ChemteX Corporation.). The examples described above are low chlorine products, and EX-212, EX-214, EX-216, EX-321, EX-850, and the like, which are not low chlorine products, can also be used.

In addition, examples of the commercially available product include ADEKA RESIN EP-4000S, ADEKA RESIN EP-4003S, ADEKA RESIN EP-4010S, and ADEKA RESIN EP-4011S (which are manufactured by ADEKA CORPORATION), NC-2000, NC-3000, NC-7300, XD-1000, EPPN-501, and EPPN-502 (which are manufactured by ADEKA CORPORATION), JER1031S, CELLOXIDE 2021P, CELLOXIDE 2081, CELLOXIDE 2083, CELLOXIDE 2085, EHPE3150, EPOLEAD PB 3600, and EPOLEAD PB 4700 (which are manufactured by DAICEL CORPORATION.), CYCLOMER P ACA 200M, CYCLOMER ACA 230AA, CYCLOMER ACA Z250, CYCLOMER ACA Z251, CYCLOMER ACA Z300, and CYCLOMER ACA Z320 (which are manufactured by DAICEL CORPORATION.), and the like.

Further, examples of a commercially available product of the phenol novolac type epoxy resin include JER-157S65, JER-152, JER-154, and JER-157S70 (which are manufactured by Mitsubishi Chemical Corporation), and the like.

In addition, ARON OXETANE OXT-121, OXT-221, OX-SQ, and PNOX (which are manufactured by TOAGOSEI CO., LTD.) can be used as specific examples of the polymer having an oxetanyl group on the side chain, and the polymerizable monomer or the polymerizable oligomer having two or more oxetanyl groups in the molecules.

A compound having a glycidyl group as an epoxy group of glycidyl (meth)acrylate, allyl glycidyl ether, or the like can also be used as the compound having an epoxy group, and an unsaturated compound having an alicyclic epoxy group is preferable. Such compounds, for example, can be referred to the description of paragraph 0045 of JP2009-265518A, and the like, and the contents thereof are incorporated herein.

The compound having an epoxy group or an oxetanyl group may include a polymer having an epoxy group or an oxetanyl group as a repeating unit. Specifically, examples of the polymer include polymers (copolymers) having repeating units described below.

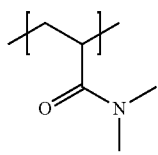

-continued

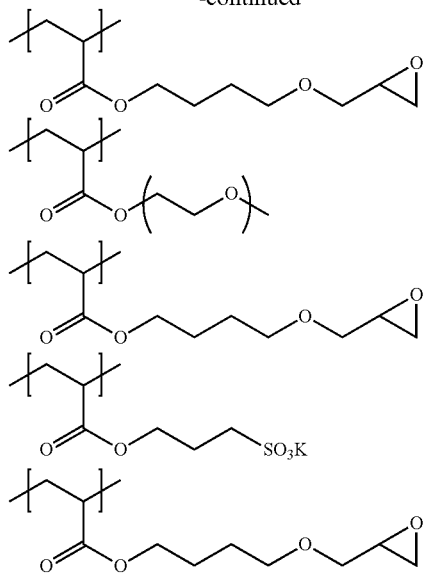

<<<Compound Having Partial Structure Represented by M-X>>>

In the present invention, a compound having a partial structure represented by M-X can be used as the curable compound.

M is an atom selected from Si, Ti, Zr, and Al, Si, Ti, and Zr are preferable, and Si is more preferable.

X is one type selected from a hydroxy group, an alkoxy group, an acyloxy group, a phosphoryloxy group, a sulfonyloxy group, an amino group, an oxime group, and O=C($R^a$)($R^b$), the alkoxy group, the acyloxy group, and the oxime group are preferable, and the alkoxy group is more preferable. Furthermore, in a case where X is O=C($R^a$)($R^b$), X is bonded to M by an unshared electron pair of an oxygen atom of a carbonyl group (—CO—). $R^a$ and $R^b$ each independently represent a monovalent organic group.

It is preferable that the partial structure represented by M-X, in particular, is a combination in which M is Si, and X is an alkoxy group. According to such a combination, the near infrared ray absorbent composition has moderate reactivity, and thus, it is possible to make preservation stability of the near infrared ray absorbent composition excellent. Further, a cured film having more excellent heat resistance is easily formed.

The number of carbon atoms of the alkoxy group is preferably 1 to 20, is more preferably 1 to 10, is even more preferably 1 to 5, and is particularly preferably 1 and 2. The alkoxy group may be any one of a linear alkoxy group, a branched alkoxy group, and a cyclic alkoxy group, the linear alkoxy group or the branched alkoxy group is preferable, and the linear alkoxy group is more preferable. The alkoxy group may be a non-substituted alkoxy group, or may be a substituent alkoxy group, and the non-substituted alkoxy group is preferable. Examples of a substituent include a halogen atom (preferably a fluorine atom), a polymerizable group (for example, a vinyl group, a (meth)acryloyl group, a styryl group, an epoxy group, an oxetane group, and the like), an amino group, an isocyanate group, an isocyanurate group, a ureido group, a mercapto group, a sulfide group, a sulfo group, a carboxyl group, a hydroxyl group, and the like.

Examples of the acyloxy group include a substituted alkyl carbonyloxy group or a non-substituted alkyl carbonyloxy group having 2 to 30 carbon atoms, a substituted aryl carbonyloxy group or a non-substituted aryl carbonyloxy group having 6 to 30 carbon atoms, and the like. Examples of the acyloxy group include a formyloxy group, an acetyloxy group, a pivaloyloxy group, a stearoyloxy, a benzoyloxy group, a p-methoxy phenyl carbonyloxy group, and the like. Examples of a substituent include the substituents described above.

The number of carbon atoms of the oxime group is preferably 1 to 20, is more preferably 1 to 10, and is even more preferably 1 to 5. Examples of the oxime group include an ethyl methyl ketoxime group, and the like.

Examples of the amino group include an amino group, a substituted alkyl amino group or a non-substituted alkyl amino group having 1 to 30 carbon atoms, a substituted aryl amino group or a non-substituted aryl amino group having 6 to 30 carbon atoms, a heterocyclic amino group having 0 to 30 carbon atoms, and the like. Examples of the amino group include amino, methyl amino, dimethyl amino, anilino, N-methyl-anilino, diphenyl amino, N-1,3,5-triazin-2-yl amino, and the like. Examples of a substituent include the substituents described above.

Examples of the monovalent organic group represented by $R^a$ and $R^b$ include an alkyl group, an aryl group, a group represented by $-R^{101}-COR^{102}$, and the like.

The number of carbon atoms of the alkyl group is preferably 1 to 20, and is more preferably 1 to 10. The alkyl group may be any one of a linear alkyl group, a branched alkyl group, and a cyclic alkyl group. The alkyl group may be a non-substituted alkyl group, or may have the substituents described above.

The number of carbon atoms of the aryl group is preferably 6 to 20, and is more preferably 6 to 12. The aryl group may be a non-substituted aryl group, or may have the substituents described above.

In the group represented by $-R^{101}-COR^{102}$, $R^{101}$ represents an arylene group, and $R^{102}$ represents an alkyl group or an aryl group.

The number of carbon atoms of the arylene group represented by $R^{101}$ is preferably 1 to 20, is more preferably 1 to 10. The arylene group may be any one of a linear arylene group, a branched arylene group, and a cyclic arylene group. The arylene group may be a non-substituted arylene group, or may have the substituents described above.

Examples of the alkyl group and the aryl group represented by $R^{102}$ include the groups described in $R^a$ and $R^b$, and the preferred ranges thereof are identical to those of the groups described in $R^a$ and $R^b$.

The compound having a partial structure represented by M-X may be any one of a low molecular compound and a polymer, the polymer is preferable from the reason of easily forming a film having more excellent heat resistance.

In the compound having a partial structure represented by M-X, it is preferable that the molecular weight of the low molecular compound is 100 to 1,000. The upper limit is preferably less than or equal to 800, and is more preferably less than or equal to 700. Furthermore, the molecular weight is a theoretical value obtained from a structural formula.

In the compound having a partial structure represented by M-X, it is preferable that the weight-average molecular weight of a polymer type compound is 500 to 300,000. The lower limit is preferably greater than or equal to 1,000, and is more preferably greater than or equal to 2,000. The upper limit is preferably less than or equal to 250,000, and is more preferably less than or equal to 200,000.

In the compound having a partial structure represented by M-X, examples of the low molecular compound include a compound represented by (MX1) described below.

$$M-(X^1)_m \quad (MX1)$$

M represents an atom selected from Si, Ti, Zr, and Al, $X^1$ represents a substituent or a ligand, at least one of m $X^1$'s is one type selected from a hydroxy group, an alkoxy group, an acyloxy group, a phosphoryloxy group, a sulfonyloxy group, an amino group, an oxime group, and O=$C(R^a)(R^b)$, $X^1$'s may form a ring by being bonded to each other, and m represents the number of bonding hands between M and $X^1$. $R^a$ and $R^b$ each independently represent a monovalent organic group.

M is an atom selected from Si, Ti, Zr, and Al, Si, Ti, and Zr are preferable, and Si is more preferable.

$X^1$ represents a substituent or a ligand, at least one of m $X^1$'s is one type selected from a hydroxy group, an alkoxy group, an acyloxy group, a phosphoryloxy group, a sulfonyloxy group, an amino group, an oxime group, and O=C$(R^a)(R^b)$, and it is preferable that at least one of m $X^1$'s is one type selected from an alkoxy group, an acyloxy group, and an oxime group, it is more preferable that at least one of m $X^1$'s is an alkoxy group, and it is even more preferable that all $X^1$'s are alkoxy groups.

In the substituent and the ligand, the hydroxy group, the alkoxy group, the acyloxy group, the phosphoryloxy group, the sulfonyloxy group, the amino group, the oxime group, and O=$C(R^a)(R^b)$ are identical to those described above, and the preferred ranges thereof are identical to those described above.

A hydrocarbon group is preferable as a substituent other than the hydroxy group, the alkoxy group, the acyloxy group, the phosphoryloxy group, the sulfonyloxy group, the amino group, and the oxime group. Examples of the hydrocarbon group include an alkyl group, an alkenyl group, an aryl group, and the like.

The alkyl group may be any one of a linear alkyl group, a branched alkyl group, and a cyclic alkyl group. The number of carbon atoms of the linear alkyl group is preferably 1 to 20, is more preferably 1 to 12, and is even more preferably 1 to 8. The number of carbon atoms of the branched alkyl group is preferably 3 to 20, is more preferably 3 to 12, and is even more preferably 3 to 8. The cyclic alkyl group may be any one of a monocyclic alkyl group and a polycyclic alkyl group. The number of carbon atoms of the cyclic alkyl group is preferably 3 to 20, is more preferably 4 to 10, and is even more preferably 6 to 10.

The number of carbon atoms of the alkenyl group is preferably 2 to 10, is more preferably 2 to 8, and is even more preferably 2 to 4.

The number of carbon atoms of the aryl group is preferably 6 to 18, is more preferably 6 to 14, and is even more preferably 6 to 10.

The hydrocarbon group may have a substituent, and examples of the substituent include an alkyl group, a halogen atom (preferably a fluorine atom), a polymerizable group (for example, a vinyl group, a (meth)acryloyl group, a styryl group, an epoxy group, an oxetane group, and the like), an amino group, an isocyanate group, an isocyanurate group, a ureido group, a mercapto group, a sulfide group, a sulfo group, a carboxyl group, a hydroxyl group, an alkoxy group, and the like.

Examples of a compound in which M is Si include methyl trimethoxy silane, dimethyl dimethoxy silane, phenyl trimethoxy silane, methyl triethoxy silane, dimethyl diethoxy silane, phenyl triethoxy silane, n-propyl trimethoxy silane, n-propyl triethoxy silane, hexyl trimethoxy silane, hexyl triethoxy silane, octyl triethoxy silane, decyl trimethoxy silane, 1,6-bis(trimethoxy silyl) hexane, trifluoropropyl trimethoxy silane, hexamethyl disilazane, vinyl trimethoxy silane, vinyl triethoxy silane, 2-(3, 4-epoxy cyclohexyl) ethyl trimethoxy silane, 3-glycidoxy propyl methyl dimethoxy silane, 3-glycidoxy propyl trimethoxy 3-glycidoxy propyl methyl diethoxy silane, 3-glycidoxy propyl triethoxy silane, p-styryl trimethoxy silane, 3-methacryloxy propyl methyl dimethoxy silane, 3-methacryloxy propyl trimethoxy silane, 3-methacryloxy propyl methyl diethoxy silane, 3-methacryloxy propyl triethoxy silane, 3-acryloxy propyl trimethoxy silane, N-2-(amino ethyl)-3-amino propyl methyl dimethoxy silane, N-2-(amino ethyl)-3-amino propyl trimethoxy silane, 3-amino propyl trimethoxy silane, 3-amino propyl triethoxy silane, 3-triethoxy silyl-N-(1,3-dimethyl-butylidene) propyl amine, N-phenyl-3-amino propyl trimethoxy silane, a hydrochloride of N-(vinyl benzyl)-2-amino ethyl-3-amino propyl trimethoxy silane, tris-(trimethoxy silyl propyl) isocyanurate, 3-ureidopropyl triethoxy silane, 3-mercapto propyl methyl dimethoxy silane, 3-mercapto propyl trimethoxy silane, bis(triethoxy silyl propyl) tetrasulfide, 3-isocyanate propyl triethoxy silane, and the like.

Examples of a commercially available product include KBM-13, KBM-22, KBM-103, KBE-13, KBE-22, KBE-103, KBM-3033, KBE-3033, KBM-3063, KBE-3063, KBE-3083, KBM-3103, KBM-3066, KBM-7103, SZ-31, KPN-3504, KBM-1003, KBE-1003, KBM-303, KBM-402, KBM-403, KBE-402, KBE-403, KBM-1403, KBM-502, KBM-503, KBE-502, KBE-503, KBM-5103, KBM-602, KBM-603, KBM-903, KBE-903, KBE-9103, KBM-573, KBM-575, KBM-9659, KBE-585, KBM-802, KBM-803, KBE-846, KBE-9007, and the like, which are manufactured by Shin-Etsu Chemical Co., Ltd.

Examples of a compound in which M is Ti include tetraisopropyl titanate, tetranormal butyl titanate, a butyl titanate dimer, tetraoctyl titanate, titanium diisopropoxy bis(acetyl acetonate), titanium tetraacetyl acetonate, titanium diisopropoxy bis(ethyl acetoacetate), a titanium phosphate compound, titanium di-2-ethyl hexoxy bis(2-ethyl-3-hydroxy hexoxide), titanium diisopropoxy bis(ethyl acetoacetate), a titanium lactate ammonium salt, titanium lactate, titanium diisopropoxy bis(triethanol aminate), tertiary amyl titanate, tetratertiary butyl titanate, tetrastearyl titanate, titanium-1,3-propane dioxy bis(ethyl acetoacetate), a titanium dodecyl benzene sulfonate compound, titanium isostearate, titanium diethanol aminate, titanium aminoethyl aminoethanolate, and the like. Examples of a commercially available product include ORGATIX series (for example, TA-10, TA-21, TA-23, TA-30, TC-100, TC-401, TC-710, TC-1040, TC-201, TC-750, TC-300, TC-310, TC-315, TC-400, TA-60, TA-80, TA-90, TC-120, TC-220, TC-730, TC-810, TC-800, TC-500, TC-510, and the like) which are manufactured by Matsumoto Fine Chemical Co., Ltd., and PLENACT series (for example, TTS, 46B, 55, 41B, 38S, 138S, 238S, 338X, 44, 9SA, ET, and the like) which are manufactured by Ajinomoto Fine-Techno Co., Inc.

Examples of a compound in which M is Zr include zirconium tetranormal propoxide, zirconium tetranormal butoxide, zirconium tetraacetyl acetonate, zirconium tributoxy monoacetyl acetonate, zirconium dibutoxy bis(ethyl acetoacetate), and the like. Examples of a commercially available product include ORGATIX series (for example, ZA-45, ZA-65, ZC-150, ZC-540, ZC-700, ZC-580, ZC-200, ZC-320, ZC-126, ZC-300, and the like) which are manufactured by Matsumoto Fine Chemical Co., Ltd.

Examples of a compound in which M is Al include alkyl acetoacetate aluminum diisopropylate, and the like. Examples of a commercially available product include PLENACT AL-M and the like which are manufactured by Ajinomoto Fine-Techno Co., Inc.

In the compound having a partial structure represented by M-X, examples of the polymer type compound include an acrylic resin, an acrylamide resin, a styrene resin, polysiloxane, and the like. Among them, the acrylic resin, the acrylamide resin, or the styrene resin is preferable from the reason of easily improving coating properties and easily adjusting a coating liquid viscosity.

Specific examples of the polymer type compound include a polymer having one type selected from a repeating unit represented by (MX2-1) described below, a repeating unit represented by (MX2-2) described below, and a repeating unit represented by (MX2-3) described below, and the like.

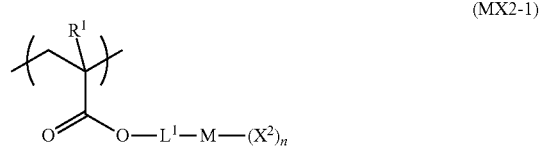

(MX2-1)

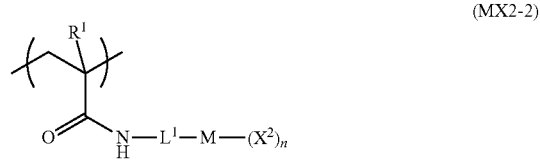

(MX2-2)

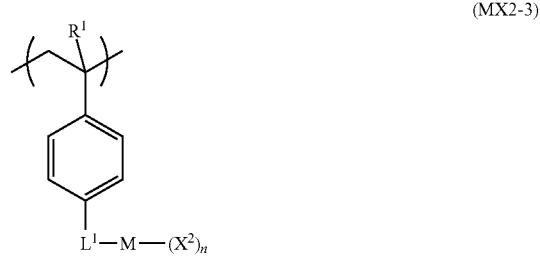

(MX2-3)

M represents an atom selected from Si, Ti, Zr, and Al, $X^2$ represents a substituent or a ligand, at least one of n $X^2$'s is one type selected from a hydroxy group, an alkoxy group, an acyloxy group, a phosphoryloxy group, a sulfonyloxy group, an amino group, an oxime group, and $O=C(R^a)(R^b)$, $X^2$'s may form a ring by being bonded to each other, $R^1$ represents a hydrogen atom or an alkyl group, $L^1$ represents a single bond or a divalent linking group, and n represents the number of bonding hands between M and $X^2$.

M and $X^2$ are identical to M and $X^1$ of (MX1), and the preferred ranges thereof are identical to those of M and $X^1$ of (MX1).

$R^1$ represents a hydrogen atom or an alkyl group. The number of carbon atoms of the alkyl group is preferably 1 to 5, is more preferably 1 to 3, and is particularly preferably 1. The alkyl group is preferably any one of a linear alkyl group and a branched alkyl group, and the linear alkyl group is more preferable. In the alkyl group, a part or all of hydrogen atoms may be substituted with a halogen atom (preferably a fluorine atom).

$L^1$ represents a single bond or a divalent linking group. Examples of the divalent linking group include an alkylene group, an arylene group, —O—, —S—, —CO—, —COO—, —OCO—, —SO$_2$—, —NR$^{10}$— ($R^{10}$ represents a hydrogen atom or an alkyl group, and the hydrogen atom is preferable), or a group formed of a combination thereof, and the alkylene group, and a group formed of a combination between at least one of the arylene group or the alkylene group and —O— are preferable.

The number of carbon atoms of the alkylene group is preferably 1 to 30, is more preferably 1 to 15, and is even more preferably 1 to 10. The alkylene group may have a substituent, and a non-substituted alkylene group is preferable. The alkylene group may be any one of a linear alkylene group, a branched alkylene group, and a cyclic alkylene group. In addition, the cyclic alkylene group may be any one of a monocyclic alkylene group and a polycyclic alkylene group.

The number of carbon atoms of the arylene group is preferably 6 to 18, is more preferably 6 to 14, and is even more preferably 6 to 10, and a phenylene group is particularly preferable.

The polymer type compound described above may contain other repeating units in addition to the repeating units represented by Formulas (MX2-1), (MX2-2), and (MX2-3).

A component configuring the other repeating unit can be referred to the description of a copolymerization component disclosed in paragraphs 0068 to 0075 of JP2010-106268A ([0112] to [0118] of the specification of corresponding US2011/0124824A), and the contents thereof are incorporated herein. Preferred examples of the other repeating unit include repeating units represented by Formulas (MX3-1) to (MX3-6) described below.

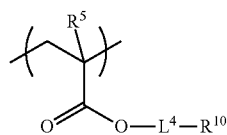

(MX3-1)

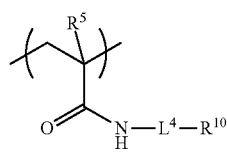

(MX3-2)

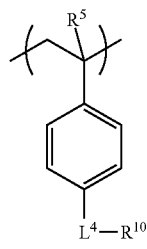

(MX3-3)

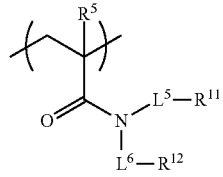

(MX3-4)

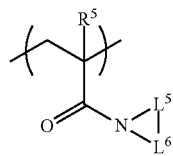

(MX3-5)

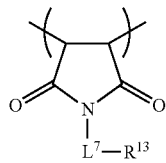

(MX3-6)

In Formulas (MX3-1) to (MX3-6), $R^5$ represents a hydrogen atom or an alkyl group, $L^4$ to $L^7$ each independently represent a single bond or a divalent linking group, and $R^{10}$ to $R^{13}$ each independently represent an alkyl group or an aryl group.

$R^5$ is identical to $R^1$ of Formulas (MX2-1) to (MX2-3), and the preferred range thereof is identical to that of $R^1$ of Formulas (MX2-1) to (MX2-3).

$L^4$ to $L^7$ are identical to $L^1$ of Formulas (MX2-1) to (MX2-3), and the preferred range thereof is identical to that of $L^1$ of Formulas (MX2-1) to (MX2-3).

The alkyl group represented by $R^{10}$ may be any one of a linear alkyl group, a branched alkyl group, and a cyclic alkyl group, and the cyclic alkyl group is preferable. The number of carbon atoms of the alkyl group is preferably 1 to 30, is more preferably 1 to 20, and is even more preferably 1 to 10. The alkyl group may have a substituent, and examples of the substituent include the substituents described above.

The aryl group represented by $R^{10}$ may be a monocyclic aryl group, or may be a polycyclic aryl group, and the monocyclic aryl group is preferable. The number of carbon atoms of the aryl group is preferably 6 to 18, is more preferably 6 to 12, and is even more preferably 6.

It is preferable that $R^{10}$ is the cyclic alkyl group or the cyclic aryl group.

The alkyl group represented by $R^{11}$ and $R^{12}$ may be any one of a linear alkyl group, a branched alkyl group, and a cyclic alkyl group, and the linear alkyl group or the branched alkyl group is preferable. The alkyl group may be substituted, and examples of a substituent include the substituents described above. The number of carbon atoms of the alkyl group is preferably 1 to 12, is more preferably 1 to 6, and is even more preferably 1 to 4.

The aryl group represented by $R^{11}$ and $R^{12}$ may be a monocyclic aryl group, or may be a polycyclic aryl group, and the monocyclic aryl group is preferable. The number of carbon atoms of the aryl group is preferably 6 to 18, is more preferably 6 to 12, and is even more preferably 6.

It is preferable that $R^{11}$ and $R^{12}$ are the linear alkyl group or the branched alkyl group.

The alkyl group represented by $R^{13}$ may be any one of a linear alkyl group, a branched alkyl group, and a cyclic alkyl group, and the linear alkyl group or the branched alkyl group is preferable. The alkyl group may be substituted, and examples of a substituent include the substituents described above. The number of carbon atoms of the alkyl group is preferably 1 to 12, is more preferably 1 to 6, and is even more preferably 1 to 4.

The aryl group represented by $R^{13}$ may be a monocyclic aryl group, or may be a polycyclic aryl group, and the monocyclic aryl group is preferable. The number of carbon atoms of the aryl group is preferably 6 to 18, is more preferably 6 to 12, and is even more preferably 6.

It is preferable that $R^{13}$ is a linear alkyl group or a branched alkyl group, or a linear aryl group or a branched aryl group.

In a case where the polymer type compound described above includes the other repeating unit (preferably the repeating units represented by Formulas (MX3-1) to (MX3-6)), a molar ratio of the total of the repeating units represented by Formulas (MX2-1) to (MX2-3) to the total of the other repeating unit is preferably 95:5 to 20:80, and is more preferably 90:10 to 40:60. By increasing the content rate of the repeating units represented by Formulas (MX2-1) to (MX2-3) in the range described above, moisture resistance and solvent resistance of the cured film to be obtained tend to be further improved. In addition, by decreasing the content rate of the repeating units represented by Formulas (MX2-1) to (MX2-3) in the range described above, heat resistance of the cured film to be obtained tends to be further improved.

Examples of the polymer type compound in which M is Si include compounds shown below. Furthermore, a numerical value described in a repeating unit is a molar ratio. In addition, Mw is a weight-average molecular weight. Further, Me represents a methyl group and Et represents an ethyl group.

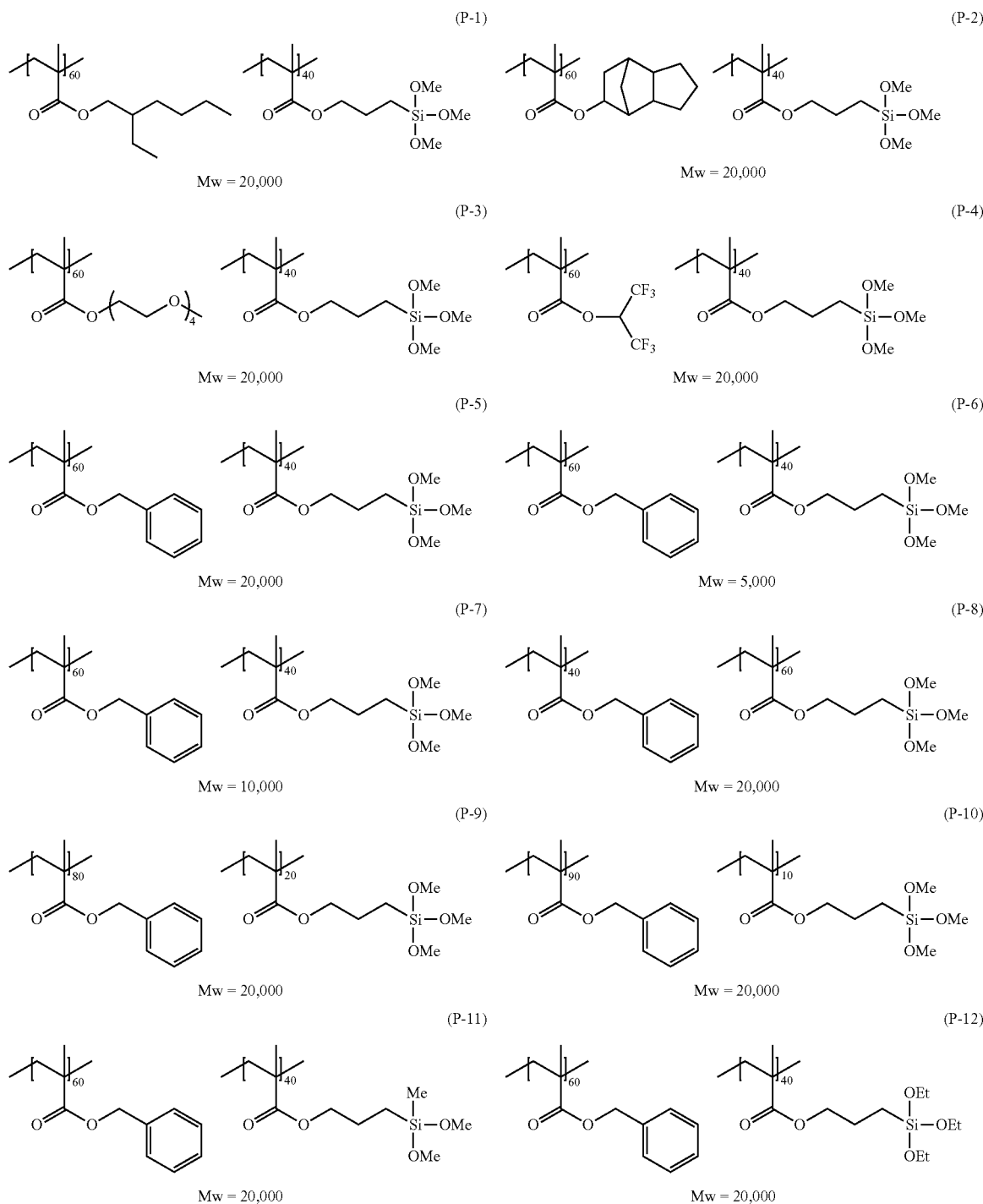

-continued
(P-13)
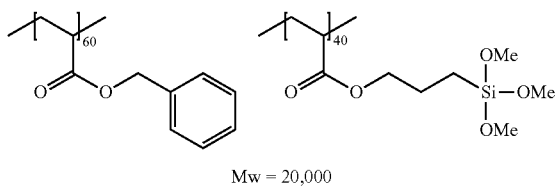
Mw = 20,000
(P-14)
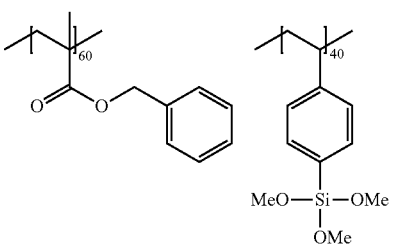
Mw = 20,000
(P-15)
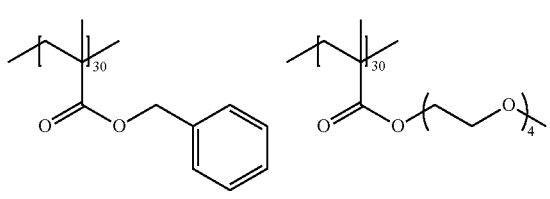
Mw = 20,000
(P-16)
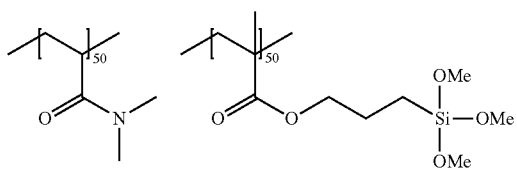
Mw = 15,000
(P-17)
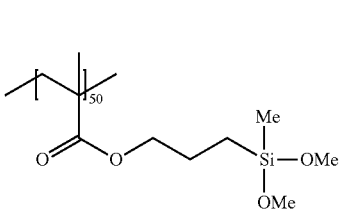
Mw = 15,000
(P-18)
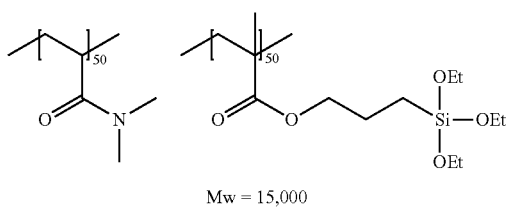
Mw = 15,000
(P-19)
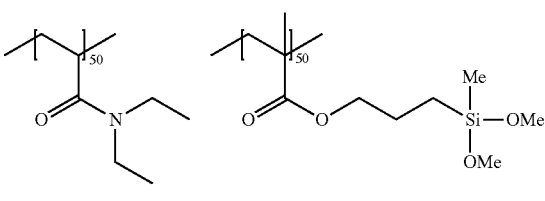
Mw = 15,000
(P-20)
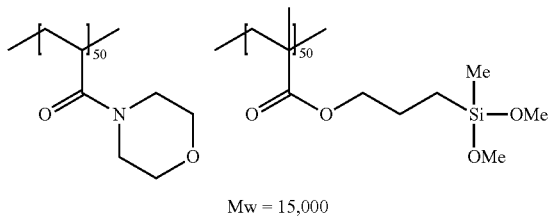
Mw = 15,000
(P-21)
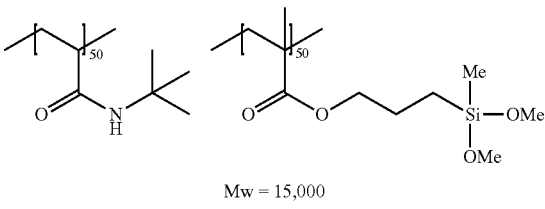
Mw = 15,000
(P-22)
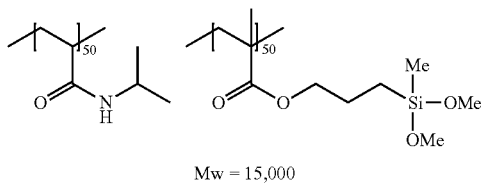
Mw = 15,000
(P-23)
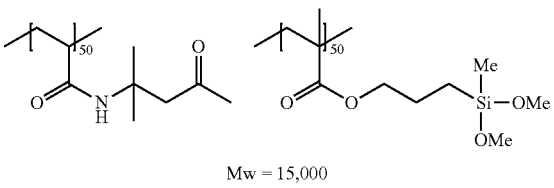
Mw = 15,000

-continued

-continued

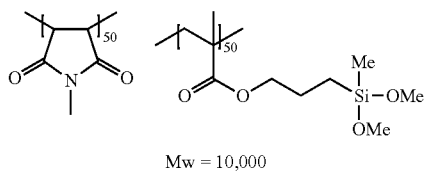
(P-37)
Mw = 10,000

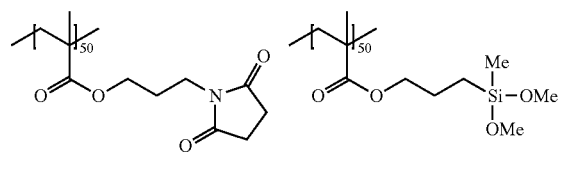
(P-38)
Mw = 15,000

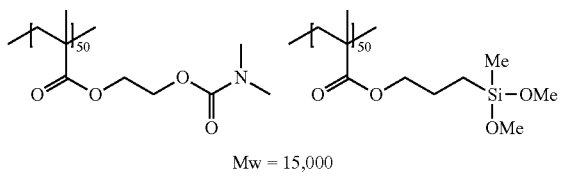
(P-39)
Mw = 15,000

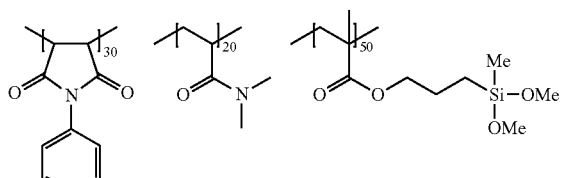
(P-40)
Mw = 10,000

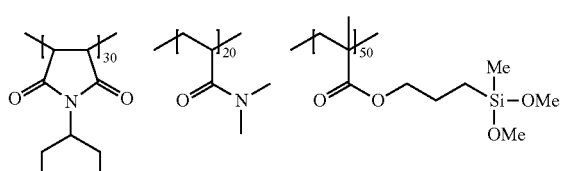
(P-41)
Mw = 10,000

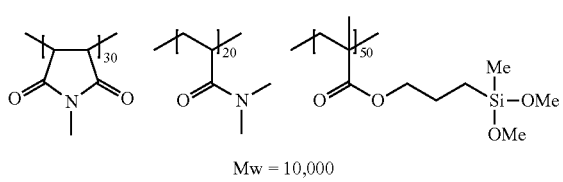
(P-42)
Mw = 10,000

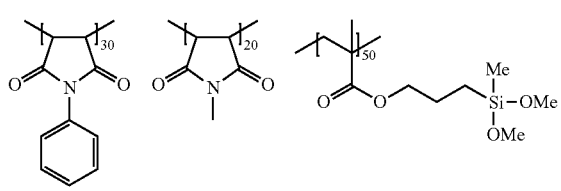
(P-43)
Mw = 10,000

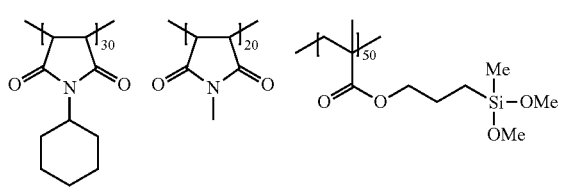
(P-44)
Mw = 10,000

In the present invention, polysiloxane can also be used as the polymer type compound having a partial structure represented by M-X. Examples of the polysiloxane include KC-89S, KR-500, X-40-9225, X-40-9246, and X-40-9250 (all are methyl-based silicone alkoxy oligomers having a methoxy group), KR-9218, KR-213, KR-510, X-40-9227, and X-40-9247 (all are methyl phenyl-based silicone alkoxy oligomers having a methoxy group), X-41-1053, X-41-1059, A, X-41-1056, X-41-1805, X-41-1818, X-41-1810, KR-513, X-40-2672B, X-40-9272B, X-40-2651, X-40-2308, and X-40-9238 (a silicone alkoxy oligomer), and the like, which are manufactured by Shin-Etsu Chemical Co., Ltd.

In a case of including the compound having a partial structure represented by M-X as the curable compound, the content of the compound having a partial structure represented by M-X is preferably greater than or equal to 15 mass %, is more preferably greater than or equal to 20 mass %, and is even more preferably greater than or equal to 25 mass %, with respect to the total solid content of the near infrared ray absorbent composition. The upper limit is not particularly limited, but is preferably less than or equal to 99 mass %, is more preferably less than or equal to 90 mass %, is even more preferably less than or equal to 80 mass %, and still more preferably less than or equal to 70 mass %. In a case where the content of the compound having a partial structure represented by M-X is in the range described above, a cured film having excellent heat resistance is easily formed.

In addition, a mass ratio of the compound having a partial structure represented by M-X to the copper complex, that is, Compound Having Partial Structure Represented by M-X: Copper Complex is preferably 15:85 to 90:10, is more preferably 20:80 to 80:20, and is even more preferably 25:75 to 70:30. In a case where the ratio of the both compounds is in the range described above, a cured film having excellent heat resistance while maintaining high near infrared ray shielding properties is easily formed.

In addition, the compound having a partial structure represented by M-X can have an aspect which is substantially configured of one type selected from the low molecular compound and the polymer type compound described above. Furthermore, "being substantially configured of one type selected from the low molecular compound and the polymer type compound", for example, indicates that the content of the compound other than a target type compound in the low molecular compound and the polymer type compound is preferably less than or equal to 1 mass %, and is more preferably less than or equal to 0.5 mass %, with respect to the total mass of the compound having a partial structure represented by M-X, and it is even more preferable that the compound other than the target type compound is not contained. For example, in a case where the target type compound is the polymer type compound, the low molecular compound corresponds to the compound other than the target type compound.

In addition, one or more types selected from the low molecular compound and one or more types selected from the polymer type compound can be used in combination. A mass ratio of the total of the low molecular compounds to the total of the polymer type compounds is preferably 1:9 to 5:5, is more preferably 1:9 to 4:6, and is particularly preferably 1:9 to 3:7.

<<<Other Curable Compounds>>>

In the present invention, a polymerizable compound having a caprolactone-modified structure can be used as the curable compound.

The polymerizable compound having a caprolactone-modified structure can be referred to the description of paragraphs 0042 to 0045 of JP2013-253224A, and the contents thereof are incorporated herein.

Examples of the polymerizable compound having a caprolactone-modified structure include DPCA-20, DPCA-30, DPCA-60, DPCA-120, and the like, which are commercially as KAYARAD DPCA series from Nippon Kayaku Co., Ltd., SR-494 manufactured by Arkema Inc., which is tetrafunctional acrylate having four ethylene oxy chains, TPA-330 manufactured by Arkema Inc., which is trifunctional acrylate having three isobutylene oxy chains, and the like.

<<Binder Polymer>>

The near infrared ray absorbent composition of the present invention can contain a binder polymer in order to improve film properties or the like. An alkali soluble resin is preferably used as the binder polymer. By containing the alkali soluble resin, an effect is obtained in which heat resistance or the like is improved, or coating suitability is finely adjusted. The alkali soluble resin can be referred to the description of paragraphs 0558 to 0571 of JP2012-208494A ([0685] to [0700] of the specification of corresponding US2012/0235099A), and the contents thereof are incorporated herein.

In a case where the near infrared ray absorbent composition of the present invention contains the binder polymer, the content of the binder polymer is preferably 1 to 80 mass % with respect to the total solid content of the near infrared ray absorbent composition. The lower limit is preferably greater than or equal to 5 mass %, and is more preferably greater than or equal to 7 mass %. The upper limit is preferably less than or equal to 50 mass %, and is more preferably less than or equal to 30 mass %.

<<Surfactant>>

The near infrared ray absorbent composition of the present invention may contain a surfactant. Only one type of the surfactant may be used, or two or more types thereof may be used in combination. In a case where near infrared ray absorbent composition of the present invention contains the surfactant, the content of the surfactant is preferably 0.0001 to 2 mass % with respect to the total solid content of the near infrared ray absorbent composition. The lower limit is preferably greater than or equal to 0.005 mass %, and is more preferably greater than or equal to 0.01 mass %. The upper limit is preferably less than or equal to 1.0 mass %, and is more preferably less than or equal to 0.1 mass %.

Various surfactants such as a fluorine-based surfactant, a nonionic surfactant, a cationic surfactant, an anionic surfactant, and a silicone-based surfactant can be used as the surfactant. It is preferable that the near infrared ray absorbent composition of the present invention contains at least one of the fluorine-based surfactant or the silicone-based surfactant. An interfacial tension between a surface to be coated and a coating liquid decreases, and thus, wettability with respect to the surface to be coated is improved. For this reason, liquid properties (in particular, fluidity) of the near infrared ray absorbent composition are improved, and thus, homogeneity of a coating thickness or liquid saving properties are further improved. As a result thereof, even in a case where a thin film of approximately several μm is formed by a small amount of liquid, a film which has a homogeneous thickness and small thickness unevenness can be formed.

A fluorine content rate of the fluorine-based surfactant is preferably 3 to 40 mass %. The lower limit is preferably greater than or equal to 5 mass %, and more preferably greater than or equal to 7 mass %. The upper limit is preferably less than or equal to 30 mass %, and is more preferably less than or equal to 25 mass %. In a case where the fluorine content rate is in the range described above, it is effective from the viewpoint of homogeneity of a thickness of a coated film or liquid saving properties, and solubility in the near infrared ray absorbent composition is also excellent.

Specifically, examples of the fluorine-based surfactant include surfactants described in paragraphs 0060 to 0064 of JP2014-41318A (paragraphs 0060 to 0064 of the pamphlet of corresponding WO2014/17669A), and the like, and the contents thereof are incorporated herein.

Examples of the fluorine-based surfactant include MEGAFACE F171, MEGAFACE F172, MEGAFACE F173, MEGAFACE F176, MEGAFACE F177, MEGAFACE F141, MEGAFACE F142, MEGAFACE F143, MEGAFACE F144, MEGAFACE R30, MEGAFACE F437, MEGAFACE F475, MEGAFACE F479, MEGAFACE F482, MEGAFACE F554, MEGAFACE F780, and RS-72-K (which are manufactured by DIC Corporation), FLUORAD FC430, FLUORAD FC431, and FLUORAD FC171 (which are manufactured by Sumitomo 3M Limited), SURFLON S-382, SURFLON SC-101, SURFLON SC-103, SURFLON SC-104, SURFLON SC-105, SURFLON SC1068, SURFLON SC-381, SURFLON SC-383, SURFLON S393, and SURFLON KH-40 (which are manufactured by AGC SEIMI CHEMICAL CO., LTD.), and PF636, PF656, PF6320, PF6520, and PF7002 (which are manufactured by OMNOVA Solutions Inc.). As the fluorine-based surfactant, compounds described in paragraphs 0015 to 0158 of JP2015-117327A can also be used. A block polymer can also be used as the fluorine-based surfactant, and specifically, compounds described in JP2011-89090A are used.

As the fluorine-based surfactant, a fluorine-containing polymer compound including a repeating unit derived from a (meth)acrylate compound including fluorine atoms and a repeating unit derived from a (meth)acrylate compound including two or more (preferably, five or more) alkyleneoxy groups (preferably, an ethyleneoxy group or a propyleneoxy group) can be preferably used, and the following compound is also used as the fluorine-based surfactant used in the present invention.

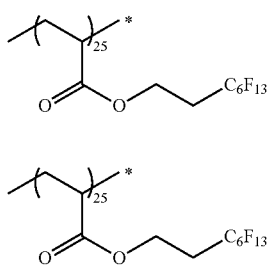
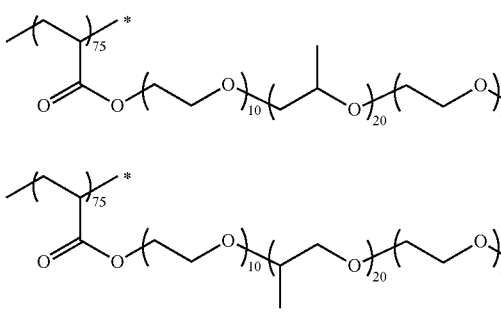

Mixture

A weight-average molecular weight of the compound is preferably 3,000 to 50,000 and, is for example, 14,000.

In addition, a fluorine-containing polymer including an ethylenically unsaturated group in a side chain can also be used as the fluorine-based surfactant. Specific examples thereof include compounds disclosed in paragraphs 0050 to 0090 and 0289 to 0295 of JP2010-164965A, for example, MEGAFACE RS-101, RS-102, and RS-718K manufactured by DIC Corporation.

<<Polymerization Initiator>>

The near infrared ray absorbent composition of the present invention may contain a polymerization initiator. The polymerization initiator is not particularly limited insofar as the polymerization initiator has an ability of initiating polymerization of a polymerizable compound by either light or heat, or both of light and heat, but a photopolymerization initiator is preferable.

A compound having an aromatic group is preferable as the polymerization initiator. Examples of the compound include an acyl phosphine compound, an acetophenone compound, an α-amino ketone compound, a benzophenone compound, a benzoin ether compound, a ketal derivative compound, a thioxanthone compound, an oxime compound, a hexaaryl biimidazole compound, a trihalomethyl compound, an azo compound, an organic peroxide, a diazonium compound, an iodonium compound, a sulfonium compound, an azinium compound, an onium salt compound such as a metallocene compound, an organic boron salt compound, a disulfone compound, a thiol compound, and the like.

The polymerization initiator can be referred to the description of paragraphs 0217 to 0228 of JP2013-253224A, and the contents thereof are incorporated herein.

The polymerization initiator is preferably an oxime compound, an acetophenone compound, or an acyl phosphine compound. IRGACURE-907, IRGACURE-369, and IRGA-CURE-379 (Product Names, which are manufactured by BASF SE), and the like can be used as a commercially available product of the acetophenone compound. IRGA-CURE-819 and DAROCUR-TPO (Product Names, which are manufactured by BASF SE), and the like can be used as a commercially available product of the acyl phosphine compound.

In a case where the near infrared ray absorbent composition of the present invention contains the polymerization initiator, the content of the polymerization initiator is preferably 0.01 to 30 mass % with respect to the total solid content of the near infrared ray absorbent composition. The lower limit is preferably greater than or equal to 0.1 mass %. The upper limit is preferably less than or equal to 20 mass %, and is more preferably less than or equal to 15 mass %.

Only one type of the polymerization initiator may be used, or two or more types thereof may be used, and in a case where two or more types of the polymerization initiators are used, it is preferable that the total amount is in the range described above.

(Thermal Stability Imparting Agent)

The near infrared ray absorbent composition of the present invention can also include a thermal stability imparting agent. An oxime compound is used as the thermal stability imparting agent. Examples of the oxime compound include IRGACURE-OXE01 (manufactured by BASF SE), IRGA-CURE-OXE02 (manufactured by BASF SE), TR-PBG-304 (manufactured by Changzhou Tronly New Electronic Materials CO., LTD.), ADEKA ARKLS NCI-831 (manufactured by ADEKA CORPORATION), ADEKA ARKLS NCI-930 (manufactured by ADEKA CORPORATION), and the like which are commercially available products.

In the present invention, an oxime compound including fluorine atoms can also be used as the oxime compound. Specific examples of the oxime compound including fluorine atoms include compounds disclosed in JP2010-262028A, compounds 24 and 36 to 40 disclosed in JP2014-500852A, and compounds (C-3) disclosed in JP2013-164471A. The contents thereof are incorporated herein.

In the present invention, an oxime compound including a nitro group can also be used as the oxime compound. Specific examples of the oxime compound including a nitro group include compounds disclosed in paragraphs 0031 to 0047 of JP2013-114249A and paragraphs 0008 to 0012 and 0070 to 0079 of JP2014-137466A, or ADEKA ARKLS NCI-831 (manufactured by ADEKA CORPORATION).

The content of the thermal stability imparting agent is preferably 0.01 to 30 mass % with respect to the total solid content of the near infrared ray absorbent composition. The lower limit is preferably greater than or equal to 0.1 mass %. The upper limit is preferably less than or equal to 20 mass % and more preferably less than or equal to 10 mass %.

(Catalyst)

The near infrared ray absorbent composition of the present invention can include a catalyst. For example, by including a catalyst, in a case of using the compound having a partial structure represented by M-X as the curable compound, a crosslinking reaction of the curable compound is promoted, and a cured film having excellent solvent resistance or heat resistance is easily obtained. Examples of the catalyst include an organometallic catalyst, an acid catalyst, and an amine catalyst, and the organometallic catalyst is preferable. Tris(2,4-pentanedionato) aluminum (III) and the like are used as the organometallic catalyst. The content of the catalyst is preferably 0.01 to 5 mass % with respect to the total solid content of the near infrared ray absorbent composition. The lower limit is preferably greater than or equal to 0.05 mass %. The upper limit is preferably less than or equal to 3 mass % and more preferably less than or equal to 1 mass %.

<<Other Components>>

Examples of other components which can be used together in the near infrared ray absorbent composition of the present invention include a dispersant, a sensitizer, a crosslinking agent, a curing accelerator, a filler, a thermal curing accelerator, a thermal polymerization inhibitor, a plasticizer, and the like, and an adhesion accelerator with respect to a surface of a substrate and other auxiliary agents (for example, conductive particles, a filler, an antifoaming agent, a flame retardant, a leveling agent, a peeling accelerator, an antioxidant, a flavoring agent, a surface tension adjuster, a chain transfer agent, and the like) may be used together.

By suitably containing such components, it is possible to adjust properties such as stability and film physical properties of the near infrared ray absorbent composition which is a target.

The components, for example, can be referred to the description of paragraph 0183 on and after of JP2012-003225A ([0237] on and after of the specification of corresponding US2013/0034812A), the description of paragraphs 0101 to 0104 and 0107 to 0109 of JP2008-250074A, and the like, and the contents thereof are incorporated herein.

<Preparation and Usage of Near Infrared Ray Absorbent Composition>

The near infrared ray absorbent composition of the present invention can be prepared by mixing the components described above.

When preparing the composition, the components configuring the composition may be collectively blended or the components may be dissolved and dispersed in an organic solvent and then sequentially blended. The introducing order or the operation conditions when performing the blending are not particularly limited.

In the present invention, it is preferable to perform filtering with a filter in order to remove foreign materials or decrease defects. Any filters can be used without particular limitation, as long as it is a filter used for filtering in the related art. For example, filters using a fluorine resin such as polytetrafluoroethylene (PTFE), a polyamide resin such as nylon-6, and nylon-6,6, a polyolefin resin (including high density and ultrahigh molecular weight) such as polyethylene and polypropylene (PP) are used. Among these materials, polypropylene (including a high-density polypropylene) and nylon are preferable.

A hole diameter of the filter is preferably 0.1 to 7.0 μm, more preferably 0.2 to 2.5 μm, even more preferably 0.2 to 1.5 μm, and still more preferably 0.3 to 0.7 μm. When the hole diameter is in the range described above, it is possible to reliably remove fine foreign materials such as impurities or aggregates contained in the composition while preventing filter clogging.

When using the filter, different filters may be combined with each other. At this time, the filtering performed by a first filter may be performed once or may be performed two or more times. In a case of performing the filtering two or more times by combining different filters with each other, a hole diameter in the second and subsequent filtering is preferably the same as or larger than a hole diameter in the first filtering. In addition, a first filters having different hole diameters in the range described above may be combined. As the hole diameter here, a nominal value of a filter manufacturer can be referred. As a commercially available filter, for example, a filter can be selected from various filters provided by Pall Corporation, Toyo Roshi Kaisha, Ltd., Nihon Entegris K. K. (Mykrolis Corporation), or Kitz Micro Filter Corporation.

As the second filter, a filter formed of the same material as that of the first filter described above can be used. A hole diameter of the second filter is preferably 0.2 to 10.0 μm, more preferably 0.2 to 7.0 μm, and even more preferably 0.3 to 6.0 μm. When the hole diameter is in the range described above, it is possible to remove foreign materials while causing component particles contained in the composition to remain.

Regarding the near infrared ray absorbent composition of the present invention, when a film having a film thickness after being dried of 100 μm is prepared by using the near infrared ray absorbent composition of the present invention, light transmittance in a thickness direction of the film at a wavelength of 550 nm is preferably greater than or equal to 45%, more preferably greater than or equal to 80%, even more preferably greater than or equal to 85%, still more preferably greater than or equal to 90%, particularly preferably greater than or equal to 92%, and most preferably greater than or equal to 95%. The light transmittance in a thickness direction of the film at a wavelength of 800 nm is preferably less than or equal to 25%, more preferably less than or equal to 20%, even more preferably less than or equal to 15%, still more preferably less than or equal to 10%, and particularly preferably less than or equal to 5%.

In a case where the near infrared ray cut filter is formed by coating, it is preferable that the viscosity of the near infrared ray absorbent composition of the present invention is 1 to 3,000 mPa·s. The lower limit is preferably greater than or equal to 10 mPa·s, and is more preferably greater than or equal to 100 mPa·s. The upper limit is preferably less than or equal to 2,000 mPa·s, and is more preferably less than or equal to 1,500 mPa·s.

The total solid content of the near infrared ray absorbent composition of the present invention is changed according to a coating method, and for example, is preferably 1 to 50 mass %. The lower limit is more preferably greater than or equal to 10 mass %. The upper limit is more preferably less than or equal to 30 mass %.

The usage of the near infrared ray absorbent composition of the present invention is not particularly limited, and can be preferably used for forming a near infrared ray cut filter or the like. For example, the near infrared ray absorbent composition can be preferably used in a near infrared ray cut filter of a solid image pickup element on a light receiving side (for example, a near infrared ray cut filter with respect to a wafer level lens, and the like), a near infrared ray cut filter of the solid image pickup element on a back surface side (a side opposite to the light receiving side), and the like. In particular, the near infrared ray absorbent composition can be preferably used as the near infrared ray cut filter of the solid image pickup element on the light receiving side.

<Near Infrared Ray Cut Filter>

Next, a near infrared ray cut filter of the present invention will be described.

The near infrared ray absorbent composition of the present invention described above can be used in the near infrared ray cut filter of the present invention.

In the near infrared ray cut filter of the present invention, a light transmittance preferably satisfies at least one of the following conditions (1) to (9), more preferably satisfies all of the following conditions (1) to (8), and even more preferably satisfies all of the following conditions (1) to (9).

(1) A light transmittance at a wavelength of 400 nm is preferably greater than or equal to 80%, more preferably greater than or equal to 85%, even more preferably greater than or equal to 90%, still more preferably greater than or equal to 92%, and particularly preferably greater than or equal to 95%.

(2) A light transmittance at a wavelength of 450 nm is preferably greater than or equal to 80%, more preferably greater than or equal to 85%, even more preferably greater than or equal to 90%, still more preferably greater than or equal to 92%, and particularly preferably greater than or equal to 95%.

(3) A light transmittance at a wavelength of 500 nm is preferably greater than or equal to 80%, more preferably greater than or equal to 85%, even more preferably greater than or equal to 90%, still more preferably greater than or equal to 92%, and particularly preferably greater than or equal to 95%.

(4) A light transmittance at a wavelength of 550 nm is preferably greater than or equal to 80%, more preferably greater than or equal to 85%, even more preferably greater than or equal to 90%, still more preferably greater than or equal to 92%, and particularly preferably greater than or equal to 95%.

(5) A light transmittance at a wavelength of 700 nm is preferably less than or equal to 25%, more preferably less than or equal to 20%, even more preferably less than or equal to 15%, still more preferably less than or equal to 10%, and particularly preferably less than or equal to 5%.

(6) A light transmittance at a wavelength of 750 nm is preferably less than or equal to 25%, more preferably less than or equal to 20%, even more preferably less than or equal to 15%, still more preferably less than or equal to 10%, and particularly preferably less than or equal to 5%.

(7) A light transmittance at a wavelength of 800 nm is preferably less than or equal to 25%, more preferably less than or equal to 20%, even more preferably less than or equal to 15%, still more preferably less than or equal to 10%, and particularly preferably less than or equal to 5%.

(8) A light transmittance at a wavelength of 850 nm is preferably less than or equal to 25%, more preferably less than or equal to 20%, even more preferably less than or equal to 15%, still more preferably less than or equal to 10%, and particularly preferably less than or equal to 5%.

(9) A light transmittance at a wavelength of 900 nm is preferably less than or equal to 25%, more preferably less than or equal to 20%, even more preferably less than or equal to 15%, still more preferably less than or equal to 10%, and particularly preferably less than or equal to 5%.

In the near infrared ray cut filter, a light transmittance in the thickness direction of the film in the entire wavelength range of 400 to 550 nm is preferably greater than or equal to 85%, is more preferably greater than or equal to 90%, and is even more preferably greater than or equal to 95%. It is preferable that a light transmittance in a visible range becomes higher, and it is preferable that the light transmittance in a wavelength range of 400 to 550 nm is high. In addition, a light transmittance at at least one point in a wavelength range of 700 to 800 nm is preferably less than or equal to 25% and more preferably less than or equal to 20%. Among them, the light transmittance in the entire wavelength range of 700 to 800 nm is preferably less than or equal to 25% and more preferably less than or equal to 20%.

A film thickness of the near infrared ray cut filter is preferably less than or equal to 300 µm, is even more preferably less than or equal to 200 µm, and is particularly preferably less than or equal to 100 µm. The lower limit of the film thickness, for example, is preferably greater than or equal to 0.1 µm, is more preferably greater than or equal to 0.2 µm, and is more preferably greater than or equal to 0.5 µm.

According to the near infrared ray absorbent composition of the present invention, the near infrared ray absorbent composition has high near infrared ray shielding properties, and thus it is possible to thin the film thickness of the near infrared ray cut filter.

The near infrared ray cut filter of the present invention is used in a lens having a function of absorbing and cutting a near infrared ray (optical lenses such as lens for a camera of a digital camera, a mobile phone, a car-mounted camera, or the like, an f-θ lens, a pickup lens), an optical filter for a semiconductor light receiving element, a near infrared ray absorption film or a near infrared ray absorption plate shielding a heat ray for saving energy, an agricultural coating agent for selectively using solar light, a recording medium using absorption heat of a near infrared ray, a near infrared ray filter for an electronic device or a photograph, protective glasses, sunglasses, a heat ray shielding film, optical character reading and recording, confidential document copy prevention, an electrophotographic photoreceptor, laser welding, and the like. In addition, the near infrared ray cut filter is also useful as a noise cut filter for a CCD camera and a filter for a CMOS image sensor.

<Manufacturing Method of Near Infrared Ray Cut Filter>

The near infrared ray cut filter of the present invention can be manufactured through a step of applying the near infrared ray absorbent composition of the present invention. Specifically, the near infrared ray cut filter can be manufactured through a step of applying the near infrared ray absorbent composition of the present invention onto a support, and a step of drying a film. A film thickness, a laminated structure, and the like can be suitably selected according to the purpose. In addition, a step of forming a pattern may be further performed.

A step of forming a film, for example, can be performed by applying the near infrared ray absorbent composition of the present invention onto the support using a dropwise addition method (drop casting), a spin coater, a slit spin coater, a slit coater, screen printing, applicator coating, and the like. In a case of the dropwise addition method (the drop casting), it is preferable that a dropwise addition region of the near infrared ray absorbent composition, in which a photoresist is used as a partition wall, is formed on the support such that a homogeneous film having a predetermined film thickness is obtained. A desired film thickness can be obtained by adjusting a dropwise addition amount, the concentration of solid contents of the near infrared ray absorbent composition, and the area of the dropwise addition region. The thickness of the film after being dried is not particularly limited, and can be suitably selected according to the purpose.

The support may be a transparent substrate formed of glass or the like. In addition, the support may be a solid image pickup element. In addition, the support may be another substrate disposed on the solid image pickup element on a light receiving side. In addition, the support may be a layer such as a planarizing layer, which is disposed on the solid image pickup element on the light receiving side.

In the step of drying the film, drying conditions are different according to each component, the type of solvent, a use ratio, and the like. For example, it is preferable that the drying is performed at a temperature of 60° C. to 150° C. for 30 seconds to 15 minutes.

The step of forming the pattern is performed by a method including a step of forming a film-like composition layer by applying the near infrared ray absorbent composition of the present invention onto a support, a step of exposing the composition layer, and a step of forming a pattern by developing and removing an unexposed portion, and the like. In the step of forming the pattern, the pattern may be formed by a photolithography method, or the pattern may be formed by a dry etching method.

In the manufacturing method of a near infrared ray cut filter, other steps may be included. The other step is not particularly limited, and can be suitably selected according to the purpose. For example, examples of the other step include a surface treatment step of a substrate, a pre heating step (a pre baking step), a curing treatment step, a post heating step (a post baking step), and the like.

<<Pre Heating Step and Post Heating Step>>

A heating temperature in the pre heating step and the post heating step is preferably 80° C. to 200° C. The upper limit is preferably lower than or equal to 150° C. The lower limit is preferably higher than or equal to 90° C.

A heating time in the pre heating step and the post heating step is preferably 30 to 240 seconds. The upper limit is preferably shorter than or equal to 180 seconds. The lower limit is preferably longer than or equal to 60 seconds.

<<Curing Treatment Step>>

The curing treatment step is a step of performing a curing treatment with respect to the formed film described above, as necessary, and mechanical strength of the near infrared ray cut filter is improved by performing the curing treatment.

The curing treatment step is not particularly limited, and can be suitably selected according to the purpose. Examples of the curing treatment step preferably include an overall exposure treatment, an overall heat treatment, and the like. Here, in the present invention, "the exposure" is used as the meaning including not only irradiation of light rays at various wavelengths but also radiation irradiation of an electron beam, an X-ray, and the like.

It is preferable that the exposure is performed by radiation irradiation, and in particular, an electron beam, KrF, ArF, and an ultraviolet ray or visible light such as a g ray, an h ray, and an i ray are preferably used as radiation which can be used at the time of performing the exposure.

Examples of an exposure method include stepper exposure, exposure using a high-pressure mercury lamp, and the like.

An exposure amount is preferably 5 to 3,000 mJ/cm$^2$. The upper limit is preferably less than or equal to 2,000 mJ/cm$^2$, is more preferably less than or equal to 1,000 mJ/cm$^2$. The lower limit is preferably greater than or equal to 10 mJ/cm$^2$, and is more preferably greater than or equal to 50 mJ/cm$^2$.

Examples of a method of the overall exposure treatment include a method of exposing the entire surface of the formed film. In a case where the near infrared ray absorbent composition contains a polymerizable compound, curing of the polymerizable compound is accelerated by the overall exposure, and the film is further cured, and thus, mechanical strength and durability are improved.

A device performing the overall exposure is not particularly limited, can be suitably selected according to the purpose, and examples of the device preferably include a UV exposing machine such as a super high-pressure mercury lamp, and the like.

In addition, examples of a method of the overall heat treatment include a method of heating the entire surface of the formed film described above. Film hardness of the pattern becomes higher by the overall heating.

A heating temperature in the overall heating is preferably 100° C. to 260° C. The lower limit is preferably higher than or equal to 120° C., and is more preferably higher than or equal to 160° C. The upper limit is preferably lower than or equal to 240° C., and is more preferably lower than or equal to 220° C. In a case where the heating temperature is in the range described above, a film having excellent strength is easily obtained.

A heating time in the overall heating is preferably 1 to 180 minutes. The lower limit is preferably longer than or equal to 3 minutes. The upper limit is preferably shorter than or equal to 120 minutes.

A device performing the overall heating is not particularly limited, can be suitably selected from known devices according to the purpose, and examples of the device include a dry oven, a hot plate, an IR heater, and the like.

<Camera Module and Manufacturing Method of Camera Module>

A camera module of the present invention includes a solid image pickup element, and a near infrared ray cut filter disposed on the solid image pickup element on a light receiving side.

In addition, a manufacturing method of the camera module of the present invention includes a step of applying the near infrared ray absorbent composition of the present invention described above onto the solid image pickup element on the light receiving side.

FIG. 1 is a schematic sectional view illustrating a configuration of a camera module including a near infrared ray cut filter according to an embodiment of the present invention.

A camera module 10, for example, includes a solid image pickup element 11, a planarizing layer 12 disposed on the solid image pickup element on a main surface side (a light receiving side), a near infrared ray cut filter 13, and a lens holder 15 which is disposed on the upper portion of the near infrared ray cut filter and includes an imaging lens 14 in an internal space.

In the camera module 10, an incidence ray hv from the outside is sequentially transmitted through the imaging lens 14, the near infrared ray cut filter 13, and the planarizing layer 12, and then, arrives at an image pickup element unit of the solid image pickup element 11.

The solid image pickup element 11, for example, includes a photodiode, an interlayer insulating film (not illustrated), a base layer (not illustrated), a color filter 17, over coat (not illustrated), and a micro lens 18 on a main surface of a silicon substrate 16 which is a base substrate, in this order. The color filter 17 (a red color filter, a green color filter, and a blue color filter) or the micro lens 18 are respectively arranged to correspond to the solid image pickup element 11.

In addition, the near infrared ray cut filter 13 may be disposed on the surface of the micro lens 18, between the base layer and the color filter 17, or between the color filter 17 and the over coat, instead of disposing the near infrared ray cut filter 13 on the surface of the planarizing layer 12. For example, the near infrared ray cut filter 13 may be disposed in a position of less than or equal to 2 mm (more preferably less than or equal to 1 mm) from the surface of the micro lens. In a case where the infrared ray cut filter 13 is disposed in such a position, it is possible to simplify a step of forming a near infrared ray cut filter, and to sufficiently cut an unnecessary near infrared ray with respect to the micro lens, and thus, it is possible to further increase near infrared ray shielding properties.

The near infrared ray cut filter of the present invention can be provided to a solder reflow step. By manufacturing the camera module using according to the solder reflow step, it is possible to realize automatic mounting of an electronic component mountable substrate which is required to be soldered, and to remarkably improve productivity, compared to a case where the solder reflow step is not used. Further, the mounting can be automatically performed, and thus, it is possible to reduce costs. In a case where the near infrared ray cut filter is provided to the solder reflow step, the is near infrared ray cut filter is exposed at a temperature of approximately 250° C. to 270° C., and thus, it is preferable that the near infrared ray cut filter has heat resistance (hereinafter, also referred to as "solder reflow resistance") with respect to the solder reflow step.

Herein, "having solder reflow resistance" indicates that properties as the near infrared ray cut filter are retained before and after performing heating at 200° C. for 10 minutes. More preferably, properties are retained before and after performing heating at 230° C. for 10 minutes. Even more preferably, properties are retained before and after performing heating at 250° C. for 3 minutes. In a case where the near infrared ray cut filter does not have solder reflow resistance, there is a case where near infrared ray shielding properties of the near infrared ray cut filter decrease, or a function as a film becomes insufficient in a case where the conditions described above are retained.

In addition, the present invention relates to a manufacturing method of a camera module including a step of performing a reflow treatment. The near infrared ray cut filter of the present invention maintains near infrared ray shielding properties even in the reflow step, and thus, properties of the camera module which is downsized and lightened, and has high performance are not impaired.

Figure 2:
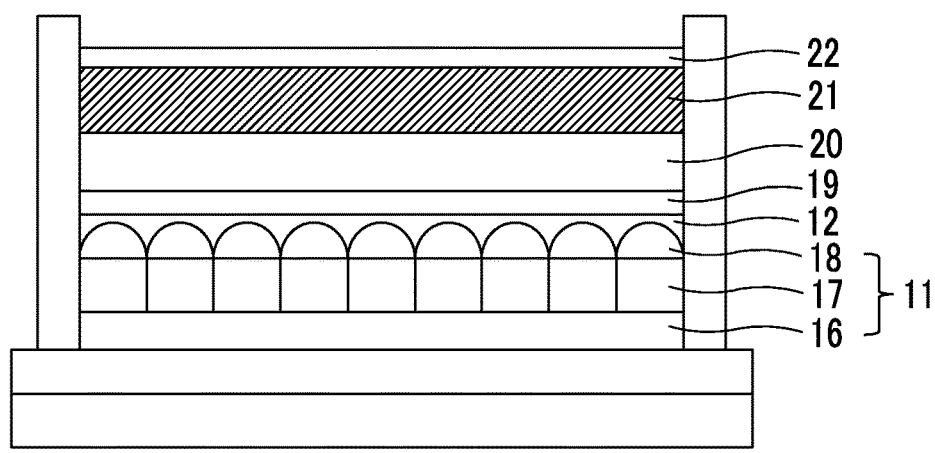
FIG. 2 is a schematic sectional view illustrating an example of a peripheral portion of the near infrared ray cut filter of the camera module.
Figure 3:
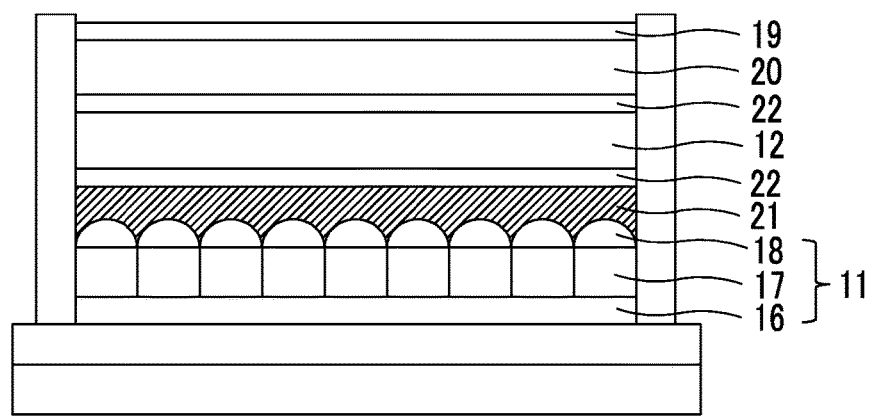
FIG. 3 is a schematic sectional view illustrating another example of the peripheral portion of the near infrared ray cut filter of the camera module.
Figure 4:
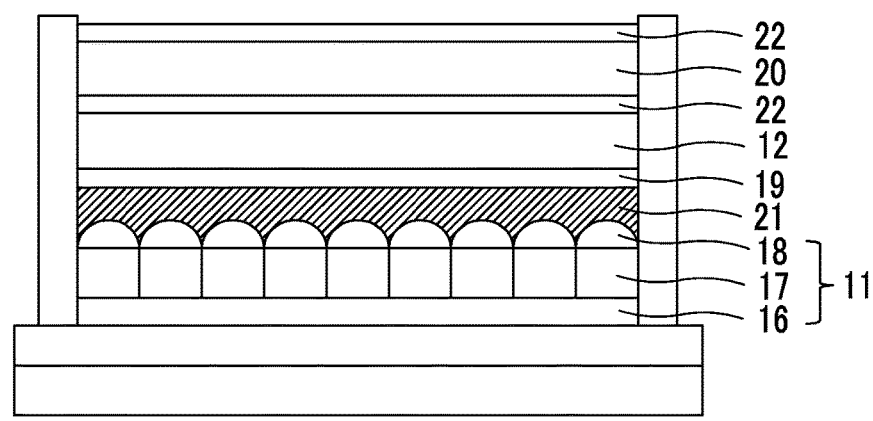
FIG. 4 is a schematic sectional view illustrating still another example of the peripheral portion of the near infrared ray cut filter of the camera module.

FIGS. 2 to 4 are schematic sectional views illustrating examples of a near infrared ray cut filter peripheral portion of the camera module.

As illustrated in FIG. 2, the camera module may include the solid image pickup element 11, the planarizing layer 12, an ultraviolet and infrared light reflection film 19, a transparent substrate 20, a near infrared ray absorption layer (a near infrared ray cut filter) 21, and an antireflection layer 22 in this order.

The ultraviolet and infrared light reflection film 19 has an effect of applying or increasing a function of a near infrared ray cut filter, and for example, can be referred to paragraphs 0033 to 0039 of JP2013-68688A, and the contents thereof are incorporated herein.

The transparent substrate 20 transmits light at a wavelength in a visible range, and for example, can be referred to paragraphs 0026 to 0032 of JP2013-68688A, and the contents thereof are incorporated herein.

The near infrared ray absorption layer 21 can be formed by applying the near infrared ray absorbent composition of the present invention described above.

The antireflection layer 22 has a function of efficiently using an incidence ray by further improving a transmittance by preventing light incident on the near infrared ray cut filter from being reflected, and for example, can be referred to paragraph 0040 of JP2013-68688A, and the contents thereof are incorporated herein.

As illustrated in FIG. 3, the camera module includes the solid image pickup element 11, the near infrared ray absorption layer (the near infrared ray cut filter) 21, the antireflection layer 22, the planarizing layer 12, the antireflection layer 22, the transparent substrate 20, and the ultraviolet and infrared light reflection film 19, in this order.

As illustrated in FIG. 4, the camera module includes the solid image pickup element 11, the near infrared ray absorption layer (the near infrared ray cut filter) 21, the ultraviolet and infrared light reflection film 19, the planarizing layer 12, the antireflection layer 22, the transparent substrate 20, and the antireflection layer 22, in this order.

In addition, the solid image pickup element can have a configuration of an image pickup element according to First to Fourteenth Embodiments disclosed in 0049 and subsequent paragraphs of the pamphlet of WO14/061188A.

EXAMPLES

Hereinafter, the present invention will be described in detail with reference to examples. Materials, use amounts, ratios, treatment contents, treatment sequences, and the like of the following examples can be suitably changed unless the changes cause deviance from the gist of the present invention. Accordingly, the range of the present invention will not be restrictively interpreted by the following specific examples. In addition, "%" and "parts" are based on mass, unless otherwise noted.

In the examples, the following abbreviations were used.
<Curable Compound>
KAYARAD DPHA: (manufactured by Nippon Kayaku Co., Ltd., a mixture of dipentaerythritol pentaacrylate and dipentaerythritol hexaacrylate)
JER157S65: (manufactured by Mitsubishi Chemical Corporation, specialized novolac type epoxy resin)
KAYARAD D-320: (manufactured by Nippon Kayaku Co., Ltd., dipentaerythritol tetraacrylate)
M-510: (manufactured by TOAGOSEI CO., LTD., polybasic acid-modified acryl oligomer)
M-520: (manufactured by TOAGOSEI CO., LTD., polybasic acid-modified acryl oligomer)
DPCA-60: (manufactured by Nippon Kayaku Co., Ltd., hexafunctional acrylate having six pentyleneoxy chains)
<Solvent>
PGMEA: propylene glycol monomethyl ether acetate
[Synthesis of Copper Complex]

Synthesis Example of Copper Complex Cu3-6

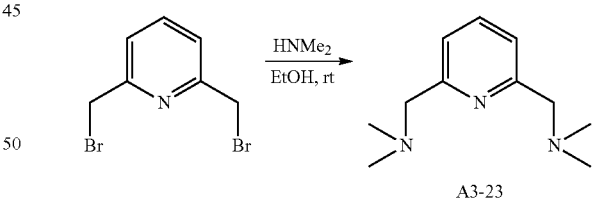

4.0 g of 2,6-bis(bromomethyl) pyridine (manufactured by Tokyo Chemical Industry Co., Ltd.) and 30 mL of 33% ethanol solution of dimethylamine (manufactured by Sigma-Aldrich Co., LLC.) were introduced into a 200 mL flask, stirred at room temperature for 3 hours, and kept at room temperature for 2 days. Precipitated white solid (dimethylamine hydrogen bromide salt) was removed by filtering, a crude product obtained by concentrating the filtrate under reduced pressure was separated by using a saturated aqueous solution of sodium bicarbonate and ethyl acetate, an organic phase obtained was pre-dried over anhydrous sodium sulfate and then concentrated under reduced pressure, and 1.0 g of a compound A3-23 was obtained.

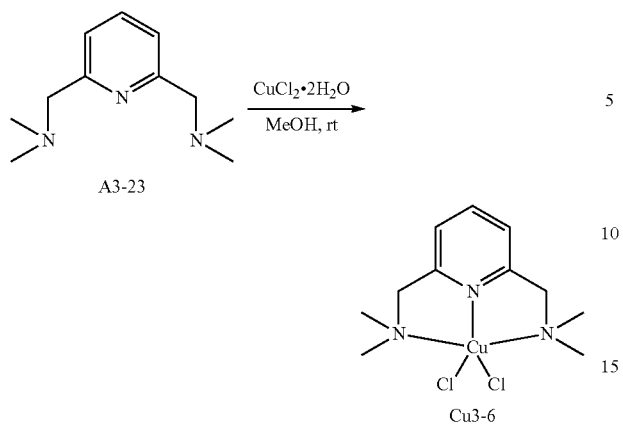

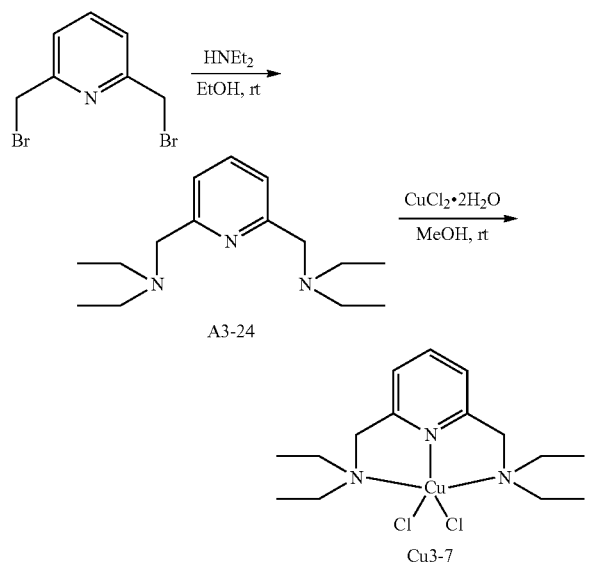

38 mg of the compound A3-23 and 1 mL of methanol were added into a 10 mL flask while stirring the mixture at room temperature, and 34 mg of copper (II) chloride dihydrate (manufactured by Wako Pure Chemical Industries, Ltd.) was introduced thereto and the resultant was stirred for 10 minutes. A blue solution obtained was dried under reduced pressure, and thus, a copper complex Cu3-6 was obtained as a green solid.

Synthesis Example of Copper Complex Cu3-7

A copper complex Cu3-7 was synthesized by the same method as that of the copper complex Cu3-6 according to a scheme described above.

Synthesis Example of Copper Complex Cu3-10

A compound A3-43 was synthesized by a method disclosed in a document (J. Organomet. Chem. 2009, 694, 2636). A copper complex Cu3-10 was synthesized by the same method as that of the copper complex Cu3-6 by using the compound A3-43.

Synthesis Example of Copper Complex Cu3-15

A compound A3-52 was synthesized by a method disclosed in a document (Tetrahedron 1998, 54, 2365). A copper complex Cu3-15 was synthesized by the same method as that of the copper complex Cu3-6 by using the compound A3-52.

Synthesis Example of Copper Complex Cu3-16

A compound A3-54 was commercially available by Tokyo Chemical Industry Co., Ltd., and a copper complex Cu3-16 was synthesized by the same method as that of the copper complex Cu3-6 by using the compound A3-54.

Synthesis Example of Copper Complex Cu3-35

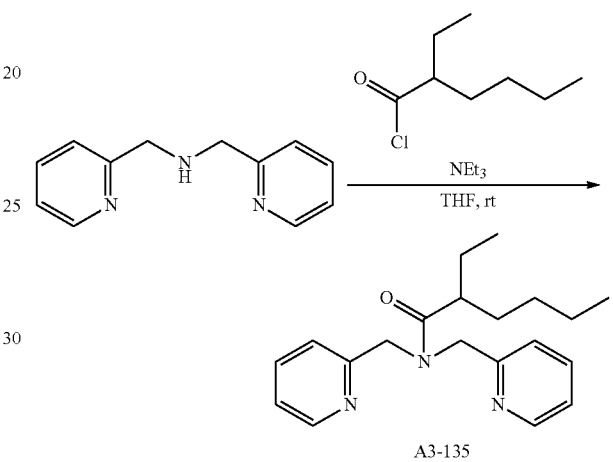

19.9 g of bis(2-pyridylmethyl) amine, 13.3 g of triethylamine, and 150 mL of tetrahydrofuran were introduced into a 300 mL flask and stirred at room temperature. 16.5 g of 2-ethylhexanoyl chloride was added thereto dropwise while performing water cooling, and the mixture was stirred at room temperature for 3 hours. The mixture was separated by using water and ethyl acetate, and an organic phase obtained was pre-dried over anhydrous magnesium sulfate and then concentrated under reduced pressure. This crude product was purified by a silica gel column chromatography (Developing solvent: Hexane/Ethyl Acetate), and thus, 10 g of a compound A3-135 was obtained. A copper complex Cu3-35 was synthesized by the same method as that of the copper complex Cu3-6 by using the compound A3-135 obtained.

Synthesis Example of Copper Complex Cu3-56

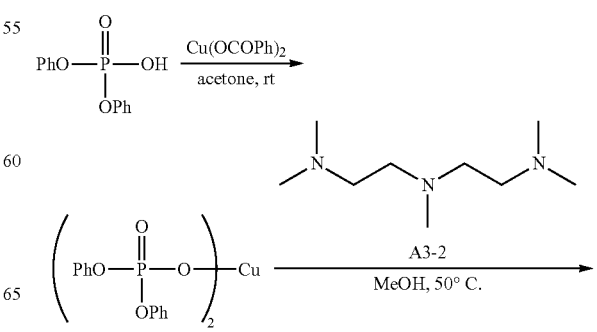

-continued

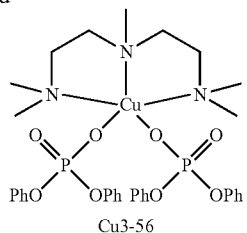

Cu3-56

2 moles of diphenyl phosphate (manufactured by Tokyo Chemical Industry Co., Ltd.) was added to 1 mole of copper benzoate (manufactured by Kanto Chemical Co., Inc.) and stirred in acetone at room temperature for 3 hours, hexane was added thereto, and thus, copper (II) bis(diphenyl phosphate) was obtained. This was dissolved in methanol, and 1 mole of a compound A3-2 (manufactured by Tokyo Chemical Industry Co., Ltd.) was added thereto and stirred for 10 minutes. A blue solution obtained was dried under reduced pressure, and thus, a copper complex Cu3-56 was obtained.

Synthesis Example of Copper Complex Cu3-63

A copper complex Cu3-63 was synthesized by the same method as that of the copper complex Cu3-35 by using copper (II) acetate monohydrate (manufactured by Wako Pure Chemical Industries, Ltd.) instead of copper (II) chloride dihydrate.

Synthesis Example of Copper Complex Cu4-36

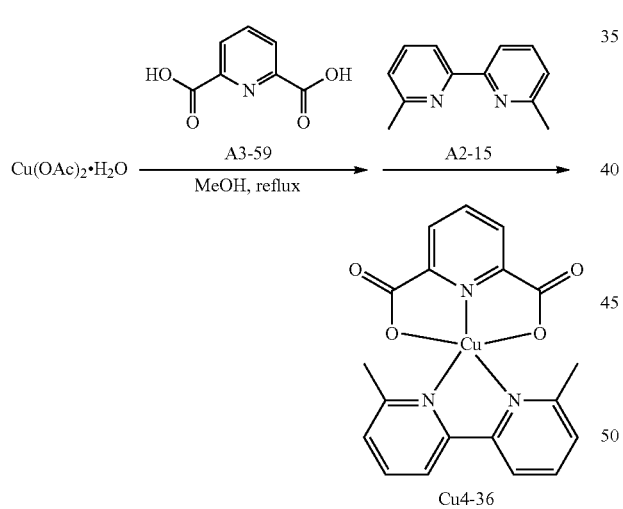

1.99 g of copper (II) acetate monohydrate (manufactured by Wako Pure Chemical Industries, Ltd.), 1.67 g of a compound A3-59 (manufactured by Wako Pure Chemical Industries, Ltd.), and 20 mL of methanol were introduced into a 100 mL flask, and heating and refluxing were performed for 10 minutes. 1.84 g of a compound A2-15 (manufactured by Tokyo Chemical Industry Co., Ltd.) was added thereto, and heating and refluxing were further performed for 10 minutes. The solvent was concentrated under reduced pressure to have approximately 5 mL, 20 mL of water was added thereto, and thus, a precipitated solid was collected by filtering, and then, a copper complex Cu4-36 was obtained as a blue solid.

Synthesis Example of Copper Complex Cu4-39

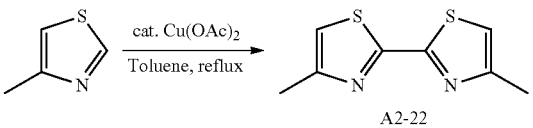

5.0 g of 4-methylthiazole (manufactured by Tokyo Chemical Industry Co., Ltd.), 1.83 g of copper acetate (anhydrous) (manufactured by Wako Pure Chemical Industries, Ltd.), and 100 mL of toluene were added into a 200 mL flask, and heating and refluxing were performed for 12 hours. After cooling the mixture at room temperature, precipitates were filtered by adding water, and the mixture was separated and extracted by adding ethyl acetate to the filtrate. An organic phase obtained was pre-dried over anhydrous magnesium sulfate and concentrated under reduced pressure, a brown crude product (containing a minute amount of the raw material) obtained was crystallized again by using methanol, and thus, a compound A2-22 was obtained as a light yellow solid. A copper complex Cu4-39 was synthesized by the same method as that of the copper complex Cu4-36 by using this compound.

Synthesis Example of Copper Complex Cu4-45

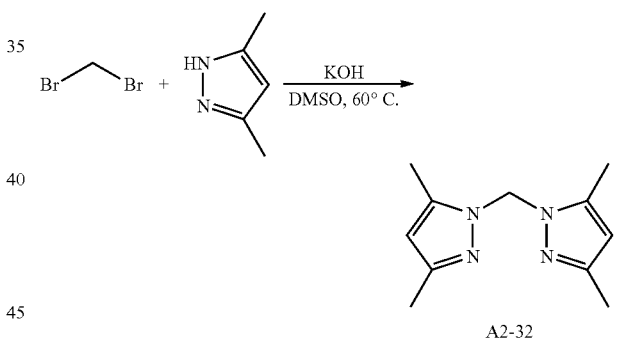

10 g of 3,5-dimethylpyrazole (manufactured by Tokyo Chemical Industry Co., Ltd.) and 60 mL of dimethylsulfoxide were added into a 500 mL three-necked flask under a nitrogen atmosphere and stirred. 23.3 g of potassium hydroxide (manufactured by Wako Pure Chemical Industries, Ltd.) was gradually added thereto and stirred at 60 degrees for 1 hour. 9 g of dibromomethane (manufactured by Wako Pure Chemical Industries, Ltd.) dissolved in 40 mL of dimethylsulfoxide was added thereto dropwise and stirred at 60 degrees for 4 hours. After cooling to room temperature, 200 mL of water was added dropwise, extraction was performed with chloroform, washing was performed with water and a saturated saline, an organic phase obtained was concentrated under reduced pressure, and thus, a compound A2-32 was obtained as a white solid. A copper complex Cu4-45 was synthesized by the same method as that of the copper complex Cu4-36 by using this compound.

Synthesis Example of Copper Complex Cu4-49

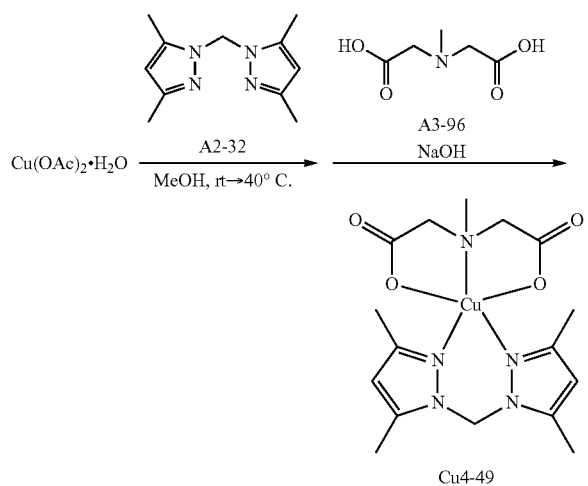

0.20 g of the compound A2-32, 0.19 g of copper (II) acetate monohydrate (manufactured by Wako Pure Chemical Industries, Ltd.), and 10 mL of methanol were added into a 100 mL flask, heated from room temperature to 40 degrees while stirring, and stirred for 30 minutes. When the materials were slowly dissolved and a blue solution is obtained, 0.15 g of a compound A3-96 (manufactured by Tokyo Chemical Industry Co., Ltd.) and 10 mL of a methanol solution obtained by dissolving 0.16 g of an aqueous solution of 50 mass % sodium hydroxide were added dropwise. The precipitated blue solid was slowly collected by filtering, and 0.16 g of a copper complex Cu4-49 was obtained.

Synthesis Example of Copper Complex Cu4-50

A copper complex Cu4-50 was synthesized by the same method as that of the copper complex Cu4-49 by using a compound A3-97 which is commercially available from Wako Pure Chemical Industries, Ltd.

Synthesis Example of Copper Complex Cu4-52

A copper complex Cu4-52 was synthesized by the same method as that of the copper complex Cu4-49 by using a compound A3-103 which is commercially available from Tokyo Chemical Industry Co., Ltd. as chelidamic acid monohydrate.

Synthesis Example of Copper Complex Cu4-55

A copper complex Cu4-55 was synthesized by the same method as that of the copper complex Cu4-36 by using a compound A2-36 which was synthesized by the same method as that of the compound A2-32 by using 3,5-diisopropylpyrazole (manufactured by Tokyo Chemical Industry Co., Ltd.) instead of 3,5-dimethylpyrazole.

Synthesis Example of Copper Complex Cu4-62

A copper complex Cu4-62 was synthesized by the same method as that of the copper complex Cu4-36 by using a compound A2-26 which was synthesized by the same method as that of the compound A2-32 by using 3,5-diisopropylpyrazole (manufactured by Tokyo Chemical Industry Co., Ltd.) instead of 3,5-dimethylpyrazole and using 2-chloromethylpyridine hydrochloride (manufactured by Tokyo Chemical Industry Co., Ltd.) instead of dibromomethane.

Synthesis Example of Copper Complex Cu4-63

A copper complex Cu4-63 was synthesized by the same method as that of the copper complex Cu4-36 by using a compound A2-28 which is commercially available from Tokyo Chemical Industry Co., Ltd.

Synthesis Example of Copper Complex Cu5-1

A reaction liquid which was obtained by mixing a compound A4-1 (manufactured by Tokyo Chemical Industry Co., Ltd.) and copper (II) chloride dihydrate (manufactured by Wako Pure Chemical Industries, Ltd.) at a molar ratio of 1:1 in methanol and stirring the mixture for 10 minutes was dried under reduced pressure, and thus, a copper complex Cu5-1 was obtained.

Synthesis Example of Copper Complex Cu5-18

A copper complex Cu5-18 was synthesized by the same method as that of the copper complex Cu5-1 by using a compound A4-61 (manufactured by Tokyo Chemical Industry Co., Ltd.).

Synthesis Example of Copper Complex Cu5-20

A copper complex Cu5-20 was synthesized by the same method as that of the copper complex Cu5-1 by using a compound A4-63 (manufactured by Tokyo Chemical Industry Co., Ltd.).

Synthesis Example of Copper Complex Cu5-22

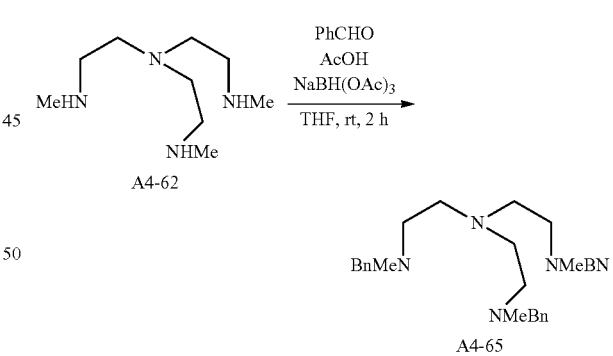

0.93 g of a compound A4-62, 30 mL of tetrahydrofuran, 2.34 g of benzaldehyde, and 0.90 g of acetic acid were added into a 100 mL three-necked flask under a nitrogen atmosphere and stirred at 0 degree. 3.78 g of sodium triacetoxyborohydride (manufactured by Tokyo Chemical Industry Co., Ltd.) was added thereto and stirred at room temperature for 2 hours. After adding 50 mL of water dropwise, concentrated hydrochloric acid was gradually added thereto to set the pH as 1, and liquid separating and extraction were performed three times using 50 mL of ethyl acetate, and a water phase was collected. An aqueous solution of 50 mass % sodium hydroxide was gradually added to this water phase to set the pH as 10, liquid separating and extraction were performed three times using 50 mL of ethyl acetate, and an organic phase was collected. After performing pre-drying over anhydrous magnesium sulfate and concentrating under reduced pressure, 1.90 g of a compound A4-65 was obtained as light yellow oil. A copper complex Cu5-22 was synthesized by the same method as that of Cu5-1 by using this compound A4-65.

Synthesis Example of Copper Complex Cu5-37

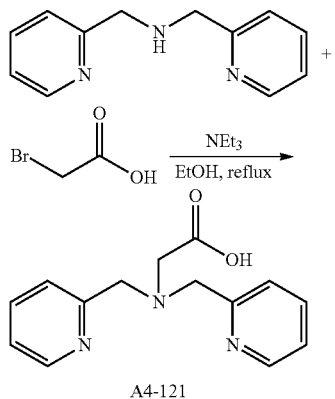

A4-121

1.99 g of bis(2-pyridylmethyl) amine (manufactured by Tokyo Chemical Industry Co., Ltd.), 20 mL of ethanol, and 1.01 g of triethylamine were added into a 100 mL flask, 1.49 g of bromoacetic acid (manufactured by Kanto Chemical Co., Inc.) was added dropwise while stirring the mixture at room temperature, and heating and refluxing were performed for 5 hours. After cooling the mixture to room temperature, ethyl acetate was added to a crude product obtained by concentrating a reaction liquid under reduced pressure, a precipitated solid was dispersed and washed with methanol, filtering was performed, and thus, 0.5 g of a compound A4-121 was obtained. A copper complex Cu5-37 was synthesized by the same method as that of the copper complex Cu5-1 by using this compound.

Synthesis Example of Copper Complex Cu5-46

The compound A4-1 (manufactured by Tokyo Chemical Industry Co., Ltd.) and copper (II) sulfate pentahydrate (manufactured by Wako Pure Chemical Industries, Ltd.) were mixed in methanol at a molar ratio of 1:1 and stirred for 30 minutes. Ethyl acetate was added to this reaction liquid, a precipitated solid was collected by filtering, and a copper complex Cu5-46 was obtained.

Synthesis Example of Copper Complex Cu5-50

A copper complex Cu5-50 was synthesized by the same method as that of the copper complex Cu5-46 by using the compound A4-61 (manufactured by Tokyo Chemical Industry Co., Ltd.).

Synthesis Example of Copper Complex Cu5-51

A copper complex Cu5-51 was synthesized by the same method as that of the copper complex Cu5-46 by using a compound A4-62 (manufactured by Sigma-Aldrich Co., LLC.).

Synthesis Example of Copper Complex Cu5-52

A copper complex Cu5-52 was synthesized by the same method as that of the copper complex Cu5-46 by using the compound A4-63 (manufactured by Tokyo Chemical Industry Co., Ltd.).

Synthesis Example of Copper Complex Cu5-72

The copper complex Cu5-1 was dissolved in water, and an excessive amount of an aqueous solution of saturated sodium tetrafluoroborate (manufactured by Wako Pure Chemical Industries, Ltd.) was added while stirring. A precipitated solid was collected by filtering and a copper complex Cu5-72 was obtained.

Synthesis Example of Copper Complex Cu5-82

A copper complex Cu5-82 was synthesized by the same method as that of Cu5-72 by using the compound A4-62 (manufactured by Sigma-Aldrich Co., LLC.) instead of the compound A4-1 used in the synthesis of the copper complex Cu5-1 and using lithium tetrakis(pentafluorophenyl)borate (manufactured by Tokyo Chemical Industry Co., Ltd.) instead of sodium tetrafluoroborate.

Synthesis Example of Copper Complex Cu5-83

A copper complex Cu5-83 was synthesized by the same method as that of the copper complex Cu5-82 by using the compound A4-63 (manufactured by Tokyo Chemical Industry Co., Ltd.).

Synthesis Example of Copper Complex Cu5-92

A copper complex Cu5-92 was synthesized by the same method as that of Cu5-72 by using lithium bis(trifluoromethanesulfone)imide instead of sodium tetrafluoroborate.

Synthesis Example of Copper Complex Cu5-95

A copper complex Cu5-95 was synthesized by the same method as that of the copper complex Cu5-92 by using the compound A4-63 (manufactured by Tokyo Chemical Industry Co., Ltd.).

Synthesis Example of Copper Complex Cu5-96

A copper complex Cu5-96 was synthesized by the same method as that of the copper complex Cu5-18 by using copper (II) bromide (manufactured by Kanto Chemical Co., Inc.) instead of copper (II) chloride dihydrate.

Synthesis Example of Copper Complex Cu5-97

A copper complex Cu5-97 was synthesized by the same method as that of the copper complex Cu5-82 by using a compound A4-188 (manufactured by Sigma-Aldrich Co., LLC.).

Synthesis Example of Copper Complex Cu5-98

A copper complex Cu5-98 was synthesized by the same method as that of Cu5-83 by using potassium tris(trifluoromethanesulfonyl)methide instead of lithium tetrakis(pentafluorophenyl)borate.

Synthesis Example of Copper Complex Cu5-99

A copper complex Cu5-99 was synthesized by the same method as that of Cu5-83 by using copper (II) acetate monohydrate instead of copper (II) chloride dihydrate.

Synthesis Example of Copper Complex Cu5-100

A copper complex Cu5-100 was synthesized by the same method as that of Cu5-83 by using copper (II) bromide instead of copper (II) chloride dihydrate.

Synthesis Example of Copper Complex Cu5-101

A copper complex Cu5-101 was synthesized by causing a reaction of 1 mole of trifluoromethanesulfonamide (manufactured by Wako Pure Chemical Industries, Ltd.) with Cu5-46 and precipitating a complex by the same method as that of Cu5-80 or Cu5-82.

Synthesis Example of Copper Complex Cu5-102

A copper complex Cu5-102 was synthesized by the same method as that of Cu5-82 by using copper (II) acetate monohydrate instead of copper (II) chloride dihydrate.

Synthesis Example of Copper Complex Cu5-103

A copper complex Cu5-103 was synthesized by the same method as that of Cu5-82 by using copper (II) benzoate instead of copper (II) chloride dihydrate.

Synthesis Example of Copper Complex Cu5-104

A copper complex Cu5-104 was synthesized by adding lithium bis(trifluoromethanesulfone)imide to an aqueous solution of Cu5-46 and precipitating a complex.

Synthesis Example of Copper Complex Cu5-105

A copper complex Cu5-105 was synthesized by the same method as that of Cu5-72 by using the compound A4-65.

Synthesis Example of Copper Complex Cu5-106

12 g of 6-methyl-2-pyridinemethanol (manufactured by Tokyo Chemical Industry Co., Ltd.) and 100 mL of tetrahydrofuran were added into a 300 mL three-necked flask under a nitrogen atmosphere and stirred at room temperature. After adding 25 g of phosphorus tribromide (manufactured by Tokyo Chemical Industry Co., Ltd.) dropwise while cooling the mixture with ice, and then, the mixture was stirred at room temperature overnight. An aqueous solution of saturated ammonium chloride and ethyl acetate were added thereto to perform liquid separating and extraction, an organic phase obtained was concentrated, a product was purified by a silica gel column chromatography (Developing solvent: Hexane/Ethyl Acetate), and thus, 6-methyl-2-(bromomethyl) pyridine was obtained as light red oil.

1.86 g of the synthesized 6-methyl-2-(bromomethyl) pyridine and 10 mL of water were added into a 100 mL flask and stirred at 0 degree. 1.08 g of 2-pyridylmethylamine was added thereto and stirred at 0 degree. 2 mL of an aqueous solution of sodium hydroxide having a concentration of 1 mol/L was added thereto and stirred at room temperature overnight. Water and chloroform were added thereto for liquid separating and extraction, and an organic phase obtained was washed with water three times, pre-dried over anhydrous sodium sulfate, and concentrated under reduced pressure, and thus, a compound A4-90 was obtained as a light yellow solid.

A copper complex Cu5-106 was synthesized by the same method as that of the copper complex Cu5-1 by using the compound A4-90.

Synthesis Example of Copper Complex Cu5-117

A copper complex Cu5-117 was synthesized by the same method as that of the copper complex Cu5-72 by using a compound A4-29 synthesized by a method disclosed in a document (Eur. J. Inorg. Chem. 2009, 3921).

Synthesis Example of Copper Complex Cu5-118

A copper complex Cu5-118 was synthesized by the same method as that of Cu5-82 by using the compound A4-65.

Synthesis Example of Copper Complex Cu5-119

A copper complex Cu5-119 was synthesized by the same method as that of Cu5-46 by using the compound A4-65.

Synthesis Examples of Copper Complexes Cu5-120 and Cu5-122

Copper complexes Cu5-120 and Cu5-122 were synthesized by the same method as that of Cu5-83 by using lithium bis(pentafluoroethanesulfonyl)imide or lithium 4,4,5,5,6,6-hexafluorodihydro-4H-1,3,2-dithiazine 1,1,3,3,-tetraoxide instead of lithium tetrakis(pentafluorophenyl)borate.

Synthesis Example of Copper Complex Cu5-123

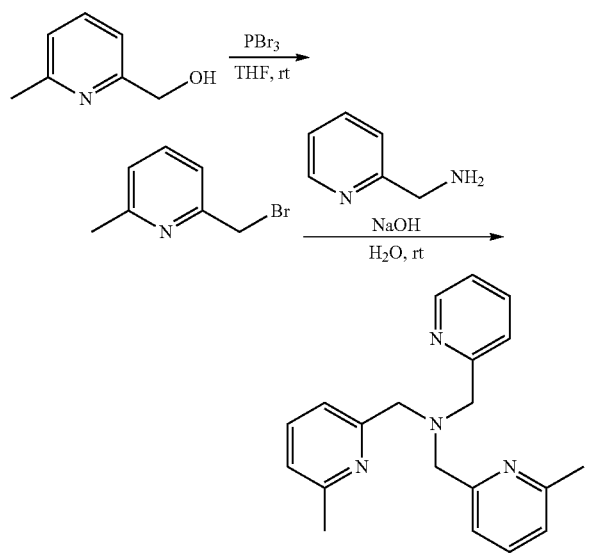

A4-90

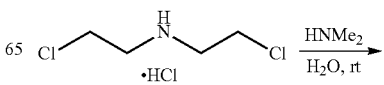

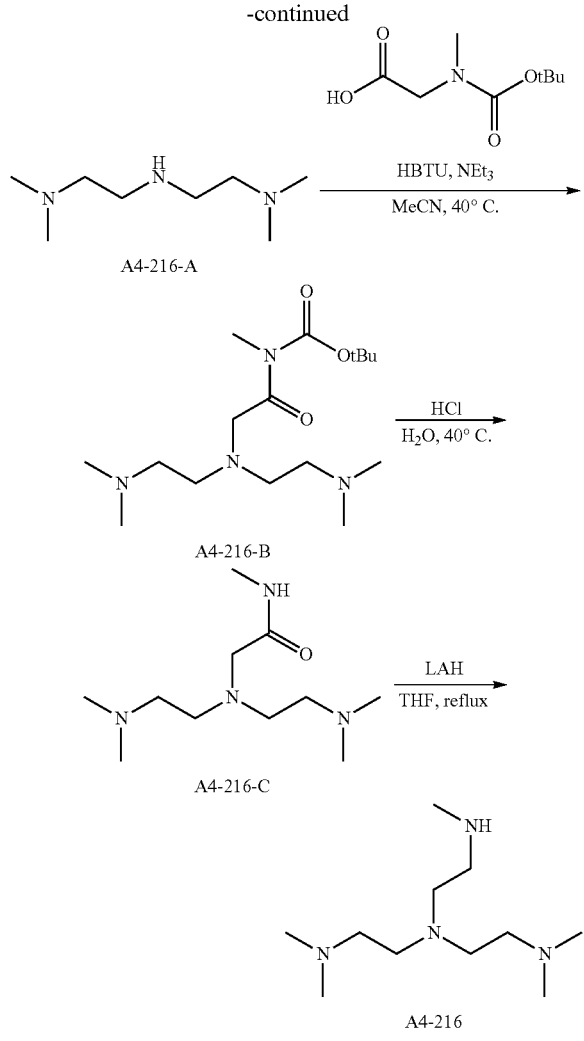

4.1 g of the compound A4-216-B and 10 mL of water were added into a flask, 3.7 mL of concentrated hydrochloric acid was added thereto while stirring the mixture at room temperature, and then, the mixture was stirred at 40° C. for 2 hours. After adding sodium hydroxide to this reaction liquid to obtain a basic aqueous solution, an organic phase obtained by performing liquid separating and extraction using tert-butyl methyl ether was pre-dried over anhydrous sodium sulfate and concentrated under reduced pressure, and thus, 3.0 g of a compound A4-216-C was obtained.

3.78 g of lithium aluminum hydride and 60 mL of dehydrated tetrahydrofuran were added into a three-necked flask under a nitrogen atmosphere and cooled to 0° C. 3.0 g of the compound A4-216-C and 40 mL of a dehydrated tetrahydrofuran solution were added thereto dropwise, heating and refluxing were performed for 2 hours, and the mixture was cooled to room temperature. Then, 4 mL of water, 4 mL of an aqueous solution of 15 mass % sodium hydroxide, and 12 mL of water were slowly added dropwise in this order, while cooling the mixture with ice. After filtering generated white precipitates, oil obtained by concentrating the filtrate under reduced pressure was dissolved again in tert-butyl methyl ether, pre-dried over anhydrous sodium sulfate, and concentrated again under reduced pressure, and thus, 1.1 g of a compound A4-216 was obtained.

A copper complex Cu5-123 was synthesized by the same method as that of the copper complex Cu5-82 by using this compound A4-216.

Synthesis Example of Copper Complex Cu5-125

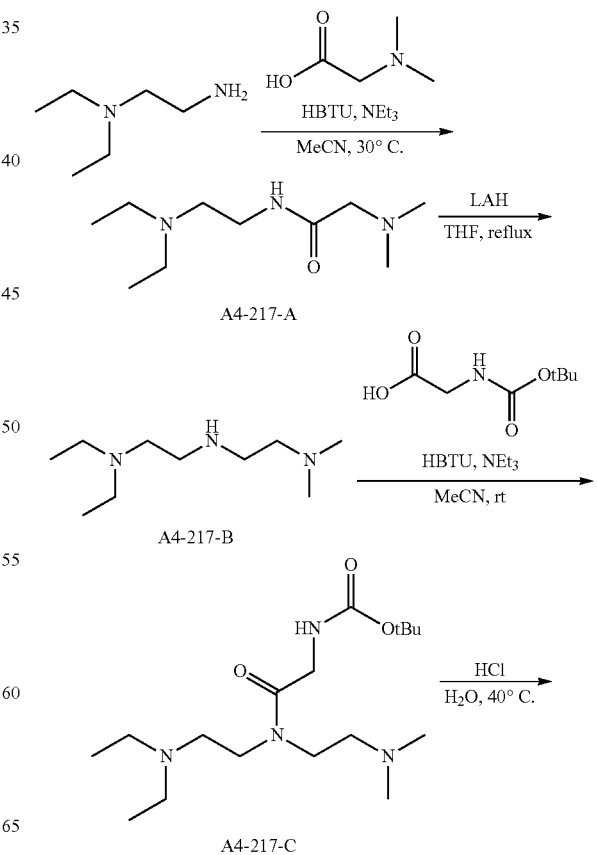

101 g of bis(2-chloroethyl)amine hydrochloride and 200 mL of water were added into a three-necked flask and stirred at room temperature. 600 mL of an aqueous solution of 50 mass % dimethylamine was added thereto dropwise and stirred at room temperature for 7 days. 150 g of sodium hydroxide and 100 mL of t-butyl methyl ether were added thereto, an organic phase obtained by liquid separating was pre-dried over anhydrous sodium sulfate and then concentrated under reduced pressure, and thus, 24.4 g of a compound A4-216-A was obtained.

15.0 g of N-(tert-butoxycarbonyl)-N-methylglycine, 100 mL of acetonitrile, and 12 g of triethylamine were added into a three-necked flask and stirred at room temperature. 38.1 g of O-(benzotriazol-1-yl)-N,N,N',N'-tetramethyluronium hexafluorophosphate (HBTU) was added thereto, 12.0 g of the compound A4-216-A was then added thereto and stirred at 40° C. for 4 hours. 100 mL of a saturated saline was added thereto and a neutral aqueous solution was obtained. A water phase was washed with 150 mL of ethyl acetate three times, 100 mL of an aqueous solution of saturated potassium carbonate was added thereto, and a basic aqueous solution was obtained. An organic phase obtained by performing liquid separating and extraction of the aqueous solution using 150 mL of ethyl acetate three times, was pre-dried over anhydrous sodium sulfate and concentrated under reduced pressure, and thus, 5.7 g of a compound A4-216-B was obtained.

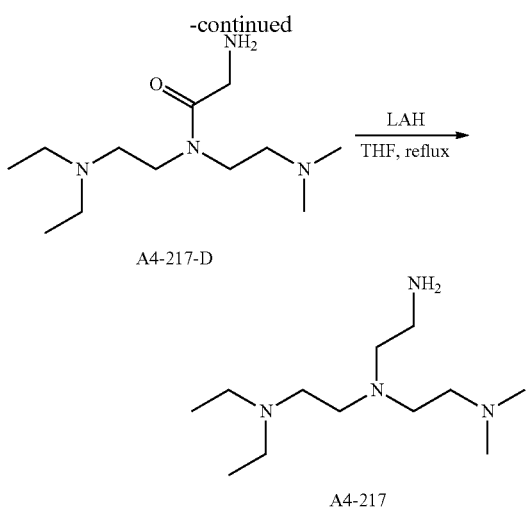

A4-217-D

A4-217

5.13 g of dimethylglycine, 100 mL of acetonitrile, and 6.20 g of triethylamine were added into a 300 mL flask and stirred at room temperature. 20 g of O-(benzotriazol-1-yl)-N,N,N',N'-tetramethyluronium hexafluorophosphate (HBTU) was added thereto, 12.0 g of N,N-diethylethylenediamine was then added thereto and stirred at 30 degrees for 7 hours. A reaction liquid was concentrated under reduced pressure, 100 mL of an aqueous solution of saturated sodium chloride and 100 mL of ethyl acetate were added thereto, and liquid separating was performed. After washing this water phase with 100 mL of ethyl acetate twice, 100 mL of an aqueous solution of saturated potassium carbonate was added thereto, an organic phase obtained by performing liquid separating and extraction of the aqueous solution using 100 mL of ethyl acetate three times, was pre-dried over anhydrous sodium sulfate and concentrated under reduced pressure, and thus, 5.4 g of a compound A4-217-A was obtained.

4.0 g of lithium aluminum hydride and 100 mL of dehydrated tetrahydrofuran were added into a 200 mL three-necked flask under a nitrogen atmosphere and cooled to 0 degree. After adding 4.0 g of the compound A4-217-A dropwise thereto, heating and refluxing were performed for 6 hours, and the mixture was cooled to room temperature. 4 mL of water, 4 mL of an aqueous solution of 15% sodium hydroxide, and 12 mL of water were slowly added dropwise in this order, while cooling the mixture with ice. After filtering generated white precipitates, tert-butyl methyl ether was added to oil obtained by concentrating the filtrate under reduced pressure, the mixture was pre-dried over anhydrous sodium sulfate, and concentrated under reduced pressure, and thus, 2.4 g of a compound A4-217-B was obtained.

1.25 g of the compound A4-217-B, 1.50 g of N-Boc glycine, 30 mL of acetonitrile, and 1.6 g of triethylamine were added into a 200 mL three-necked flask and stirred at room temperature. 5.44 g of O-(benzotriazol-1-yl)-N,N,N',N'-tetramethyluronium hexafluorophosphate (HBTU) was added thereto, and stirred at room temperature overnight. A reaction liquid was concentrated under reduced pressure, 50 mL of a saturated saline and 50 mL of ethyl acetate were added thereto, and liquid separating was performed. After washing the water phase with 50 mL of ethyl acetate three times, 50 mL of an aqueous solution of saturated potassium carbonate was added thereto, an organic phase obtained by performing liquid separating and extraction using 50 mL of ethyl acetate three times, was pre-dried over anhydrous sodium sulfate and concentrated under reduced pressure, and thus, 0.44 g of a compound A4-217-C was obtained.

0.4 g of the compound A4-217-C and 5 mL of water were added into a 100 mL flask, 0.4 mL of concentrated hydrochloric acid was added thereto while stirring the mixture at room temperature, and then, the mixture was stirred at 40° C. for 1 hour. After slowly adding aqueous solution of 50 mass % sodium hydroxide to this reaction liquid to obtain a basic aqueous solution, an organic phase obtained by performing liquid separating and extraction using tert-butyl methyl ether was pre-dried over anhydrous sodium sulfate and concentrated under reduced pressure, and thus, 0.25 g of a compound A4-217-D was obtained.

0.25 g of lithium aluminum hydride and 15 mL of dehydrated tetrahydrofuran were added into a 10 mL three-necked flask under a nitrogen atmosphere and cooled to 0° C. 0.25 g of the compound A4-217-D and 5 mL of a dehydrated tetrahydrofuran solution were added thereto dropwise, heating and refluxing were performed for 5 hours. The mixture were cooled to room temperature, and then, 0.25 mL of water, 0.25 mL of an aqueous solution of 15% sodium hydroxide, and 0.75 mL of water were slowly added dropwise in this order, while cooling the mixture with ice. After filtering generated white precipitates, tert-butyl methyl ether was added to oil obtained by concentrating the filtrate under reduced pressure, the mixture was pre-dried over anhydrous sodium sulfate, and concentrated under reduced pressure, and thus, 0.15 g of a compound A4-217 was obtained.

A copper complex Cu5-125 was synthesized by the same method as that of the copper complex Cu5-82 by using the compound A4-217 obtained.

Synthesis Examples of Copper Complexes Cu5-127 to 152

Copper complexes Cu5-127 to 152 were synthesized by the same method as that of Cu5-83 by using corresponding copper (II) carboxylate. In a case where the copper (II) carboxylate is not commercially available, copper carboxylate is obtained by mixing basic copper carbonate and corresponding carboxylic acid in a water medium at a ratio of 1:2.1 and stirring at 60° C. for 30 minutes.

Synthesis Example of Copper Complex Cu6-52

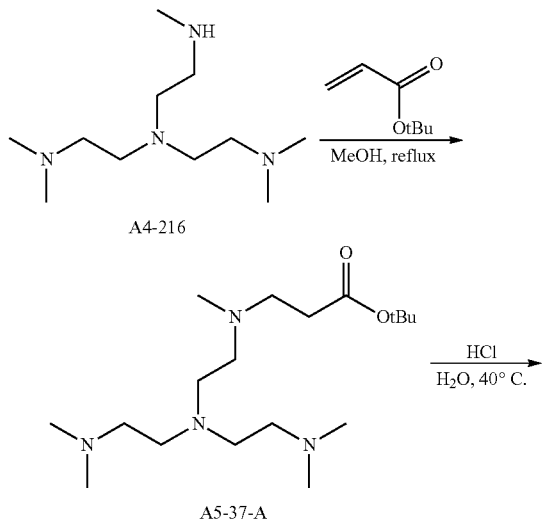

A4-216

A5-37-A

-continued

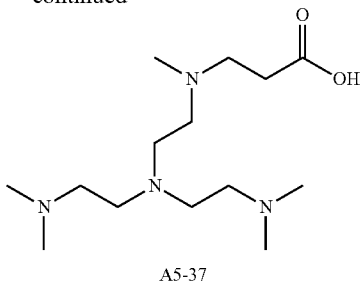

A5-37

1.08 g of the compound A4-216 and 10 mL of methanol were added into a 100 mL flask, 0.80 g of t-butyl acrylate was added thereto while stirring, and heating and refluxing were performed for 2 hours. 1.4 g of a compound A5-37-A was obtained by concentrating the reaction liquid under reduced pressure.

1.3 g of the compound A5-37-A and 5 mL of water were added into a 100 mL flask, 2.0 mL of concentrated hydrochloric acid was added thereto while stirring at room temperature, and then, the mixture was stirred at 50° C. for 6 hours. After performing azeotropic dehydration by adding toluene to this reaction liquid, the reaction liquid was concentrated, and thus, hydrochloride of the compound A5-37 was obtained as a yellow solid. When methanol is added thereto and stirred and triethylamine is added to this suspension, complete dissolution is performed. When triethylamine and ethyl acetate are further added thereto, triethylamine hydrochloride is precipitated, and thus, this is filtered. This operation is repeatedly performed until triethylamine hydrochloride is not precipitated, the solution is finally concentrated, and thus, 1.0 g of a compound A5-37 was obtained.

0.60 g of the compound A5-37 and 20 mL of methanol were added into a 100 mL flask, 170 g of copper (II) chloride dihydrate and 98 mg of copper hydroxide were added thereto while stirring at room temperature, and then the mixture was stirred at 40 degrees for 1.5 hours. After filtering a slight amount of impurities with a filter, 1.52 g of lithium tetrakis(pentafluorophenyl)borate was added thereto, water is slowly added dropwise, crystals obtained were collected by filtering, and thus, a copper complex Cu6-52 was obtained.

<Measurement of Maximum Absorption Wavelength, Molar Light Absorption Coefficient, and Gram Light Absorption Coefficient of Copper Complex>

Various copper complexes were dissolved in solvents shown in the following tables to prepare solutions having a concentration of 1 g/L. Then, absorption spectra of the solutions in which the copper complexes were dissolved were measured with UV-1800 manufactured by Shimadzu Corporation, and a maximum absorption wavelength, a molar light absorption coefficient and a gram light absorption coefficient at the maximum absorption wavelength, and a molar light absorption coefficient and a gram light absorption coefficient at 800 nm were measured. In the tables, DMF represents N,N-dimethylformamide, and MFG represents propylene glycol monomethyl ether.

Evaluation Standard of Maximum Absorption Wavelength

A: The maximum absorption wavelength is obtained in a wavelength range of 700 nm to 1,200 μm.

B: The maximum absorption wavelength is obtained in a wavelength range of less than 700 nm and exceeding 1,200 nm.

TABLE 15

| Copper complex | Maximum absorption wavelength (nm) | Evaluation | Absorption coefficients at maximum absorption wavelength | | Absorption coefficients at 800 nm | | Measurement solvent |
| | | | Molar light absorption coefficient (L/mol · cm) | Gram light absorption coefficient (L/g · cm) | Molar light absorption coefficient (L/mol · cm) | Gram light absorption coefficient (L/g · cm) | |
|---|---|---|---|---|---|---|---|
| Cu3-6  | 780 | A | 249 | 0.725 | 244 | 0.710 | DMF |
| Cu3-7  | 802 | A | 257 | 0.626 | 257 | 0.626 | DMF |
| Cu3-10 | 786 | A | 178 | 0.327 | 176 | 0.323 | DMF |
| Cu3-15 | 890 | A | 170 | 0.369 | 134 | 0.291 | DMF |
| Cu3-16 | 936 | A | 426 | 1.556 | 316 | 1.154 | DMF |
| Cu3-35 | 836 | A | 186 | 0.394 | 181 | 0.383 | DMF |
| Cu3-56 | 740 | A | 189 | 0.236 | 173 | 0.216 | DMF |
| Cu3-63 | 708 | A | 180 | 0.355 | 105 | 0.207 | DMF |
| Cu4-36 | 748 | A | 124 | 0.305 | 107 | 0.263 | DMF |
| Cu4-39 | 760 | A | 126 | 0.291 | 113 | 0.261 | DMF |
| Cu4-45 | 756 | A | 123 | 0.284 | 110 | 0.254 | DMF |
| Cu4-49 | 730 | A | 139 | 0.337 | 107 | 0.259 | $H_2O$ |
| Cu4-50 | 726 | A | 118 | 0.241 | 84  | 0.172 | $H_2O$ |
| Cu4-52 | 756 | A | 121 | 0.268 | 106 | 0.235 | DMF |
| Cu4-55 | 754 | A | 116 | 0.213 | 104 | 0.191 | DMF |
| Cu4-62 | 756 | A | 121 | 0.252 | 108 | 0.225 | DMF |
| Cu4-63 | 754 | A | 120 | 0.291 | 106 | 0.257 | DMF |
| Cu5-1  | 950 | A | 186 | 0.429 | 97  | 0.224 | MFG |
| Cu5-18 | 892 | A | 101 | 0.361 | 92  | 0.329 | MFG |
| Cu5-20 | 932 | A | 450 | 1.233 | 197 | 0.540 | MFG |
| Cu5-22 | 930 | A | 695 | 1.171 | 294 | 0.495 | MFG |
| Cu5-37 | 896 | A | 158 | 0.446 | 135 | 0.381 | DMF |
| Cu5-46 | 874 | A | 197 | 0.421 | 163 | 0.348 | $H_2O$ |
| Cu5-50 | 858 | A | 133 | 0.409 | 122 | 0.375 | $H_2O$ |
| Cu5-51 | 860 | A | 245 | 0.670 | 217 | 0.593 | $H_2O$ |
| Cu5-52 | 878 | A | 462 | 1.132 | 349 | 0.855 | $H_2O$ |
| Cu5-72 | 954 | A | 191 | 0.401 | 99  | 0.208 | MFG |
| Cu5-82 | 920 | A | 195 | 0.202 | 135 | 0.140 | MFG |
| Cu5-83 | 944 | A | 458 | 0.454 | 192 | 0.190 | MFG |

TABLE 15-continued

| | Maximum absorption wavelength | | Absorption coefficients at maximum absorption wavelength | | Absorption coefficients at 800 nm | | |
|---|---|---|---|---|---|---|---|
| Copper complex | Maximum absorption wavelength (nm) | Evaluation | Molar light absorption coefficient (L/mol · cm) | Gram light absorption coefficient (L/g · cm) | Molar light absorption coefficient (L/mol · cm) | Gram light absorption coefficient (L/g · cm) | Measurement solvent |
| Cu5-92 | 968 | A | 217 | 0.323 | 111 | 0.165 | MFG |
| Cu5-95 | 936 | A | 524 | 0.861 | 229 | 0.376 | MFG |
| Cu5-96 | 862 | A | 121 | 0.327 | 112 | 0.303 | $H_2O$ |
| Cu5-97 | 882 | A | 156 | 0.149 | 132 | 0.126 | MFG |
| Cu5-98 | 936 | A | 605 | 0.817 | 262 | 0.354 | MFG |
| Cu5-99 | 874 | A | 383 | 0.380 | 299 | 0.297 | MFG |
| Cu5-100 | 970 | A | 411 | 0.390 | 164 | 0.156 | MFG |
| Cu5-101 | 876 | A | 189 | 0.160 | 162 | 0.137 | MFG |
| Cu5-102 | 886 | A | 156 | 0.143 | 131 | 0.120 | MFG |
| Cu5-103 | 882 | A | 171 | 0.149 | 145 | 0.126 | MFG |
| Cu5-104 | 880 | A | 452 | 0.518 | 341 | 0.391 | MFG |
| Cu5-105 | 934 | A | 737 | 1.144 | 301 | 0.467 | MFG |
| Cu5-106 | 700 | A | 141 | 0.312 | 134 | 0.297 | MFG |
| Cu5-117 | 724 | A | 159 | 0.302 | 143 | 0.272 | DMF |
| Cu5-118 | 936 | A | 708 | 0.573 | 286 | 0.231 | MFG |
| Cu5-119 | 872 | A | 660 | 1.037 | 498 | 0.782 | $H_2O$ |

TABLE 16

| | Maximum absorption wavelength | | Absorption coefficients at maximum absorption wavelength | | Absorption coefficients at 800 nm | | |
|---|---|---|---|---|---|---|---|
| Copper complex | Maximum absorption wavelength (nm) | Evaluation | Molar light absorption coefficient (L/mol · cm) | Gram light absorption coefficient (L/g · cm) | Molar light absorption coefficient (L/mol · cm) | Gram light absorption coefficient (L/g · cm) | Measurement solvent |
| Cu5-120 | 940 | A | 473 | 0.762 | 199 | 0.321 | MFG |
| Cu5-122 | 936 | A | 456 | 0.642 | 191 | 0.269 | MFG |
| Cu5-123 | 936 | A | 351 | 0.353 | 169 | 0.170 | MFG |
| Cu5-125 | 928 | A | 306 | 0.303 | 172 | 0.170 | MFG |
| Cu5-127 | 876 | A | 432 | 0.387 | 324 | 0.290 | MFG |
| Cu5-128 | 876 | A | 548 | 0.510 | 414 | 0.385 | MFG |
| Cu5-129 | 880 | A | 478 | 0.440 | 355 | 0.327 | MFG |
| Cu5-130 | 882 | A | 475 | 0.401 | 344 | 0.290 | MFG |
| Cu5-131 | 878 | A | 463 | 0.391 | 344 | 0.291 | MFG |
| Cu5-132 | 882 | A | 426 | 0.369 | 311 | 0.269 | MFG |
| Cu5-133 | 880 | A | 434 | 0.363 | 320 | 0.268 | MFG |
| Cu5-134 | 884 | A | 433 | 0.387 | 312 | 0.279 | MFG |
| Cu5-135 | 882 | A | 423 | 0.367 | 308 | 0.267 | MFG |
| Cu5-136 | 880 | A | 368 | 0.570 | 275 | 0.426 | MFG |
| Cu5-137 | 880 | A | 381 | 0.765 | 288 | 0.578 | MFG |
| Cu5-138 | 876 | A | 394 | 0.734 | 295 | 0.550 | MFG |
| Cu5-139 | 896 | A | 349 | 0.489 | 233 | 0.326 | MFG |
| Cu5-140 | 880 | A | 369 | 0.531 | 269 | 0.387 | MFG |
| Cu5-141 | 880 | A | 393 | 0.565 | 291 | 0.418 | MFG |
| Cu5-142 | 880 | A | 407 | 0.493 | 301 | 0.365 | MFG |
| Cu5-144 | 874 | A | 427 | 0.585 | 321 | 0.440 | MFG |
| Cu5-145 | 876 | A | 367 | 0.433 | 284 | 0.335 | MFG |
| Cu5-146 | 870 | A | 373 | 0.641 | 290 | 0.498 | MFG |
| Cu5-147 | 874 | A | 366 | 0.532 | 283 | 0.411 | MFG |
| Cu5-148 | 876 | A | 422 | 0.524 | 319 | 0.396 | MFG |
| Cu5-149 | 872 | A | 430 | 0.797 | 327 | 0.606 | MFG |
| Cu5-150 | 874 | A | 443 | 0.634 | 332 | 0.475 | MFG |
| Cu5-151 | 876 | A | 479 | 0.585 | 356 | 0.435 | MFG |
| Cu5-152 | 876 | A | 467 | 0.847 | 352 | 0.638 | MFG |
| Cu6-52 | 810 | A | 297 | 0.288 | 204 | 0.198 | MFG |
| Copper acetate | 680 | B | 136 | 0.750 | 71 | 0.392 | MFG |
| Cu7-1 | 820 | A | 50 | 0.104 | 45 | 0.094 | Acetone |
| Cu7-2 | 775 | A | 225000 | 10 | 40000 | 1.778 | 1,2,4-trichlorobenzene |

The τ value (calculated value) of each copper complex is shown below. All of the τ values (calculated value) of copper complexes were calculated by using a quantum chemical calculation program Gaussian 09 (manufactured by Gaussian, Inc.) and a density functional method was used as the method thereof. B3LYP was used as a general function and TZVP was used as a basis function. As a molecular structure used in the calculation of the τ value, a structure in which structural optimization calculation is performed to have the minimum generated energy was used.

TABLE 17

| Copper complex | τ value (calculated value) |
|---|---|
| Cu3-6 | 0.06 |
| Cu3-7 | 0.16 |
| Cu3-10 | 0.23 |
| Cu3-15 | 0.05 |
| Cu3-16 | 0.21 |
| Cu3-35 | 0.02 |
| Cu3-36 | 0.01 |
| Cu3-63 | 0.19 |
| Cu4-36 | 0.06 |
| Cu4-39 | 0.12 |
| Cu4-45 | 0.04 |
| Cu4-49 | 0.09 |
| Cu4-50 | 0.13 |
| Cu4-52 | 0.05 |
| Cu4-55 | 0.05 |
| Cu4-62 | 0.01 |
| Cu4-63 | 0.03 |
| Cu5-1 | 1.04 |
| Cu5-18 | 1.01 |
| Cu5-20 | 1.01 |
| Cu5-22 | 1.01 |
| Cu5-37 | 0.81 |
| Cu5-46 | 0.86 |
| Cu5-50 | 0.98 |
| Cu5-51 | 0.96 |
| Cu5-52 | 0.98 |
| Cu5-72 | 1.04 |
| Cu5-82 | 1.01 |
| Cu5-83 | 1.01 |
| Cu5-92 | 1.04 |
| Cu5-95 | 1.01 |
| Cu5-96 | 1.01 |
| Cu5-97 | 1.02 |
| Cu5-98 | 1.01 |
| Cu5-99 | 0.78 |
| Cu5-100 | 1.02 |
| Cu5-101 | 0.84 |
| Cu5-102 | 0.82 |
| Cu5-103 | 0.85 |
| Cu5-104 | 0.98 |
| Cu5-105 | 1.01 |
| Cu5-106 | 0.69 |
| Cu5-117 | 1.06 |
| Cu5-118 | 1.01 |
| Cu5-119 | 0.98 |
| Cu5-120 | 1.01 |
| Cu5-122 | 1.01 |
| Cu5-123 | 0.95 |
| Cu5-125 | 0.90 |
| Cu5-127 | 0.77 |
| Cu5-128 | 0.79 |
| Cu5-129 | 0.80 |
| Cu5-130 | 0.81 |
| Cu5-131 | 0.79 |
| Cu5-132 | 0.77 |
| Cu5-133 | 0.77 |
| Cu5-134 | 0.78 |
| Cu5-135 | 0.77 |
| Cu5-136 | 0.78 |
| Cu5-137 | 0.78 |
| Cu5-138 | 0.77 |
| Cu5-139 | 0.77 |
| Cu5-140 | 0.77 |
| Cu5-141 | 0.77 |
| Cu5-142 | 0.77 |
| Cu5-144 | 0.77 |
| Cu5-145 | 0.77 |
| Cu5-146 | 0.77 |
| Cu5-147 | 0.79 |
| Cu5-148 | 0.79 |
| Cu5-149 | 0.79 |
| Cu5-150 | 0.77 |
| Cu5-151 | 0.77 |
| Cu5-152 | 0.77 |
| Cu6-52 | 1.00 |

When a copper complex has the τ value close to 1, the copper complex easily becomes a copper complex having a maximum absorption wavelength at the vicinity of a wavelength of 900 nm and it is possible to shield near infrared light over a wide region.

In the copper complexes in the tables described above, Cu7-1 and Cu7-2 are compounds having the following structures.

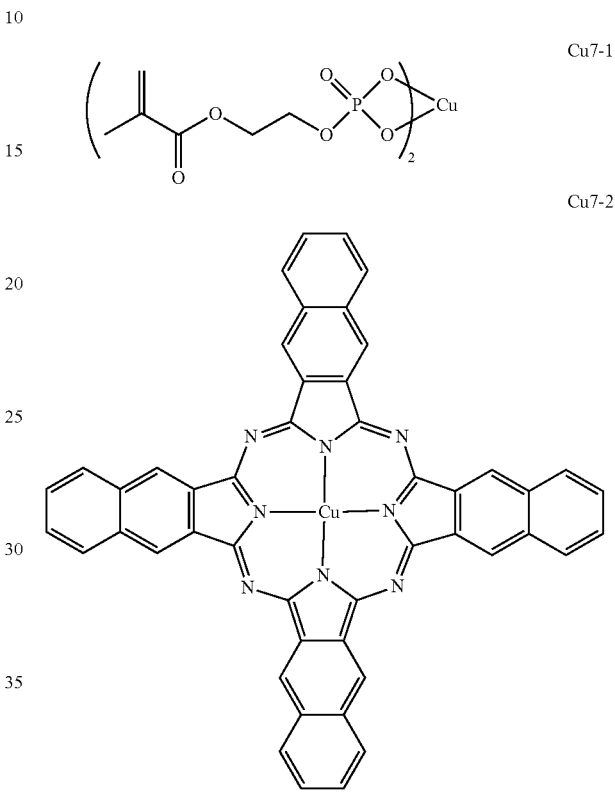

<Preparation of Near Infrared Ray Absorbent Composition>

The copper complex (20 parts by mass) shown in the following tables, KAYARAD DPHA (20 parts by mass), JER157S65 (20 parts by mass), and PGMEA (120 parts by mass) were mixed with each other and a near infrared ray absorbent composition was prepared.

<Preparation of Near Infrared Ray Cut Filter>

A near infrared ray cut filter was prepared by using the near infrared ray absorbent composition described above.

A photoresist was applied onto a glass substrate, and a partition wall of the photoresist was formed by patterning the photoresist using lithography, and thus, a dropwise addition region of the near infrared ray absorbent composition was formed. 3 ml of each near infrared ray absorbent composition was subjected to dropwise addition in the dropwise addition region on the glass substrate, and was dried by being left to stand at a room temperature for 24 hours. A film thickness of a coated film after being dried was evaluated, and the film thickness was 100 μm.

<<Evaluation of Near Infrared Ray Shielding Properties>>

The transmittance of the near infrared ray cut filter obtained as described above at a wavelength of 800 nm was measured by using a SPECTROPHOTOMETER U-4100 (manufactured by Hitachi High-Technologies Corporation).

Near infrared ray shielding properties were evaluated on the basis of the following criteria. The results are shown in the following table.
- A: Transmittance at 800 nm≤5%
- B: 5%<Transmittance at 800 nm≤25%
- C: 25%<Transmittance at 800 nm <<Evaluation of Visible Light Transmittance>>

The transmittance of the near infrared ray cut filter obtained as described above at a wavelength of 550 nm was measured by using a SPECTROPHOTOMETER U-4100 (manufactured by Hitachi High-Technologies Corporation). A visible light transmittance was evaluated on the basis of the following criteria. The results are shown in the following tables.
- A: 85% Transmittance at Wavelength of 550 nm
- B: 45% Transmittance at Wavelength 550 nm>85%
- C: Transmittance at Wavelength 550 nm≤45%

TABLE 18

| | Copper complex | Visible light transmittance | Near infrared ray shielding properties |
|---|---|---|---|
| Example 1 | Cu3-6 | A | A |
| Example 2 | Cu3-7 | B | A |
| Example 3 | Cu3-10 | A | A |
| Example 4 | Cu3-15 | A | A |
| Example 5 | Cu3-16 | A | A |
| Example 6 | Cu3-35 | A | A |
| Example 7 | Cu3-56 | A | B |
| Example 8 | Cu3-63 | B | B |
| Example 9 | Cu4-36 | A | A |
| Example 10 | Cu4-39 | A | A |
| Example 11 | Cu4-45 | A | A |
| Example 12 | Cu4-49 | B | A |
| Example 13 | Cu4-52 | A | B |
| Example 14 | Cu4-62 | A | B |
| Example 15 | Cu4-63 | A | A |
| Example 16 | Cu5-1 | A | B |
| Example 17 | Cu5-20 | A | A |
| Example 18 | Cu5-37 | A | A |
| Example 19 | Cu5-48 | A | A |
| Example 20 | Cu5-50 | B | A |
| Example 21 | Cu5-51 | B | A |
| Example 22 | Cu5-52 | A | A |
| Example 23 | Cu5-72 | A | B |
| Example 24 | Cu5-82 | A | B |
| Example 25 | Cu5-83 | A | B |
| Example 26 | Cu5-92 | A | B |
| Example 27 | Cu5-95 | A | A |
| Example 28 | Cu5-96 | A | A |
| Example 29 | Cu5-97 | A | B |
| Example 30 | Cu5-98 | A | A |
| Example 31 | Cu5-99 | A | A |
| Example 32 | Cu5-100 | A | B |
| Example 33 | Cu5-101 | A | B |
| Example 34 | Cu5-102 | A | B |
| Example 35 | Cu5-103 | A | B |
| Example 36 | Cu5-104 | A | A |
| Example 37 | Cu5-105 | A | A |
| Example 38 | Cu5-106 | B | A |
| Example 39 | Cu5-117 | A | A |
| Example 40 | Cu5-118 | A | B |
| Example 41 | Cu5-119 | A | A |
| Example 42 | Cu5-22 | A | A |
| Example 43 | Cu4-50 | B | B |
| Example 44 | Cu4-55 | A | B |
| Example 45 | Cu5-18 | B | A |

TABLE 19

| | Copper complex | Visible light transmittance | Near infrared ray shielding properties |
|---|---|---|---|
| Example 46 | Cu5-120 | A | A |
| Example 47 | Cu5-122 | A | A |
| Example 48 | Cu5-123 | A | B |
| Example 49 | Cu5-125 | A | B |
| Example 50 | Cu5-127 | A | A |
| Example 51 | Cu5-128 | A | A |
| Example 52 | Cu5-129 | A | A |
| Example 53 | Cu5-130 | A | A |
| Example 54 | Cu5-131 | A | A |
| Example 55 | Cu5-132 | A | A |
| Example 56 | Cu5-133 | A | A |
| Example 57 | Cu5-134 | A | A |
| Example 58 | Cu5-135 | A | A |
| Example 59 | Cu5-136 | A | A |
| Example 60 | Cu5-137 | A | A |
| Example 61 | Cu5-138 | A | A |
| Example 62 | Cu5-139 | A | A |
| Example 63 | Cu5-140 | A | A |
| Example 64 | Cu5-141 | A | A |
| Example 65 | Cu5-142 | A | A |
| Example 66 | Cu5-144 | A | A |
| Example 67 | Cu5-145 | A | A |
| Example 68 | Cu5-146 | A | A |
| Example 69 | Cu5-147 | A | A |
| Example 70 | Cu5-148 | A | A |
| Example 71 | Cu5-149 | A | A |
| Example 72 | Cu5-150 | A | A |
| Example 73 | Cu5-151 | A | A |
| Example 74 | Cu5-152 | A | A |
| Example 75 | Cu6-52 | A | B |
| Comparative Example 1 | Copper acetate | C | A |
| Comparative Example 2 | Cu7-1 | A | C |
| Comparative Example 3 | Cu7-2 | C | A |

As clearly shown in the tables described above, in the near infrared ray absorbent compositions of the examples, high shielding properties in a near infrared ray range were obtained, even in a case of a thin film having a thickness of 100 μm, and excellent near infrared ray shielding properties which are equivalent to those in Comparative Examples 1 and 3 in which a copper phthalocyanine complex or copper acetate was used, were obtained. In addition, it was found that, regarding all of the near infrared ray cut filters of the examples, light transmittance at a wavelength of 550 nm was greater than or equal to 45%, and high transmittance in a visible light range and high shielding properties in a near infrared ray range were obtained. Further, it was confirmed that, regarding the near infrared ray cut filters of the examples, light transmittance in a wavelength range of 450 to 550 nm was greater than or equal to 45% and light transmittance in a wavelength range of 800 to 900 nm was less than or equal to 25%. It was found that, regarding the near infrared ray cut filters of the examples, high transmittance was ensured for a wide visible light range and excellent spectral characteristics were obtained.

Meanwhile, regarding the near infrared ray absorbent compositions of the comparative examples, both of increasing light transmittance in a wavelength range of 450 to 550 nm and decreasing light transmittance in a wavelength range of 800 to 900 nm were not satisfied.

In the near infrared ray absorbent compositions of Examples 1 to 75, even in a case where 20 parts by mass of the polymerizable compound (KAYARAD DPHA) is changed into the equivalent amount of KAYARAD D-320, M-510, M-520, or DPCA-60, excellent effects are obtained in the same manner as those in the examples.

In the near infrared ray absorbent compositions of Examples 1 to 75, even in a case where the content of the copper complex with respect to the total solid content of the composition is set as 15 mass %, 20 mass %, 30 mass %, or 40 mass %, excellent near infrared ray shielding properties are obtained in the same manner as those in the examples.

In the near infrared ray absorbent compositions of Examples 1 to 75, even in a case where the content of the solvent (PGMEA) is set as 10 mass %, 20 mass %, 30 mass %, or 40 mass %, excellent coating properties are obtained in the same manner as those of the near infrared ray absorbent compositions in the examples.

In the near infrared ray absorbent compositions of Examples 1 to 75, even in a case where the solvent is changed to cyclohexanone, ethyl lactate, ethanol, or cyclopentanone, excellent coating properties are obtained in the same manner as those of the near infrared ray absorbent compositions in the examples.

In the near infrared ray absorbent compositions of Examples 1 to 75, even in a case where the filtering is performed by using DFA4201NXEY (nylon filter having an aperture of 0.45 µm) manufactured by Pall Corporation after preparing each composition, the same effects are obtained.

40 parts by mass of each copper complex used in Examples 1 to 75, 54.9 parts by mass of a polymer (P-1) exemplified as the specific example of the compound having a partial structure represented by M-X described above, 5 parts by mass of IRGACURE-OXE01 (manufactured by BASF SE), 0.1 parts by mass of tris(2,4-pentanedionato) aluminum (manufactured by Tokyo Chemical Industry Co., Ltd.), and 66.7 parts by mass of cyclohexanone were mixed with each other to prepare a near infrared ray absorbent composition. Even in a case of using this near infrared ray absorbent composition, excellent effects are obtained in the same manner as in Examples 1 to 75.

Even in a case where polymers (P-2) to (P-44) exemplified as the specific example of the compound having a partial structure represented by M-X described above are used instead of the polymer (P-1), excellent effects are obtained in the same manner in examples.

<Synthesis of Compound Having Partial Structure Represented by M-X>

<Synthesis of Polymer (P-1)>

1-methoxy-2-propanol (20 g) was added to a three-neck flask, and was heated to 85° C. under a nitrogen atmosphere. A solution in which methacrylic acid 2-ethyl hexyl (16.35 g), methacrylic acid 3-(trimethoxy silyl) propyl (13.65 g), and V-601 (manufactured by Wako Pure Chemical Industries, Ltd., an azo-based polymerization initiator, 1.27 g) were dissolved in 1-methoxy-2-propanol (50 g) was subjected to dropwise addition for 2 hours. After the dropwise addition ended, a reaction ended by performing stirring for 4 hours, and thus, a polymer (P-1) of the structural formula described above was obtained. The weight-average molecular weight of the polymer (P-1) was 20,000.

<Synthesis of Polymers (P-2) to (P-44)>

Polymers (P-2) to (P-44) of the structural formula described above were produced by the same method as that of the polymer (P-1).

EXPLANATION OF REFERENCES

10: camera module
11: solid image pickup element
12: planarizing layer
13: near infrared ray cut filter
14: imaging lens
15: lens holder
16: silicon substrate
17: color filter
18: micro lens
19: ultraviolet and infrared light reflection film
20: transparent substrate
21: near infrared ray absorption layer
22: antireflection layer

What is claimed is:

1. A near infrared ray absorbent composition comprising:

a copper complex that is other than a copper phthalocyanine complex;

wherein the copper complex has a maximum absorption wavelength in a wavelength range of 700 to 1,200 nm and has a molar light absorption coefficient at the maximum absorption wavelength of greater than or equal to 100 (L/mol·cm), and the copper complex comprises a compound represented by Formula (IV-12') or a compound represented by Formula (IV-13') as a ligand;

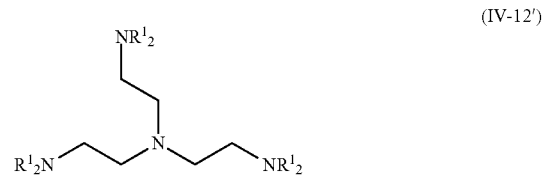

(IV-12')

wherein each of $R^1$ independently represents a hydrogen atom, an alkyl group, an alkenyl group, an alkynyl group, an aryl group, or a heteroaryl group,

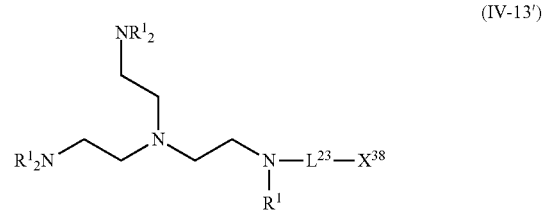

(IV-13')

wherein each of $R^1$ independently represents a hydrogen atom, an alkyl group, an alkenyl group, an alkynyl group, an aryl group, or a heteroaryl group, $L^{23}$ represents a single bond or a divalent linking group, $X^{38}$ represents a coordination portion.

2. A near infrared ray absorbent composition comprising:

a copper complex that includes a compound not having a maximum absorption wavelength in a wavelength range of 400 to 600 nm as a ligand;

wherein the copper complex has a maximum absorption wavelength in a wavelength range of 700 to 1,200 nm and has a molar light absorption coefficient at the maximum absorption wavelength of greater than or equal to 100 (L/mol·cm), and the copper complex comprises a compound represented by Formula (IV-12') or a compound represented by Formula (IV-13') as a ligand;

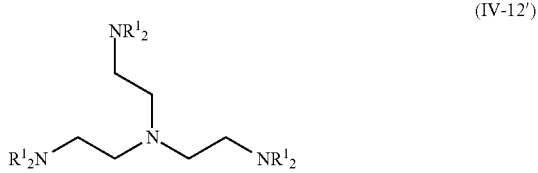

(IV-12′)

wherein each of $R^1$ independently represents a hydrogen atom, an alkyl group, an alkenyl group, an alkynyl group, an aryl group, or a heteroaryl group,

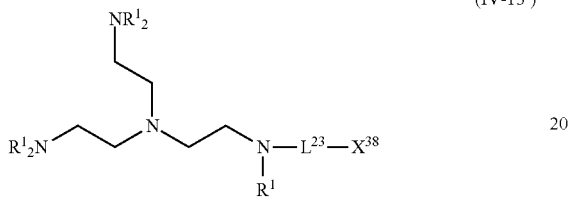

(IV-13′)

wherein each of $R^1$ independently represents a hydrogen atom, an alkyl group, an alkenyl group, an alkynyl group, an aryl group, or a heteroaryl group, $L^{23}$ represents a single bond or a divalent linking group, $X^{38}$ represents a coordination portion.

3. The near infrared ray absorbent composition according to claim 1,
wherein, in the copper complex, a 5-membered ring and/or a 6-membered ring is formed by copper and a ligand.

4. The near infrared ray absorbent composition according to claim 1,
wherein the content of the copper complex is greater than or equal to 15 mass % with respect to the total solid content of the near infrared ray absorbent composition.

5. The near infrared ray absorbent composition according to claim 1, further comprising:
a curable compound; and
a solvent.

6. The near infrared ray absorbent composition according to claim 1,
wherein, when a film having a film thickness after being dried of 100 μm is prepared by using the near infrared ray absorbent composition, light transmittance in a thickness direction of the film at a wavelength of 550 nm is greater than or equal to 45%, and light transmittance at a wavelength of 800 nm is less than or equal to 25%.

7. A near infrared ray cut filter obtained by using the near infrared ray absorbent composition according to claim 1.

8. The near infrared ray cut filter according to claim 7, wherein a film thickness is less than or equal to 300 μm.

9. A solid image pickup element comprising:
a near infrared ray cut filter obtained by using the near infrared ray absorbent composition according to claim 1.

10. A camera module comprising:
a solid image pickup element; and
a near infrared ray cut filter disposed on the solid image pickup element on a light receiving side,
wherein the near infrared ray cut filter is the near infrared ray cut filter according to claim 7.

11. A near infrared ray absorbent composition comprising:
a copper complex that is other than a copper phthalocyanine complex;
wherein the copper complex has a maximum absorption wavelength in a wavelength range of 700 to 1,200 nm and has a molar light absorption coefficient at the maximum absorption wavelength of greater than or equal to 100 (L/mol·cm), and
the copper complex comprises a compound represented by Formula (IV-12) as a ligand and further comprises at least one unidentate ligand,

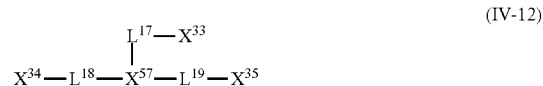

(IV-12)

wherein $X^{33}$, $X^{34}$, $X^{35}$ and $X^{57}$ each independently represent a coordination portion containing a coordination atom coordinating to copper by an unshared electron pair,
wherein the coordination atom is an oxygen atom, a nitrogen atom, a sulfur atom or a phosphorus atom,
$L^{17}$ to $L^{19}$ each independently represent a single bond or a divalent linking group.

12. A near infrared ray absorbent composition comprising:
a copper complex that includes a compound not having a maximum absorption wavelength in a wavelength range of 400 to 600 nm as a ligand,
wherein the copper complex has a maximum absorption wavelength in a wavelength range of 700 to 1,200 nm and has a molar light absorption coefficient at the maximum absorption wavelength of greater than or equal to 100 (L/mol·cm), and
wherein the copper complex comprises a compound represented by Formula (IV-12) as a ligand and further comprises at least one unidentate ligand,

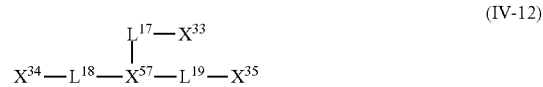

(IV-12)

wherein $X^{33}$, $X^{34}$, $X^{35}$ and $X^{57}$ each independently represent a coordination portion containing a coordination atom coordinating to copper by an unshared electron pair,
wherein the coordination atom is an oxygen atom, a nitrogen atom, a sulfur atom or a phosphorus atom,
$L^{17}$ to $L^{19}$ each independently represent a single bond or a divalent linking group.

13. The near infrared ray absorbent composition according to claim 1,
wherein each of $R^1$ represents an alkyl group.

14. The near infrared ray absorbent composition according to claim 2,
wherein each of $R^1$ represents an alkyl group.

15. The near infrared ray absorbent composition according to claim 11,
wherein the coordination atom is an oxygen atom or a nitrogen atom.

16. The near infrared ray absorbent composition according to claim 11,
wherein $X^{33}$ to $X^{35}$ each independently is selected from group (UE-1) and $X^{33}$ is selected from group (UE-3):

Group (UE-1)

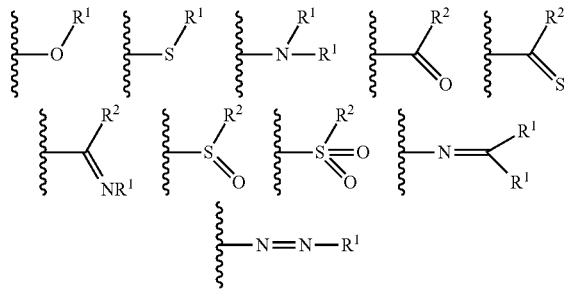

wherein $R^1$ represents a hydrogen atom, an alkyl group, an alkenyl group, an alkynyl group, an aryl group, or a heteroaryl group, and $R^2$ represents a hydrogen atom, an alkyl group, an alkenyl group, an alkynyl group, an aryl group, a heteroaryl group, an alkoxy group, an aryloxy group, a heteroaryloxy group, an alkyl thio group, an aryl thio group, a heteroaryl thio group, an amino group, or an acyl group, and Group (UE-3)

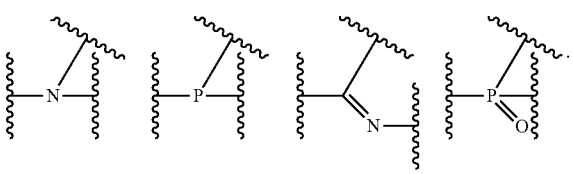

17. The near infrared ray absorbent composition according to claim 11,
wherein the unidentate ligand is a unidentate ligand performing coordination by an anion.

18. The near infrared ray absorbent composition according to claim 12,
wherein the coordination atom is an oxygen atom or a nitrogen atom.

19. The near infrared ray absorbent composition according to claim 12,
wherein $X^{33}$ to $X^{35}$ each independently is selected from group (UE-1) and $X^{33}$ is selected from group (UE-3):

Group (UE-1)

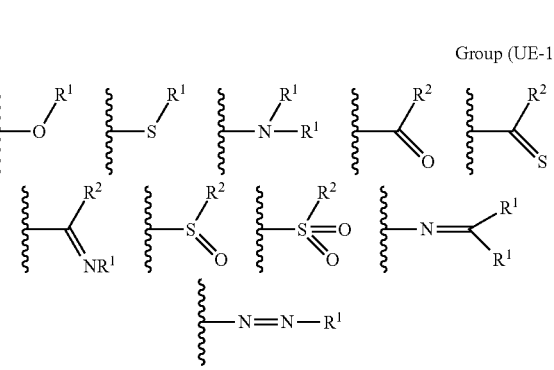

wherein $R^1$ represents a hydrogen atom, an alkyl group, an alkenyl group, an alkynyl group, an aryl group, or a heteroaryl group, and $R^2$ represents a hydrogen atom, an alkyl group, an alkenyl group, an alkynyl group, an aryl group, a heteroaryl group, an alkoxy group, an aryloxy group, a heteroaryloxy group, an alkyl thio group, an aryl thio group, a heteroaryl thio group, an amino group, or an acyl group, and Group (UE-3)

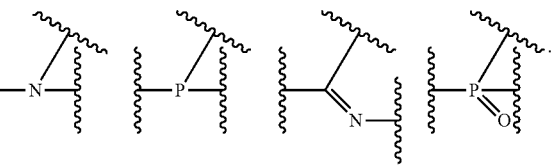

20. The near infrared ray absorbent composition according to claim 12,
wherein the unidentate ligand is a unidentate ligand performing coordination by an anion.

* * * * *